(12) United States Patent
Lewis et al.

(10) Patent No.: US 10,392,622 B2
(45) Date of Patent: Aug. 27, 2019

(54) COMPOSITIONS AND METHODS FOR SELF-REGULATED INDUCIBLE GENE EXPRESSION

(71) Applicant: The Trustees of the University of Pennsylvania, Philadelphia, PA (US)

(72) Inventors: Mitchell Lewis, Bala Cynwyd, PA (US); Jean Bennett, Bryn Mawr, PA (US); Luk Vandenberghe, Weston, MA (US); Matthew Sochor, Watertown, MA (US); Theodore G. Drivas, New York, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/500,591

(22) PCT Filed: Jul. 31, 2015

(86) PCT No.: PCT/US2015/043335
§ 371 (c)(1),
(2) Date: Jan. 31, 2017

(87) PCT Pub. No.: WO2016/019364
PCT Pub. Date: Feb. 4, 2016

(65) Prior Publication Data
US 2017/0218379 A1    Aug. 3, 2017

Related U.S. Application Data

(60) Provisional application No. 62/159,797, filed on May 11, 2015, provisional application No. 62/032,449, filed on Aug. 1, 2014.

(51) Int. Cl.
*C12N 15/63* (2006.01)

(52) U.S. Cl.
CPC .......... *C12N 15/635* (2013.01); *C12N 15/63* (2013.01); *C12N 2830/52* (2013.01)

(58) Field of Classification Search
None
See application file for complete search history.

(56) References Cited

U.S. PATENT DOCUMENTS 6,004,941 A    12/1999 Bujard et al.
6,340,741 B1    1/2002 Mermod et al.
(Continued)

OTHER PUBLICATIONS

Becskei et al., Engineering stability in gene networks by autoregulation. Nature, vol. 405, pp. 590-593, Jun. 2000 (Year: 2000).*
(Continued)

*Primary Examiner* — Christopher M Babic
*Assistant Examiner* — Arthur S Leonard
(74) *Attorney, Agent, or Firm* — Howson and Howson LLP

(57) ABSTRACT

A self-regulating gene expression construct comprises a single promoter in operative association with a repressor sequence (e.g., bacterial repressor lacI or gaiR), operator sequence(s) responsive to the expressed repressor protein, and a transgene. A dual-regulating construct comprises a single promoter controlling expression of a bacterial repressor sequence and a transgene, and which, in the presence of a first inducer molecule, transcribes the transgene and repressor; and a ribozyme in association with an aptamer sequence, the aptamer sequence capable of interacting with a second inducer molecule to terminate mRNA degradation by the ribozyme. Also provided are recombinant vectors or viruses containing the self-regulating or dual self-regulating constructs and cells containing the vectors. Such compositions are useful in methods of treating a diseases using gene therapy.

16 Claims, 22 Drawing Sheets

Specification includes a Sequence Listing.

(56) References Cited

U.S. PATENT DOCUMENTS

| | | | |
|---|---|---|---|
| 7,390,645 | B2 | 6/2008 | Matthews et al. |
| 9,315,825 | B2* | 4/2016 | Wilson .................. C12N 15/86 |
| 2004/0022766 | A1 | 2/2004 | Acland et al. |
| 2010/0166769 | A1 | 7/2010 | Hsiao et al. |
| 2010/0175141 | A1 | 7/2010 | Collins et al. |
| 2010/0286082 | A1 | 11/2010 | Breaker et al. |

OTHER PUBLICATIONS

Wittmann et al., Engineered riboswitches: Expanding researchers' toolbox with synthetic RNA regulators. FEBS Letters 586 (2012) 2076-2083 (Year: 2012).*
Beilstein, K et al, May 2015, Conditional control of mammalian gene expression by tetracycline-dependent hammerhead ribozyme. ACS Synth Biol., 4(5):526-534.
Bennett, J. et al., Gene delivery to the Retina: From mouse to man. Methods Enzymol. 507, 255-274 (2012). doi:10.1016/B978-0-12-386509-0.00013-2.
Burcin, MM et al, Jan. 1999, Adenovirus-mediated regulatable target gene expression in vivo. Proc. Natl. Acad. Sci. USA, 96(2): 355-360.
Chen, Y. et al., RANGE: Gene Transfer of Reversibly Controlled Polycistronic Genes. Apr. 2013, Mol. Ther. Nucleic Acids 2 (4): e85.
Chtarto, A. et al. A next step in adeno-associated virus-mediated gene therapy for neurological diseases: regulation and targeting. Br. J. Clin. Pharmacol. 76 (2): 217-232 (Jan. 2013).
Cronin CA, et al. Dec. 2003, Tyrosinase expression during neuroblast divisions affects later pathfinding by retinal ganglion cells. J Neurosci 23(37): 11692-11697.
Cronin, CA. et al., The lac operator-repressor system is functional in the mouse. *Genes Dev.* 15, 1506-1517 (Jun. 2001).
Daber, R. & Lewis, M. A novel molecular switch. J. Mol. Biol. 391 (4): 661-670 (Aug. 2009).
Daber, R. et al. One is not enough. J. Mol. Biol. 392 (5): 1133-1144 (Oct. 2009).
Daber, R., et al., Thermodynamic analysis of mutant lac repressors. J. Mol. Biol. 409(1): 76-87 (May 2011).
Danielian, PS, et al. Nov. 1998, Modification of gene activity in mouse embryos in utero by a tamoxifen-inducible form of Cre recombinase. Curr Biol 8: 1323-1326.
Dejneka, N. et al, 2003 Gene therapy and animal models for retinal disease. Genetics in Opthalmology, 37: 188-198.
Donnelly, ML, et al, Jan. 1997, The cleavage activities of aphthovirus and cardiovirus 2A proteins. J. Gen. Virol., 78(Pt 1):13-21.
Donnelly, ML, et al 2001 Analysis of the aphthovirus 2A/2B polyprotein 'cleavage' mechanism indicates not a proteolytic reaction, but a novel translational effect: a putative ribosomal 'skip'. J Gen Virol 82: 1013-1025.
Gossen, M and Bujard, H (Jun. 1992) Tight control of gene expression in mammalian cells by tetracycline-responsive promoters. Proc Natl Acad Sci USA 89(12):5547-5551.
Guo et al, Characterization of the Host Factors Required for Hepadnavirus Covalently Closed Circular (ccc) DNA Formation, PLoS One, Aug. 13, 2012, 7(8):e43270:1-10.
Maguire, A. et al. Safety and Efficacy of Gene Transfer for Leber's Congenital Amaurosis. N. Engl. J. Med. 358, 2240-2248 (May 2008).
Maloy, S. & Stewart, V. Autogenous regulation of gene expression. *J. Bacterial.* 175 (2), 307-16 (Jan. 1993).
Milk L, et al. Mar. 2010, Functional rules for lac repressor-operator associations and implications for protein-DNA interactions. Protein Sci, 19: 1162-1172.
Nevozhay, D., et al. Negative autoregulation linearizes the dose-response and suppresses the heterogeneity of gene expression. Proc. Natl. Acad. Sci. U. S. A., 106 (13): 5123-5128 (Mar. 2009).
No, D, et al. Apr. 1996, Ecdysone-inducible gene expression in mammalian cells and transgenic mice. Proc Natl Acad Sci U S A, 93: 3346-3351.
Oehler, S. et al. 1990 The three operators of the lac operon cooperate in repression. EMBO J., 9 (4): 973-979.
Oehler, S., et al, 1994 Quality and position of the three lac operators of *E. coli* define efficiency of repression. EMBO J., 13(14): 3348-3355.
Santoso, L et al, Dec. 2006, "On the Modeling of a Bistable Genetic Switch" in Proceedings of the 45th IEEE Conference on Decision and Control.
Scrable, H. & Stambrook, P. J. Activation of the lac Repressor in the Transgenic Mouse. Genetics 147 (1): 297-304 (Sep. 1997).
Sochor, Ma (Jul. 2014) In vitro transcription accurately predicts lac repressor phenotype in vivo in *Escherichia coli*. Peer J e498.
Sochor, MA (2014) Allostery and Applications of the Lac Repressor, Dissertation, University of Pennsylvania.
Swint-Kruse, L. & Matthews, K. S., Allostery in the LacI/GalR Family: Variations on a Theme. Curr. Opin. Microbiol. 12 (2), 129-37 (Apr. 2009).
Trichas G, et al, Sep. 2008, Use of the viral 2A peptide for bicistronic expression in transgenic mice. BMC Biol 6: 40.
Vasireddy, V. et al, AAV-Mediated Gene Therapy for Choroideremia: Preclinical Studies in Personalized Models. PLoS One, 8(5): e61396 (May 2013).
Zoltnick, PW and Wilson, JM, Regulated Gene Expression in Gene Therapy, Annals NY Acad Sci., 953:53-63 (Dec. 2001).
International Preliminary Report on Patentability dated Feb. 16, 2017 in corresponding International Patent Application No. PCT/US2015/043335.
Suess, B. and Weigand, J. E., Engineered riboswitches: Overview, problems, and trends, RNA Biology, Mar. 2008, 5(1):1-6.
Kim, J. H. et al., High Cleavage Efficiency of a 2A Peptide Derived from Porcine Teschovirus-1 in Human Cell Lines, Zebrafish, and Mice, Plos One, Apr. 2011, 6(4): e18556 1-8.
Chen, J. and Matthews, K. S., Deletion of Lactose Repressor Carboxyl-terminal Domain Affects Tetramer Formation, The Journal of Biological Chemistry, Jul. 1992, 267(20):13843-13850.
Sadler, J. R. et al., A perfectly symmetric lac operator binds the lac repressor very tightly, Proc Natl Acad Sci USA, Nov. 1983, 80:6785-6789.
International Search Report dated Nov. 20, 2015 in corresponding International Patent Application No. PCT/US2015/043335.
Written Opinion dated Nov. 20, 2015 in corresponding International Patent Application No. PCT/US2015/043335.
Dejneka, N. S. et al., Pharmacologically regulated gene expression in the retina following transduction with viral vectors, Gene Therapy, Mar. 2001, 8(6):442-446.
Figge, J. et al., Stringent regulation of stably integrated chloramphenicol acetyl transferase genes by *E. coli* lac repressor in monkey cells, Cell, Mar. 1988, 52:713-722.
Hu, M. C. & Davidson, N., The inducible lac operator-repressor system is functional in mammalian cells, Cell, Feb. 1987, 48(4):555-566.
Becskei, A. & Serrano, L., Engineering stability in gene networks by autoregulation, Nature, Jun. 2000, 405:590-593.
Ginn, S. L. et al., Gene therapy clinical trials worldwide to 2012—an update, The Journal of Gene Medicine, Feb. 2013, 15:65-77.
Goldberger, R. F. et al., Autogenous regulation of gene expression, Science, Mar. 1974, 183:810-816.
Hu, M. C. & Davidson, N , Targeting the *Escherichia coli* lac repressor to the mammalian cell nucleus, Gene, Mar. 1991, 99:141-150.
Jacob, F. & Monod, J., Genetic regulatory mechanisms in the synthesis of proteins, Journal of Molecular Biology, Jun. 1961, 3(3):318-356.
Karlsson, M. et al., De novo design and construction of an inducible gene expression system in mammalian cells, Methods in Enzymology, May 2011, 497:239-253.
Lewis, M., The lac repressor, Comptes Rendus Biologies, Jun. 2005, 328(6):521-548.
Liang, F-Q, et al. Intraocular delivery of recombinant virus, Methods in Molecular Medicine, 200047: Ocular Molecular Biology Protocols, Rakoczy PE (ed) pp. 125-139. Totowa, NJ: Humana Press Inc.

(56) References Cited

OTHER PUBLICATIONS

Manfredsson FP, et al. 2012 Regulated protein expression for in vivo gene therapy for neurological disorders: progress, strategies, and issues. Neurobiol Dis 48: 212-221.
Rosenfeld, N., et al. Negative Autoregulation Speeds the Response Times of Transcription Networks. J. Mol. Biol. 323 (5): 785-793 (Nov. 2002).
Savageau, M. A. Comparison of classical and autogenous systems of regulation in inducible operons. Nature 252, 546-549 (Dec. 1974).
Sharp, KA, Allostery in the lac operon: population selection or induced dissociation? Biophys. Chem. 159 (1): 66-72 (Nov. 2011).
Szymczak AL, Vignali DA (May 2005) Development of 2A peptide-based strategies in the design of multicistronic vectors. Expert Opin Biol Ther, 5(5): 627-638.
Toniatti, C., et al. Gene therapy progress and prospects: transcription regulatory systems. Gene Ther. 11(8): 649-57 (Apr. 2004).
Weiss R et al, 2003 Genetic Circuit Building Blocks for Cellular Computation, Communications, and Signal Processing, Natural Computing 2(1):47-84.

* cited by examiner pAAV.CMV.Lsym.YFP.IRES.EuLac::mCh (p794)
7808 bp

FIG. 5

Nucleic acid sequence of plasmid p794 cttccgcttcctcgctcactgactcgctgcgctcggtcgttcggctgcggcgagcggtatcagctcactcaaaggcggtaatacggttatcca
cagaatcaggggataacgcaggaaagaacatgtgagcaaaaccgcagcaaaaggccaggaaccgtaaaaaggccgcgttgctggcgtt
tttccataggctccgcccccctgacgagcatcacaaaaatcgacgctcaagtcagaggtggcgaaacccgacaggactataaagatacca
ggcgtttccccctggaagctccctcgtgcgctctcctgttccgaccctgccgcttaccggatacctgtccgcctttctcccttcgggaagcgtg
gcgctttctcatagctcacgctgtaggtatctcagttcggtgtaggtcgttcgctccaagctgggctgtgtgcacgaaccccccgttcagccc
gaccgctgcgccttatccggtaactatcgtcttgagtccaacccggtaagacacgacttatcgccactggcagcagccactggtaacaggat
tagcagagcgaggtatgtaggcggtgctacagagttcttgaagtggtggcctaactacggctacactagaaggacagtatttggtatctgcg
ctctgctgaagccagttaccttcggaaaaagagttggtagctcttgatccggcaaacaaaccaccgctggtagcggtggtttttttgtttgcaa
gcagcagattacgcgcagaaaaaaaggatctcaagaagatcctttgatcttttctacggggtctgacgctcagtggaacgaaaactcacgtt
aagggattttggtcatgagattatcaaaaaggatcttcacctagatccttttaaattaaaaatgaagttttaaatcaatctaaagtatatatgagtaa
acttggtctgacagttaccaatgcttaatcagtgaggcacctatctcagcgatctgtctatttcgttcatccatagttgcctgactccccgtcgtgt
agataactacgatacgggagggcttaccatctggccccagtgctgcaatgataccgcgagacccacgctcaccggctccagatttatcagc
aataaaccagccagccggaagggccgagcgcagaagtggtcctgcaactttatccgcctccatccagtctattaattgttgccgggaagcta
gagtaagtagttcgccagttaatagtttgcgcaacgttgttaccattactacaggcatcgtggtgtcacgctcgtcgtttggtatggcttcattca
gctccggttcccaacgatcaaggcgagttacatgatcccccatgttgtgcaaaaaagcggttagctccttcggtcctccgatcgttgtcagaa
gtaagttggccgcagtgttatcactcatggttatggcagcactgcataattctcttactgtcatgccatccgtaagatgcttttctgtgactggtga
gtactcaaccaagtcattctgagaatagtgtatgcggcgaccgagttgctcttgcccggcgtcaatacgggataataccgcgccacatagca
gaactttaaaagtgctcatcattggaaaacgttcttcggggcgaaaactctcaaggatcttaccactattgagatccagttcgatgtaacccact
cgtgcacccaactgatcttcagcatcttttactttcaccagcgtttctgggtgagcaaaaacaggaaggcaaaatgccgcaaaaaagggaat
aagggcgacacggaaatgttgaatactcatactcttcctttttcaatattattgaagcatttatcagggttattgtctcatgagcggatacatatttg
aatgtatttagaaaaataaacaataggggttccgcgcacatttccccgaaaagtgccacctgaaattataaacgttaatattttgttaaaattcg
cgttaaattttgttaaatcagctcatttttaaccaataggccgaaatcggcaaaaatcccttataaatcaaaagaatagaccgagataggggttga
gtgttgttccagtttggaacaagagtccactattgaggaacgtgaactccagcgtcaaagggcgaaaaaccgtctatcggggcgatggccc
actacgtgaaccatcacccctaatcaagttttttggggtcgaggtgccgtaaagcactaaatcggaaccctaaagggagccccccgatttagag
cttgacggggaaagccggcgaacgtggcgagaaaggaagggaagaaagcgaaaggagcgggcgctagggcgctggcaagtgtagc
ggtcacgctgcgcgtaaccaccacacccgccgcgcttaatgcgccgctacagggcgcgtcccattcgccattcaggctgcgcaactgttg
ggaagggcgatcggtgcgggcctcttcgctattacgccagctggcgaaagggggatgtgctgcaaggcgattaagttgggtaacgccag
ggttttcccagtcacgacgttgtaaaacgacggccagtgaattaggttaattaaggctgcgcgctcgctcgctcactgaggccgcccgggc
aaagcccgggcgtcgggcgacctttggtcgcccggcctcagtgagcgagcgagcgcgcagagagggagtggccaactccatcactag
gggttccttgtagttaatgattaacccgccatgctacttatctacgtagccatgctctaggaagatcctaatcgggaattctcaatattggccatta
gccatattattcattggttatatagcataaatcaatattggctattggccattgcatacgttgtatctatatcataatatgtacatttatattggctcatg
tccaatatgaccgccatgttggcattgattattgactagttattaatagtaatcaattacggggtcattagttcatagcccatatatggagttccgc
gttacataacttacggtaaatggcccgcctggctgaccgcccaacgacccccgcccattgacgtcaataatgacgtatgttcccatagtaac
gccaatagggactttccattgacgtcaatgggtggagtatttacggtaaactgcccacttggcagtacatcaagtgtatcatatgccaagtccg
cccccctattgacgtcaatgacggtaaatggcccgcctggcattatgcccagtacatgaccttacgggactttcctacttggcagtacatctacg
tattagtcatcgctattaccatggtgatgcggttttggcagtacaccaatgggcgtggatagcggtttgactcacggggatttccaagtctccac
cccattgacgtcaatgggagtttgttttggcaccaaaatcaacgggactttccaaaatgtcgtaacaactgcgatcgcccgccccgttgacgc
aaatggcggtaggcgtgtacggtgggaggtctatataagcagagctcgaattgtgagcgctcacaattgagctcgtttagtgaaccgtcag
atcactagaagctttattgcggtagtttatcacagttaaattgctaacgcagtcagtgcttctgacacaacagtctcgaacttaagctgcagtga
ctctcttaaggtagccttgcagaagttggtcgtgaggcactgggcaggtaagtatcaaggttacaagacaggtttaaggagaccaatagaaa
ctgggcttgtcgagacagagaagactcttgcgtttctgataggcacctattggtcttactgacatccactttgcctttctctccacaggtgtccac
tcccagttcaattacagctcttaaggctagagtacttaatacgactcactataggctagcctcagtaaaggagaagaacttttcactggagttgt

FIG. 5 (cont'd)

cccaattcttgttgaattagatggtgatgttaatgggcacaaattttctgtcagtggagagggtgaaggtgatgcaacatacggaaaacttacc
cttaaatttatttgcactactggaaaactacctgttccatggccaacacttgtcactactttcggttatggtctaaaatgctttgctagatacccaga
tcatatgaaacggcatgacttttcaagagtgccatgcccgaaggttatgtacaggaaagaactatatttttcaaagatgacgggaactacaag
acacgtgctgaagtcaagtttgaaggtgatacccttgttaatagaatcgagttaaaaggtattgattttaaagaagatggaaacattcttggaca
caaattggaatacaactataactcacacaatgtatacatcatggcagacaaacaaaagaatggaatcaaagttaacttcaaaattagacacaa
cattgaagatggaagcgttcaactagcagaccattatcaacaaaatactccaattggcgatggccctgtccttttaccagacaaccattacctg
tcctatcaatctgcccttcgaaagatcccaacgaaaagagagaccacatggtccttcttgagtttgtaacagctgctgggattacacatggca
tggatgaactatacaaagagaattcacgcgtcgagcatgcatctagggcggccaattccgcccctctccccccccccctctccctccccc
ccctaacgttactggccgaagccgcttggaataaggccggtgtgcgtttgtctatatgttattttccaccatattgccgtcttttggcaatgtga
gggcccggaaacctggccctgtcttcttgacgagcattcctagggggtctttcccctctcgccaaaggaatgcaaggtctgttgaatgtcgtga
aggaagcagttcctctggaagcttcttgaagacaaacaacgtctgtagcgaccctttgcaggcagcggaaccccccacctggcgacaggt
gcctctgcggccaaaagccacgtgtataagatacacctgcaaaggcggcacaaccccagtgccacgttgtgagttggatagttgtggaaa
gagtcaaatggctctcctcaagcgtattcaacaaggggctgaaggatgcccagaaggtacccccattgtatgggatctgatctggggcctcg
gtgcacatgctttacatgtgtttagtcgaggttaaaaaaacgtctaggccccccgaaccacgggggacgtggttttcctttgaaaaacacgatg
ataagcttgccacaacccgggatctatgaaaccagtaacgttatacgacgtcgcagagtatgccggtgtctcttatcagactgtttccagagtg
gtgaaccaggccagccatgtttctgccaaaaccagggaaaaagtggaagcagccatggcagagctgaattacattcccaacagagtggca
caacaactggcaggcaaacagagcttgctgattggagttgccacctccagtctggccctgcatgcaccatctcaaattgtggcagccattaa
atctagagctgatcaactgggagcctctgtggtggtgtcaatggtagaaagaagtggagttgaagcctgtaaagctgcagtgcacaatcttct
ggcacaaagagtcagtgggctgatcattaactatccactggatgaccaggatgccattgctgtggaagctgcctgcactaatgttccagcact
cttcttgatgtctctgaccagacacccatcaacagtattattttctcccatgaagatggtacaagactgggtgtggagcatctggttgcattggg
acaccagcaaattgcactgcttgcgggcccactcagttctgtctcagcaaggctgagactggccggctggcataaatatctcactaggaatc
aaattcagccaatagctgaaagagaaggggactggagtgccatgtctgggtttcaacaaaccatgcaaatgctgaatgagggcattgttccc
actgcaatgctggttgccaatgatcagatggcactgggtgcaatgagagccattactgagtctgggctgagagttggtgcagatatctcggta
gtgggatacgacgataccgaagacagctcatgttatatcccgccgttaaccaccatcaaacaggattttcgcctgctggggcaaaccagcgt
ggaccgcttgctgcaactctctcagggccaggcggtgaagggcaatcagctgttgccagtctcactggtgaagagaaaaaccaccctggc
acccaatacacaaactgcctctccccgggcattggctgattcactcatgcagctgggctcaggtctcgagttggtggtgagcaagggcgag
gaggataacatggccatcatcaaggagttcatgcgccttcaaggtgcacatggagggctccgtgaacggccacgagttcgagatcgagggc
gagggcgagggccgcccctacgagggcacccagaccgccaagctgaaggtgaccaaggggtggcccccctgcccttcgcctgggacatc
ctgtcccctcagttcatgtacggctccaaggcctacgtgaagcaccccgccgacatccccgactacttgaagctgtccttccccgagggctt
caagtgggagcgcgtgatgaacttcgaggacggcggcgtggtgaccgtgacccaggactcctccctgcaggacggcgagttcatctaca
aggtgaagctgcgcggcaccaacttcccctccgacggccccgtaatgcagaagaagaccatgggctgggaggcctcctccgagcggat
gtaccccgaggacggcgccctgaagggcgagatcaagcagaggctgaagctgaaggacggcggccactacgacgctgaggtcaaga
ccacctacaaggccaagaagcccgtgcagctgcccggcgcctacaacgtcaacatcaagttggacatcacctcccacaacgaggactac
accatcgtggaacagtacgaacgcgccgagggccgccactccaccggcggcatggacgagctgtacaaggcaagacaggtttccagac
tggaaagtgggcaggcagctctgcccaagaagaagcgaaaggtgtgatagagtcgacccgggcggccgcttccctttagtgagggttaat
gcttcgagcagacatgataagatacattgatgagtttggacaaaccacaactagaatgcagtgaaaaaaatgctttatttgtgaaatttgtgatg
ctattgctttatttgtaaccattataagctgcaataaacaagttaacaacaacaattgcattcattttatgtttcaggttcaggggggagatgtggga
ggttttaaagcaagtaaaacctctacaaatgtggtaaagaattccgatcttcctagagcatggctacgtagataagtagcatggcgggttaat
cattaactacaaggaacccctagtgatggagttggccactccctctgcgcgctcgctcgctcactgaggccgggcgaccaaaggtcgcc
cgacgcccgggctttgcccgggcggcctcagtgagcgagcgagcgcgcagccttaattaaatctggcgtaatcatggtcatagctgtttcct
gtgtgaaattgttatccgctcacaattccacacaacatacgagccggaagcataaagtgtaaagcctggggtgcctaatgagtgagctaact
cacattaattgcgttgcgctcactgcccgctttccagtcgggaaacctgtcgtgccagctgcattaatgaatcggccaacgcgcggggagag
gcggtttgcgtattgggcgct

FIG. 7

Nucleic acid sequence of plasmid p826 ggccgcagattacaaggatgacgatgacaagtaaagtactgacatgataagatacattgatgagtttggacaaaccacaactagaatgcagt
gaaaaaaatgctttatttgtgaaatttgtgatgctattgctttatttgtaaccattataagctgcaataaacaagttaacaacaacaattgcattcattt
tatgtttcaggttcaggggggagatgtggggaggtttttaaagcaagtaaaacctctacaaatgtggtaaactcgagttctacgtagataagtagc
atggcgggttaatcattaactacaaggaaccccctagtgatggagttggccactccctctctgcgcgctcgctcgctcactgaggccgggcga
ccaaaggtcgcccgacgcccgggctttgcccgggcggcctcagtgagcgagcgagcgcgcagccttaattaacctaaggaaaatgaagt
gaagttcctatactttctagagaataggaacttctatagtgagtcgaataagggcgacacaaaatttattctaaatgcataataaatactgataac
atcttatagtttgtattatattttgtattatcgttgacatgtataattttgatatcaaaaactgattttcccctttattatttcgagatttattttcttaattctctt
taacaaactagaaatattgtatatacaaaaaatcataaataatagatgaatagtttaattataggtgttcatcaatcgaaaaagcaacgtatcttatt
taaagtgcgttgctttttctcatttataaggttaaataattctcatatatcaagcaaagtgacaggcgcccttaaatattctgacaaatgctctttcc
ctaaactcccccataaaaaaacccgccgaagcgggttttttacgttatttgcggattaacgattactcgttatcagaaccgcccaggggccc
gagcttaaccttttatttgggggagagggaagtcatgaaaaaactaacctttgaaattcgatctccagcacatcagcaaaacgctattcacgc
agtacagcaaatccttccagacccaaccaaaccaatcgtagtaaccattcaggaacgcaaccgcagcttagaccaaaacaggaagctatg
ggcctgcttaggtgacgtctctcgtcaggttgaatggcatggtcgctggctggatgcagaaagctggaagtgtgtgtttaccgcagcattaaa
gcagcaggatgttgttcctaaccttgccgggaatggctttgtggtaataggccagtcaaccagcaggatgcgtgtaggcgaatttgcggagc
tattagagcttatacaggcattcggtacagagcgtggcgttaagtggtcagacgaagcgagactggctctggagtggaaagcgagatggg
gagacagggctgcatgataaatgtcgttagtttctccggtggcaggacgtcagcatatttgctctggctaatggagcaaaagcgacgggca
ggtaaagacgtgcattacgttttcatggatacaggttgtgaacatccaatgacatatcggtttgtcagggaagttgtgaagttctgggatatacc
gctcaccgtattgcaggttgatatcaacccggagcttggacagccaaatggttatacggtatgggaaccaaaggatattcagacgcgaatgc
ctgttctgaagccatttatcgatatggtaaagaaatatggcactccatacgtcggcggcgcgttctgcactgacagattaaaactcgttcccttc
accaaatactgtgatgaccatttcgggcgagggaattacaccacgtggattggcatcagagctgatgaaccgaagcggctaaagccaaag
cctggaatcagatatcttgctgaactgtcagactttgagaaggaagatatcctcgcatggtggaagcaacaaccattcgatttgcaaataccg
gaacatctcggtaactgcatattctgcattaaaaaatcaacgcaaaaaatcggacttgcctgcaaagatgaggagggattgcagcgtgttttta
atgaggtcatcacgggatcccatgtgcgtgacggacatcgggaaacgccaaaggagattatgtaccgaggaagaatgtcgctggacggta
tcgcgaaaatgtattcagaaaatgattatcaagccctgtatcaggacatggtacgagctaaaagattcgataccggctcttgttctgagtcatg
cgaaatatttggagggcagcttgatttcgacttcgggagggaagctgcatgatgcgatgttatcggtgcggtgaatgcaaagaagataaccg
cttccgaccaaatcaaccttactggaatcgatggtgtctccggtgtgaaagaacaccaacaggggtgttaccactaccgcaggaaaaggag
gacgtgtggcgagacagcgacgaagtatcaccgacataatctgcgaaaactgcaaataccttccaacgaaacgcaccagaaataaaccca
agccaatcccaaaagaatctgacgtaaaaaccttcaactacacggctcacctgtgggatatccggtggctaagacgtcgtgcgaggaaaac
aaggtgattgaccaaaatcgaagttacgaacaagaaagcgtcgagcgagctttaacgtgcgctaactgcggtcagaagctgcatgtgctgg
aagttcacgtgtgtgagcactgctgcgcagaactgatgagcgatccgaatagctcgatgcacgaggaagaagatgatggctaaaccagcg
cgaagacgatgtaaaaacgatgaatgccgggaatggtttcaccctgcattcgctaatcagtggtggtgctctccagagtgtggaaccaagat
agcactcgaacgacgaagtaaagaacgcgaaaaagcggaaaaagcagcagagaagaaacgacgacgagaggagcagaaacagaaa
gataaacttaagattcgaaaactcgccttaaagccccgcagttactggattaaacaagcccaacaagccgtaaacgccttcatcagagaaag
agaccgcgacttaccatgtatctcgtgcggaacgctcacgtctgctcagtgggatgccggacattaccggacaactgctgcggcacctcaa
ctccgatttaatgaacgcaatattcacaagcaatgcgtggtgtgcaaccagcacaaaagcggaaatctcgttccgtatcgcgtcgaactgatt
agccgcatcgggcaggaagcagtagacgaaatcgaatcaaaccataaccgccatcgctggactatcgaagagtgcaaggcgatcaagg
cagagtaccaacagaaactcaaagacctgcgaaatagcagaagtgaggccgcatgacgttctcagtaaaaaccattccagacatgctcgtt
gaagcatacggaaatcagacagaagtagcacgcagactgaaatgtagtcgcggtacggtcagaaaatacgttgatgataaagacgggaa
aatgcacgccatcgtcaacgacgttctcatggttcatcgcggatggagtgaaagagatgcgctattacgaaaaaattgatggcagcaaatac
cgaaatatttgggtagttggcgatctgcacggatgctacacgaacctgatgaacaaactggatacgattggattcgacaacaaaaaagacct
gcttatctcggtgggcgatttggttgatcgtggtgcagagaacgttgaatgcctggaattaatcacattcccctggttcagagctgtacgtgga
aaccatgagcaaatgatgattgatggcttatcagagcgtggaaacgttaatcactggctgcttaatggcggtggctggttctttaatctcgatta

FIG. 7 (cont'd)

cgacaaagaaattctggctaaagctcttgcccataaagcagatgaacttccgttaatcatcgaactggtgagcaaagataaaaaatatgttatc
tgccacgccgattatcccttgacgaatacgagtttggaaagccagttgatcatcagcaggtaatctggaaccgcgaacgaatcagcaactc
acaaaacgggatcgtgaaagaaatcaaaggcgcggacacgttcatctttggtcatacgccagcagtgaaaccactcaagtttgccaaccaa
atgtatatcgataccggcgcagtgttctgcggaaacctaacattgattcaggtacagggagaaggcgcatgagactcgaaagcgtagctaa
atttcattcgccaaaaagcccgatgatgagcgactcaccacgggccacggcttctgactctctttccggtactgatgtgatggctgctatggg
gatggcgcaatcacaagccggattcggtatggctgcattctgcggtaagcacgaactcagccagaacgacaaacaaaaggctatcaactat
ctgatgcaatttgcacacaaggtatcggggaaataccgtggtgtggcaaagcttgaaggaaatactaaggcaaaggtactgcaagtgctcg
caacattcgcttatgcggattattgccgtagtgccgcgacgccggggggcaagatgcagagattgccatggtacaggccgtgcggttgatatt
gccaaaacagagctgtgggggagagttgtcgagaaagagtgcggaagatgcaaaggcgtcggctattcaaggatgccagcaagcgcag
catatcgcgctgtgacgatgctaatcccaaaccttacccaacccacctggtcacgcactgttaagccgctgtatgacgctctggtggtgcaat
gccacaaagaagagtcaatcgcagacaacattttgaatgcggtcacacgttagcagcatgattgccacggatggcaacatattaacggcat
gatattgacttattgaataaaattgggtaaatttgactcaacgatgggttaattcgctcgttgtggtagtgagatgaaaagaggcggcgcttact
accgattccgcctagttggtcacttcgacgtatcgtctggaactccaaccatcgcaggcagagaggtctgcaaaatgcaatcccgaaacagt
tcgcaggtaatagttagagcctgcataacggtttcgggattttttatatctgcacaacaggtaagagcattgagtcgataatcgtgaagagtcg
gcgagcctggttagccagtgctctttccgttgtgctgaattaagcgaataccggaagcagaaccggatcaccaaatgcgtacaggcgtcatc
gccgcccagcaacagcacaacccaaactgagccgtagccactgtctgtcctgaattcattagtaatagttacgctgcggccttttacacatga
ccttcgtgaaagcgggtggcaggaggtcgcgctaacaacctcctgccgttttgcccgtgcatatcggtcacgaacaaatctgattactaaac
acagtagcctggatttgttctatcagtaatcgaccttattcctaattaaatagagcaaatcccttattggggtaagacatgaagatgccagaa
aaacatgacctgttggccgccattctcgcggcaaaggaacaaggcatcggggcaatccttgcgtttgcaatggcgtaccttcgcggcagat
ataatggcggtgcgtttacaaaaacagtaatcgacgcaacgatgtgcgccattatcgcctggttcattcgtgaccttctcgacttcgccggact
aagtagcaatctcgcttatataacgagcgtgtttatcggctacatcggtactgactcgattggttcgcttatcaaacgcttcgctgctaaaaaag
ccggagtagaagatggtagaaatcaataatcaacgtaaggcgttcctcgatatgctggcgtggtcggagggaactgataacggacgtcag
aaaaccagaaatcatggttatgacgtcattgtaggcggagagctatttactgattactccgatcaccctcgcaaacttgtcacgctaaacccaa
aactcaaatcaacaggcgcttaagactggccgtcgttttacaacacagaaagagtttgtagaaacgcaaaaaggccatccgtcaggggcct
tctgcttagtttgatgcctggcagttccctactctcgccttccgcttcctcgctcactgactcgctgcgctcggtcgttcggctgcggcgagcgg
tatcagctcactcaaaggcggtaatacggttatccacagaatcaggggataacgcaggaaagaacatgtgagcaaaaggccagcaaaag
gccaggaaccgtaaaaaggccgcgttgctggcgttttccataggctccgccccctgacgagcatcacaaaaatcgacgctcaagtcaga
ggtggcgaaacccgacaggactataaagataccaggcgtttccccctggaagctccctcgtgcgctctcctgttccgaccctgccgcttacc
ggatacctgtccgcctttctcccttcgggaagcgtggcgctttctcatagctcacgctgtaggtatctcagttcggtgtaggtcgttcgctccaa
gctgggctgtgtgcacgaaccccccgttcagcccgaccgctgcgccttatccggtaactatcgtcttgagtccaacccggtaagacacgact
tatcgccactggcagcagccactggtaacaggattagcagagcgaggtatgtaggcggtgctacagagttcttgaagtggtgggctaacta
cggctacactagaagaacagtatttggtatctgcgctctgctgaagccagttaccttcggaaaaagagttggtagctcttgatccggcaaaca
aaccaccgctggtagcggtggtttttttgtttgcaagcagcagattacgcgcagaaaaaaggatctcaagaagatcctttgatcttttctacgg
ggtctgacgctcagtggaacgacgcgcgcgtaactcacgttaagggattttggtcatgagcttgcgccgtcccgtcaagtcagcgtaatgct
ctgcttttagaaaaactcatcgagcatcaaatgaaactgcaatttattcatatcaggattatcaataccatattttgaaaagccgtttctgtaatg
aaggagaaaactcaccgaggcagttccataggatggcaagatcctggtatcggtctgcgattccgactcgtccaacatcaatacaacctatt
aatttccctcgtcaaaaataaggttatcaagtgagaaatcaccatgagtgacgactgaatccggtgagaatggcaaaagtttatgcatttcttt
ccagacttgttcaacaggccagccattacgctcgtcatcaaaatcactcgcatcaaccaaaccgttattcattcgtgattgcgcctgagcgag
gcgaaatacgcgatcgctgttaaaaggacaattacaaacaggaatcgagtgcaaccggcgcaggaacactgccagcgcatcaacaatatt
ttcacctgaatcaggatattcttctaatacctggaacgctgtttttccggggatcgcagtggtgagtaaccatgcatcatcaggagtacggataa
aatgcttgatggtcggaagtggcataaattccgtcagccagtttagtctgaccatctcatctgtaacatcattggcaacgctacctttgccatgtt
tcagaaacaactctggcgcatcgggcttcccatacaagcgatagattgtcgcacctgattgcccgacattatcgcgagcccatttatacccat
ataaatcagcatccatgttggaatttaatcgcggcctcgacgtttcccgttgaatatggctcatattcttccttttttcaatattattgaagcatttatca
gggttattgtctcatgagcggatacatatttgaatgtatttagaaaaataaacaaataggggttcagtgttacaaccaattaaccaattctgaacat
tatcgcgagcccatttatacctgaatatggctcataacacccccttgtttgcctggcggcagtagcgcggtggtcccacctgacccccatgccga
actcagaagtgaaacgccgtagcgccgatggtagtgtggggactccccatgcgagagtagggaactgccaggcatcaaataaaacgaaa

FIG. 7 (cont'd)

ggctcagtcgaaagactgggcctttcgcccgggctaattagggggtgtcgcccttattcgactctatagtgaagttcctattctctagaaagtat
aggaacttctgaagtggggtcgacttaattaaggctgcgcgctcgctcgctcactgaggccgcccgggcaaagcccggggcgtcgggcga
cctttggtcgcccggcctcagtgagcgagcgagcgcgcagagagggagtggccaactccatcactaggggttccttgtagttaatgattaa
cccgccatgctacttatctacgtagcaagctagcctagttattaatagtaatcaattacggggtcattagttcatagcccatatatggagttccgc
gttacataacttacggtaaatggcccgcctggctgaccgcccaacgaccccgcccattgacgtcaataatgacgtatgttcccatagtaac
gccaatagggactttccattgacgtcaatgggtggagtatttacggtaaactgcccacttggcagtacatcaagtgtatcatatgccaagtacg
cccccctattgacgtcaatgacggtaaatggcccgcctggcattatgcccagtacatgaccttatgggactttcctacttggcagtacatctacgt
attagtcatcgctattaccatggtgatgcggttttggcagtacaccaatgggcgtggatagcggtttgactcacggggatttccaagtctccac
cccattgacgtcaatgggagtttgttttggcaccaaaatcaacgggactttccaaaatgtcgtaacaactccgccccgttgacgcaaatgggc
ggtaggcgtgtacggtgggaggtctatataagcagagctcgaattgtgagcgctcacaattgaggtcgtttagtgaaccgtcagatcgttggt
cgtgaggcactgggcaggtaagtatcaaggttacaagacaaattgtgagcgctcacaattggtttaaggagaccaatagaaactgggcttgt
cgagacagagaagactcttgcgtttctgataggcacctattggtcttactgacatccactttgcctttctctccacaggtgtccactcccagttca
attacagatcaggcctaccatgaaaccagtaacgttatacgacgtcgcagagtatgccggtgtctcttatcagactgtttccagagtggtgaac
caggccagccatgtttctgccaaaaccaggaaaagtggaagcagccatggcagagctgaattacattcccaacagagtggcacaaca
actggcaggcaaacagagcttgctgattggagttgccaccctccagtctggccctgcatgcaccatctcaaattgtggcagccattaaatctag
agctgatcaactgggagcctctgtggtggtgtcaatggtagaaagaagtggagttgaagcctgtaaagctgccgtgcacaatcttctggcac
aaagagtcagtgggctgatcattaactatccactggatgaccaggatgccattgctgtggaagctgcctgcactaatgttccagcactctttctt
gatgtctctgaccagacacccatcaacagtattattttctcccatgaagatggtacaagactgggtgtggagcatctggttgcattgggacacc
agcaaattgcactgcttgcgggcccactcagttctgtctcagcaaggctgagactggccggctggcataaatatctcactaggaatcaaattc
agccaatagctgaaagagaaggggactggagtgccatgtctgggtttcaacaaaccatgcaaatgctgaatgagggcattgttcccactgc
aatgctggttgccaatgatcagatggcactgggtgcaatgagagccattactgagtctgggctgagagttggtgcagatatctcggtagtgg
gatacgacgataccgaagacagctcatgttatatcccgccgttaaccaccatcaaacaggattttcgcctgctggggcaaaccagcgtgga
ccgcttgctgcaactctctcagggccaggcggtgaagggcaatcagctgttgccagtctcactggtgaagagaaaaaccaccctggcacc
caatacacaaactgcctctccccgggcattggctgattcactcatgcagctgactagtgcacgacaggtttcccgactggaaagcgggcag
actagtgcaagacaggtttccagactggaaagtgggcaggcagctctgcccaagaagaagcgaaaggtgctgcagggaagcggagcta
ctaacttcagcctgctgaagcaggctggagacgtggaggagaaccctggacctagatctatggccagcaaaggagaagaacttttcactg
gagttgtcccaattcttgttgaattagatggtgatgttaatgggcacaaattttctgtcagtggagagggtgaaggtgatgctacatacggaaag
cttacccttaaatttatttgcactactggaaaactacctgttccatggccaacacttgtcactactttctcttatggtgttcaatgcttttcccgttatc
cggatcatatgaaacggcatgacttttcaagagtgccatgcccgaaggttatgtacaggaacgcactatatctttcaaagatgacgggaact
acaagacgcgtgctgaagtcaagtttgaaggtgataccettgttaatcgtatcgagttaaaaggtattgattttaaagaagatggaaacattctc
ggacacaaactcgagtacaactataactcacacaatgtatacatcacggcagacaaacaaaagaatggaatcaaagctaacttcaaaattcg
ccacaacattgaagatggatccgttcaactagcagaccattatcaacaaaatactccaattggcgatggccctgtccttttaccagacaaccat
tacctgtcgacacaatctgcccttcgaaagatcccaacgaaaagcgtgaccacatggtccttcttgagtttgtaactgctgctgggattacac
atggcatggatgagctctacaaagc

FIG. 14

Construct with Dual Switch

```
5' ITR          ctgcgcgctcgctcgctcactgaggccgcccgggcaaagcccgggcgtcgggcgacctttggtcgcccggcctcagt
1-130
                gagcgagcgagcgcgcagagagggagtggccaactccatcactaggggttccttgtagttaatgattaacccgccat gctacttatctacgtagcaagctagcctagttattaatagtaatcaattacggggtcattagttcatagcccatata tggagttccgcgttacataacttacggtaaatggcccgcctggctgaccgcccaacgaccccgcccattgacgtca ataatgacgtatgttcccatagtaacgccaataggactttccattgacgtcaatgggtggagtatttacggtaaac CMV
Enhancer        tgcccacttggcagtacatcaagtgtatcatatgccaagtacgccccctattgacgtcaatgacggtaaatggccc
181-647
                cctggcattatgcccagtacatgaccttatgggactttcctacttggcagtacatctacgtattagtcatcgctatt accatggtgatgcggttttggcagtacaccaatgggcgtggatagcggtttgactcacggggatttccaagtctcca LysM            ccccattgacgtcaatgggagtttgttttggaattgtgagcgctcacaattgacaccaaaatcaacggactttcca  CMV
648-667                                                                                                  Promoter
                aaatgtcgtaacaactccgccccgttgacgcaaatgggcggtaggcgtgtacggtgggaggtctatataagcagagc 670-819

LysM            tcgaattgtgagcgctcacaattgagctcgtttagtgaaccgtcagatcgttggtcgtgaggcactgggcaggtaag
774-793
                                                                                                        Intron
LysM            tatcaaggttacaagacaaattgtgagcgctcacaattggttttaaggagaccaatagaaactgggcttgtcgagaca 843-995
866-885
                gagaagactcttgcgtttctgataggcacctattggtcttactgacatccactttgcctttctctccacaggtgtcc actcccagttcaattacagatcaggcctatggtgaagcccgtgaccctgtacgacgtggccgaatatgccggcgtgt cctaccagaccgtgtcccgggtcgtgaatcaggccagccacgtgtccgccaagacccgcgaaaaagtggaagccgcc atggccgagctgaactacatccccaacagagtggcccagcagctggccggcaaacagtctctgctgatcggcgtggc cacaagcagcctggctctgcatgccccttctcagatcgtggccgccatcaagagcagagccgaccagctgggagcca gcgtggtggtgtctatggtggaacgctctggccgtggaagcctgcaaagccgccgtgcacaatctgctggcccagaga gtgtccggcctgatcatcaactaccccctgacgaccaggacgccattgccgtggaagctgcctgcaccaatgtgcc Lacl            cgccctgttcctggacgtgtccgatcagaccccatcaacagcatcatctggagccacgaggacgcaccggctgg
1027-2113
                gagtggaacatctggtggctctgggacaccagcagatcgccctgctggctggacctctgtcctccgtgtctgccaga ctgagactggccggctggcacaagtacctgacccggaaccagatccagcctatcgccgagagagagggcgattggag cgccatgtccggcttccagcagaccatgcagatgctgaacgagggcatcgtgcccaccgccatgctggtggccaatg accagatggcccctgggcgccatgagagccatcacagagtctggcctgagagtgggcgccgacatctccgtcgtgggc tacgacgataccgaggacagcagctgttacatcccccccctgaccaccatcaagcaggacttcagactgctgggaca gaccagcgtggaccggctgctacagctgtctcaggacaggccgtgaagggcaatcagctgctgcctgtgtccctcg tgaagagaaagaccaccctggccccaacacccagaccgcttctccaagagccctggccgacagcctgatgcagctg gctagacaggtgtcccggctggaaagcggacagactagtgcaagacaggtttccagactggaaagtgggcaggcagc P2A             tctgcccaagaagaagcgaaaggtgctgcagggaagcggagctactaacttcagcctgctgaagcaggctggagacg
2188-2253
```

FIG. 14 (cont'd)

tggaggagaaccctggacctagatctatggaagacgccaaaaacataaagaaaggcccggcgccattctattcactc gaagacgggaccgccggcgagcagctgcacaaagccatgaagcgctacgccctggtgcccggcaccatcgcctttac cgacgcacatatcgaggtggacattacctacgccgagtacttcgagatgagcgttcggctggcagaagctatgaagc gctatgggctgaatacaaaccatcggatcgtggtgtgcagcgagaatagcttgcagttcttcatgcccgtgttgggt gccctgttcatcggtgtggctgtggcccagctaacgacatctacaacgagcgcgagctgctgaacagcatgggcat cagccagcccaccgtcgtattcgtgagcaagaaagggctgcaaaagatcctcaacgtgcaaaagaagctaccgatca tacaaaagatcatcatcatggatagcaagaccgactaccagggcttccaaagcatgtacaccttcgtgacttccat ttgccaccggcttcaacgagtacgacttcgtgcccgagagcttcgaccgggacaaaaccatcgccctgatcatgaa Luciferase
2260-3909 cagtagtggcagtaccggattgcccaagggcgtagccctaccgcaccgcaccgcttgtgtccgattcagtcatgccc gcgaccccatcttcggcaaccagatcatccccgacaccgctatcctcagcgtggtgccatttcaccacggcttcggc atgttcaccacgctgggctacttgatctgcggctttcgggtcgtgctcatgtaccgcttcgaggaggagctattctt gcgcagcttgcaagactataagattcaatctgccctgctggtgcccacactatttagcttcttcgctaagagcactc tcatcgacaagtacgacctaagcaacttgcacgagatcgccagcggcgggcgccgctcagcaaggaggtaggtgag gccgtggccaaacgcttccacctaccaggcatccgccagggctacggcctgacagaaacaaccagcgccattctgat caccccgaaggggacgacaagcctggcgcagtaggcaaggtggtgcccttcttcgaggctaaggtggtggacttgg acaccggtaagacactggctgtgaaccagcgcggcgagctgtgcgtccgtggccccatgatcatgagcggctacgtt aacaaccccgaggctacaaacgctctcatcgacaaggacggctggctgcacagcggcgacatcgcctactgggacga ggacgagcacttcttcatcgtggaccggctgaagagcctgatcaaatacaagggctaccaggtagccccagccgaac tggagagcatcctgctgcaacaccccaacatcttcgacgccggggtcgccggcctgcccgacgacgatgccggcgag ctgcccgccgcagtcgtcctgctggaacacggtaaaaccatgaccgagaaggagatcgtggactatgtggccagcca ggttacaaccgccaagaagctgcgcggtggtgttgtgttcgtggacgaggtgcctaaaggactgaccggcaagttgg acgccgcaagatcgcgagatcctcataaaggccaagaagggcggaaagatcgccgtggcggccgcagattacaag gatgacgatgacaagtaagtttaaaccaaacaaacaaaggcgcgtcctggattcgtgcaaaaacataccagatttcg K7
Aptazyme  atctggagaggtgaagaatacgaccaccttgtacatccagctgatgagtcccaaataggacgaaacgcgctcaaaca
3943-4090 aacaaaagtacttaagacatgataagatacattgatgagtttggacaaaccacaactagaatgcagtgaaaaaaatg

SV40
polyA     ctttatttgtgaaatttgtgatgctattgctttatttgtaaccattataagctgcaataaacaagttaacaacaaca
4097-4318 attgcattcatttatgttcaggttcagggggagatgtgggaggtttttaaagcaagtaaaacctctacaaatgt ggtaaactcgagttctacgtagataagtagcatggcgggttaatcattaactacaaggaacccctagtgatggagtt

FIG. 14 (cont'd)

3' ITR
4368-4497   ggccactccctctctgcgcgctcgctcgctcactgaggccgggcgaccaaaggtcgcccgacgcccgggctttgccc
            gggcggcctcagtgagcgagcgagcgcgcag

COMPOSITIONS AND METHODS FOR SELF-REGULATED INDUCIBLE GENE EXPRESSION

CROSS-REFERENCE TO RELATED APPLICATIONS

This application is a national stage of International Patent Application No. PCT/US2015/043335, filed Jul. 31, 2015, which claims the benefit of the priorities of U.S. Provisional Patent Application No. 62/159,797, filed May 11, 2015 and U.S. Provisional Patent Application No. 62/032,449, filed Aug. 1, 2014. The priority applications are incorporated herein by reference.

STATEMENT REGARDING FEDERALLY SPONSORED RESEARCH OR DEVELOPMENT

This invention was made with government support under Grant Nos. R24EY019861, 1F30AG044078-01A1 and 8DP1EY023177 awarded by the National Institutes of Health. The government has certain rights in this invention.

SEQUENCE LISTING

Applicant hereby incorporates by reference the Sequence Listing material filed in electronic form herewith. This file is labeled "UPN-Y6194PCT_ST25.txt".

BACKGROUND OF THE INVENTION

Gene therapy is a powerful tool that is being used to combat inherited and acquired disease. The ability to introduce transgenes into a cell and restore normal physiology holds the future for ameliorating a variety of inherited and acquired errors in metabolism. Currently, there are roughly 1800 ongoing clinical trials where the transgene is constitutively expressed, using either ubiquitous or tissue-specific promoters. However, for most inherited or acquired disorders the transgene must be tightly regulated and/or titrated with disease progression. An additional major concern is that constitutive transgene expression can be toxic, producing undesirable side effects and even death. For safe and effective protein delivery, the transgene must be appropriately regulated.

The field of gene therapy has seen many significant advances over the past decade[3]. Viral vectors are available that can effectively express heterologous genes in vivo and provide long-term gene expression to target tissues with minimal toxicity and immune response. One of the most successful applications of this technology has been the restoration of vision for individuals with the retinal degenerative disorder described as Leber's congenital amaurosis (LCA)[4,5]. Currently there are approximately 1800 ongoing human gene therapy clinical trials that use similar gene replacement therapies; however, for many pathological conditions gene augmentation therapies need to be regulated[1]. Indeed, gene regulation remains one of the most important and unresolved obstacles for safe and effective development of clinical gene therapeutics.

Most transgene regulatory systems are based upon the classical bacterial operons, where a regulating protein is constitutively produced by one promoter to modulate transcription of a second promoter expressing a functional gene[6]. A variety of such inducible regulatory systems have been developed utilizing a number of different regulatory proteins. These regulatory proteins are allosterically controlled by effector molecules such as the antibiotic tetracycline (Tet), steroid hormones (ecdysone), anti-steroid hormone analogs (mifepristone and tamoxifen), and immunosuppressant (rapamycin)[6]. Regardless of how the regulator is controlled, the fundamental problems that have plagued all of these regulatory systems is that effector molecules can produce unwanted side effects, the regulatory circuitry exhibits a high basal level of gene expression with only a modest dynamic range, and many of these systems are too large to easily fit within the packaging constraints of a single viral vector such as a recombinant adeno-associated virus (rAAV). Additionally, the level of regulator protein produced in these systems is constant and dependent on a number of extrinsic variables, such that the system will behave differently in different environments. The resulting switch must be empirically tuned for each particular application to ensure sufficient dynamic range and to minimize leakiness of transgene expression in the uninduced state.

As a consequence there is tremendous interest in developing expression systems in which the dosages of therapeutic transgenes are readily and easily regulated. Transgene regulation has the potential to modulate, stop, and/or resume transgene expression in response to disease evolution. A number of inducible systems have been developed to control transgene expression in mammalian cells.

For example, one inducible activation system for regulating transgene expression in eukaryotic cells was created by fusing the Tet repressor with an activation domain, VP16, from Herpes Simplex Virus. This fusion protein binds to the tetracycline response elements (TREs) located within an inducible promoter, activating transcription either in the presence or the absence of inducer. The two systems, "Tet-On" and "Tet-Off" both activate expression but respond to doxycycline (Dox) differently; Tet-Off activates expression in the absence of Dox, whereas Tet-On activates in the presence of Dox. Another commonly used switch to regulate transcription relies on rapamycin, an immunosuppressant. Analogous to the Tet-On system, rapamycin mediates heterodimer formation between two proteins; FKBP and FRB; where FKBP is fused to a zinc finger homeodomain and FRB to an activation domain. Transcription is activated by recruiting the activation domain to the promoter that is mediated by rapamycin facilitated dimerization of FKBP and FRP.

These known inducible systems require delivery of multiple components, thereby increasing the potential for immunologic complications. For both tetracycline and rapamycin, repeated administration can lead to toxic (and sometimes life-threatening) side effects. Existing inducible systems also suffer wide variations in expression levels that increase the risk of adverse effects in the host organism and confound scientific experimentation.

SUMMARY OF THE INVENTION

The invention described herein fulfills a need in the art by providing self-regulating gene expression switches used to regulate transgene expression, particularly in a virus vector or recombinant virus. This switch is inducible with drug-like agents or ligands which activate transcription rather than silence it. This self-regulating expression system thus ensures that the transgene is produced only when needed. A more robust inducible transgene regulatory system is provided by layering two regulatory systems to control both the synthesis and the degradation of messenger RNA.

In one aspect a heterologous self-regulating gene expression cassette or construct comprises, in operative association, a single promoter controlling expression of a repressor sequence and a transgene; one or more operator sequences responsive to the expressed repressor protein; the repressor gene sequence, an internal ribosome entry site (IRES) sequence or a 2A sequence; and a selected transgene sequence. This cassette is designed in one embodiment for use in a recombinant vector, preferably a viral vector, such as an adeno-associated virus (AAV). In certain embodiments, the repressor sequences are bacterial repressor sequences such as lacI or galR.

In another aspect, a dual self-regulating inducible gene expression construct or cassette comprises, in operative association, a single promoter controlling expression of a bacterial repressor sequence and a transgene, and which, in the presence of a first inducer molecule, transcribes the transgene and repressor. These elements of the dual self-regulating construct can be similar to those of the immediately preceding cassette or constsruct. The dual construct also contains a ribozyme in association with an aptamer sequence, the aptamer sequence capable of interacting with a second inducer molecule to terminate mRNA degradation by the ribozyme. When operative in a cell, this construct transcribes the transgene in the presence of the first inducer molecule and second inducer molecule, and, in the absence of the first inducer molecule and second inducer molecule, transcription is terminated. In certain embodiments, the first inducer molecule and second inducer molecule are the same molecule.

In another aspect, a recombinant vector is provided that comprises one of the self-regulating or dual self-regulating constructs or cassettes. The vector can be a virus, such as an AAV, or a non-viral vector. The constructs are particularly suited for easy inclusion into the rAAV due to the size of the constructs.

In yet another aspect, a recombinant cell is provided that comprises one of these vectors and is characterized by tight regulation of transgene expression.

In another aspect, a method of producing a recombinant adeno-associated virus or other viral vector containing a heterologous self-regulating gene cassette is provided.

In another aspect, a method of controlling expression of a transgene in a mammalian cell comprises infecting the cell with a recombinant virus or vector comprising the heterologous self-regulating expression cassettes or constructs, wherein the gene cassette is stably expressed by the infected cell. The method includes inducing expression of a specific amount of transgene in the cell by contacting the cell in vivo with a first inducing molecule that interacts with the repressor to permit simultaneous expression of the transgene and repressor protein by the single promoter. The repressor protein is then expressed along with the transgene. The repressor protein autoregulates transgene expression by interacting with the operator sequence as the repressor protein accumulates in the cells turning off further expression of both the repressor protein and the transgene. Thus, the amount of transgene expressed is regulated. When the method employs infecting the cells with the dual regulating cassette or construct, the additional use and presence of a second inducing molecule that interacts with the ribozyme-aptamer shuts off the ribozymes ability to degrade the mRNA transcript. When the second inducer is removed, generally, simultaneously with removal of the first inducing the ribozyme functions to degrade any residual mRNA and provides a second mechanism to that of the repressor-operator function to tightly shut off transgene expression.

In another aspect, a method of treating an ocular condition comprises administering, e.g., by intravitreal or subretinal injection, to a mammalian subject in need thereof a recombinant virus comprising the heterologous self-regulating expression cassette. The gene cassette in the virus becomes stably expressed in the subject's ocular cells. The course and amount of expression of the transgene in the ocular cell is controlled by subsequently and/or repeatedly administering to the subject, a first inducing molecule that interacts with the repressor sequence to permit simultaneous expression of the transgene and repressor protein by the single promoter. In the absence of additional amounts of the molecule, the repressor protein expressed in the cell auto-regulates and reduces or inhibits its own further expression. Similarly use of the dual regulating construct and second inducing molecule in this method adds tighter regulation and reduces any "leakiness" of the self-regulating expression cassettes.

These and other embodiments and advantages of the invention are described in more detail below.

BRIEF DESCRIPTION OF THE DRAWINGS

FIG. 2A are XENOGEN imaging pictures revealing regulatable induction of luciferase in the AAV-injected eye of a mouse only after IPTG is administered. The left eye of each mouse served as an uninjected, negative control. The pictures were taken at the indicated times. FIG. 2B is a graph showing quantification of luciferase levels before and after induction.

FIG. 3A shows XENOGEN imaging revealing externally regulatable induction of luciferase in the liver after IPTG is administered. FIG. 3B is a bar graph showing quantification of luciferase levels before and after induction.

FIG. 5 is the nucleic acid sequence of p794 SEQ ID NO: 1.

FIG. 7 is the nucleic acid sequence of p826 SEQ ID NO: 2.

FIG. 14 is the nucleotide sequence encoding the construct of FIG. 11.

DETAILED DESCRIPTION OF THE INVENTION

Figure 1A:
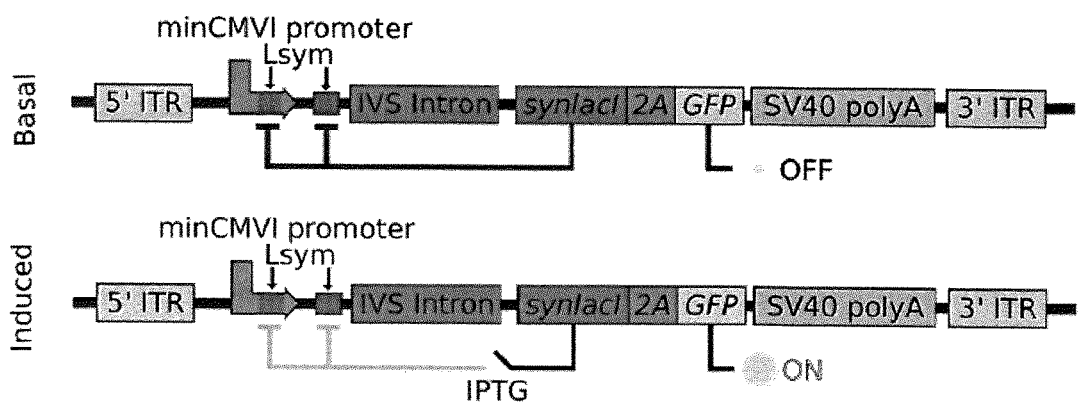
FIG. 1A is a map of the design of an autogenous regulatory cassette in the basal (top panel) and induced (lower panel) states. The cassette includes the minimal CMV with a symmetric lac operator (Lsym) between the TATA box and the transcription start site and a second Lsym placed 92 base pairs downstream in order to facilitate cooperative binding of the lac repressor tetramer.

Self-regulating gene switches and transgene expression cassettes and constructs, as well as vectors and cells containing them, are provided for use in auto-regulating the expression of a transgene in a cell. Also provided herein is an adeno-associated virus (AAV) vector which reversibly regulates a transgene using an autogenously regulated lac repressor. These regulatory system addresses several key areas for gene therapeutic regulation applications: they allow reversible regulation of a transgene delivered by an AAV vector. The expression constructs responds to an otherwise inert effector, and the system can be easily augmented to target it for specific applications. Autogenous regulation derived from the LacI/GalR family in AAV vectors can provide safe, effective regulation and has application in human gene therapy.

In one embodiment, a self-regulating inducible gene expression construct comprises in operative association, as a first level of regulation, the regulation created by use of a repressor sequence. The expression construct comprises a single promoter controlling expression of a bacterial repressor sequence and a transgene, and which, in the presence of a first inducer molecule, transcribes the transgene and repressor. The repressing regulator binds DNA close to or within a promoter and blocks access of RNA polymerase for the promoter. Binding of the repressor to its operator effectively decreases gene expression by preventing polymerase access to the promoter[7]. When the cassette is present in, and delivered by a vector, e.g., a recombinant virus, it can be readily employed to express the transgene in a selected amount and in a selected time course In contrast to the operation of the lactose operon of *Escherichia coli*, in which transcription of the operon is positively activated by a cyclic AMP-dependent catabolite gene regulator protein (CAP) and negatively regulated by a constitutively expressed lacI repressor, the present expression system provides an autogenously regulated gene switch. In the embodiments described herein, the repressor is not constitutively expressed, but is auto-regulated by negative feedback. Polymerase transcribes both the transgene and regulator genes from the promoter that is itself regulated. The newly synthesized repressor, when bound to the promoter, prevents transcription of both the transgene and itself.

In another embodiment, a dual self-regulating inducible gene expression construct comprises the single promoter controlling expression of a bacterial repressor sequence and a transgene, and which, in the presence of a first inducer molecule, transcribes the transgene and repressor; and further comprises a ribozyme in association with an aptamer sequence. The aptamer sequence is capable of interacting with a second inducer molecule to terminate mRNA degradation by the ribozyme. When operative in a cell, the construct transcribes the transgene in the presence of the first inducer molecule and second inducer molecule, and, in the absence of the first inducer molecule and second inducer molecule, transcription is terminated.

As exemplified below, autogenous regulation of a reporter gene is demonstrated using the gene switch in *Escherichia coli*, eukaryotic cells in vitro, and both the retina and the liver of living mice. This autogenously regulated system has several attributes that are attractive for in vivo transgene regulation. The response to effector is linearized creating a more rheostat-like switching behavior; the response of the regulator to effector is faster than constitutive regulation; and the response of regulation to changes in the environment is buffered due to an increase in stability. Furthermore, autogenous regulation maintains the minimum necessary intracellular concentration of the regulator that is necessary thus reducing the potential of an immune response to the regulator protein. Relatedly, the stability of autogenously regulated system is independent of changes in cell size or growth rate. Thus, autogenous regulation provides the cell with a means of accomplishing a number of different regulatory tasks and is an ideal regulatory circuit for controlling a transgene in mammalian cells.

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. The following definitions are provided for clarity only and are not intended to limit the claimed invention.

The terms "a" or "an" refers to one or more, for example, "a subject" is understood to represent one or more such subjects. As such, the terms "a" (or "an"), "one or more," and "at least one" are used interchangeably herein. As used herein, the term "about" means a variability of 10% from the reference given, unless otherwise specified.

Throughout this specification, the words "comprise", "comprises", and "comprising" are to be interpreted to include components in addition to those identified. The words "consist", "consisting", and its variants, are to be interpreted exclusively, i.e., to exclude significant components other than those specifically identified. It should be understood that while various embodiments in the specification are presented using "comprising" language, under various circumstances, a related embodiment is also be described using "consisting of" or "consisting essentially of" language.

As used herein, the term "mammalian subject" or "subject" includes any mammal in need of these methods of treatment, including particularly humans. Other mammals in need of such treatment or prophylaxis include dogs, cats, or other domesticated animals, horses, livestock, laboratory animals, including non-human primates, etc. The subject may be male or female.

As used herein, when referring to a range, any number included within the range of values, including the endpoints, are interpreted to be included.

By "natural or wildtype lacI repressor" is meant the lactose operon repressor of *E. coli*, strain K12. The 360 amino acid sequence of lacI is found at UniProtKB/Swiss-Prot accession number P03023 SEQ ID NO: 3. The mutations of lacI referred to herein correspond to the amino acid numbers in the 360 amino acid sequence of SEQ ID NO: 3. This term may also refer to lactose operon repressors of other bacterial strains.

By "natural or wildtype galR repressor" is mean the galactose operon repressor of *E. coli*, strain K12, the amino acid sequence of which is located UniProtKB/Swiss-Prot accession number P03024 SEQ ID NO: 4. This term may also refer to galactose operon repressors of other bacterial strains.

"Autogenous" or "self-regulating" as the term is used herein is meant in one embodiment to indicate that the repressor of the gene expression cassette controls its own transcription through its interaction with a functional operator. In another embodiment, these terms refer to the dual regulatory constructs with also employ a ribozyme-coupled aptamer to introduce the additional ability of the construct to tightly regulate mRNA degradation with the transcription regulation of the repressor.

By the cassette references "synlacI" or "EuLacTet" is meant to refer to a cassette that employs the lacI sequence with some codon optimization, a splice site removed, and a nuclear localization sequence positioned N-terminally. See e.g., Cronin[15,30], cited herein and Scrable[29], cited herein. SEQ ID NO: 13.

By the cassette reference "EuLac" is meant to refer to a cassette that employs synlacI with codons for lacI amino acids 349-360 of SEQ ID NO: 3 removed.

By "first inducing molecule" as used herein is meant an effector molecule, usually a small chemical molecule that interacts with the repressor sequence so as to prevent it from binding to its operator(s) and permitting transcription to occur from the promoter. In the absence of the first inducing molecule, the repressor of the construct binds to its operators and shuts down transcription of both itself and the transgene. The first inducing molecule functions in both embodiments of the self-regulating constructs described herein. In one embodiment, the first inducing molecule is isopropyl β-D-1-thiogalactopyranoside (IPTG). Other molecules that interact with the selected repressors used in these constructs may function as first inducing molecules.

By "second inducing molecule" as used herein is meant a small chemical molecule or drug that interacts with the aptamer coupled to the ribozyme in the construct and prevents the ribozyme from self-cleaving. In the absence of the second inducing molecule, the ribozyme in the construct which is located upstream of the polyA site cleaves itself and thus degrades any remaining mRNA transcribed from the promoter. In some circumstances, the second inducing molecule may be the same molecule as the first inducing molecule and thus both interact with the repressor and with the aptamer of the dual regulatory constructs described herein. In one embodiment, the second inducing molecule is tetracycline. Other molecules that are bound by aptamers designed to interact with them may be used as second inducing molecules, including IPTG.

In one embodiment, the self-regulating inducible gene expression construct or "switch" disclosed herein can regulate the amount of the transgene and control such regulation by the affinity between the repressor and its operator. This first level of regulation controls the synthesis of mRNA, which is controlled by transcriptional regulators. The repressor attenuate transcription by interfering with polymerase binding. Binding of the repressor to an operator downstream of the promoter, physically blocks polymerase from binding to the promoter. The repressor is allosterically regulated such that in the absence of effector molecules (e.g., first inducing molecule), the repressor binds to its operator and decreases the probability that polymerase binding to the promoter. In the presence of the first inducing molecule, the repressor no longer can bind to its operator, allowing polymerase to bind to the promoter. This gene expression system maintains a low level of basal expression of the transgene; and exhibits functional levels of transgene upon induction. It has an inducing dynamic range that provides useful dose response control, i.e. the system resembles rheostat as opposed to an on-off switch. The gene switch is dynamic and responds quickly to changes in the effector concentration. It responds to effector molecules (e.g., first inducing molecule) that are orally active small molecule with no effect on endogenous gene expression and minimal toxicity. It minimizes potential immunogenicity. Additionally, this gene expression system is useful for delivery of a transgene by, among others, an adeno associated virus (AAV), because it is compact and can fit with a transgene into the AAV viral capsid.

In another embodiment, the dual self-regulating inducible gene expression construct or "switch" further includes a second level of regulation that controls the degradation of mRNA. As described in more detail in Example 8, the rate of the degradation of m RNA effects the production of the transgene. By using an inducible hammerhead ribozyme that that cleaves itself in the absence of an effector molecule (i.e., second inducing molecule) placed upstream of a polyA tail, the degradation of the mRNA becomes inducible. The dual construct combines control of transcription and control of mRNA degration, thereby creating a novel and less leaky transgene regulatory system with an enhanced dynamic range.

In one embodiment, the heterologous self-regulating gene expression cassette or construct comprises, in operative association: a single promoter controlling expression of a repressor sequence and a transgene; one or more operator sequences responsive to the expressed repressor protein; the repressor gene sequence; an internal ribosome entry site (IRES) sequence or a 2A sequence that allows for multiple genes transcribed under one promoter; and the selected transgene sequence.

In another embodiment, a dual construct contains, in operative association, a single promoter controlling expression of a bacterial repressor sequence and a transgene; one or more operator sequences responsive to the expressed repressor protein; the repressor gene sequence, said repressor sequence capable of interacting with a first inducer molecule and thereby initiating transcription by the promoter; a 2A sequence; a selected transgene sequence; and a ribozyme in association with an aptamer sequence, said aptamer sequence capable of interacting with a second inducer molecule, and thereby prevent degradation of the transcription, positioned upstream of a polyadenylation sequence.

In one embodiment, the components of any of the constructs or cassettes described herein are in the order 5' to 3': Promoter-Operator(s)-Repressor-2A or IRES-Transgene. In another embodiment, the components of any of the constructs or cassettes described herein are in the order 5' to 3': Promoter-Operator(s)-Transgene-2A or IRES-Repressor. In another embodiment, the order of components includes the ribozyme-aptamer sequence, located in a position that does not disrupt transcription of the transgene or functioning of the other components of the construct, but is always upstream of the polyA sequences of the constructs.

These self-regulating control constructs each have an inducible promoter to regulate the expression of the repressor as well as the transgene. Since the repressor regulates its own synthesis, it precisely controls the amount of a reporter gene or transgene that is delivered. A self-regulating switch is extremely useful in the design of inducible vectors for gene therapy. For example, in one embodiment, the inducible self-regulating gene delivery system that is driven from a single promoter saves space within the vector, which is particularly important with viral delivery of therapeutic genes. In another embodiment, the therapeutic gene under control of the self-regulated inducible expression system can be constitutively maintained at a suitable level by altering the affinity between the repressor and the operator. Additionally, the use of a single promoter controlling the transcription of two genes provides an additional safeguard that the therapeutic transgene is less likely to reach toxic levels or stimulate an immune response.

In the constructs described herein, the amount of transcript produced can be precisely defined by having a repressor regulate its own synthesis. Using this system, one can pharmacologically set the level of expression in a manner that is independent of dose and promoter strength and is customized for a particular therapeutic. Dose and promoter are important for determining the lower and upper limits of the system. The levels of the expressed gene and the repressor depend upon the binding affinity of the repressor to its operator and can easily be tailored to a particular application. This system requires the presence of a first inducing molecule or drug to cause the repressor to be removed from the operator, thereby inducing the promoter to direct expression of both the repressor protein and the transgene. One advantage of this system is that there is a maximum amount of the inducing drug required to displace the repressor from the operator and additional quantities of drug are not effective. This permits a limited amount of inducer to be used to trigger expression of a specific amount of transgene, before the accumulating repressor protein again interacts with its operator and effectively turns off expression of itself and the transgene. Thus toxicity of the inducing molecule is controlled. Moreover, since transgene expression is inducible, a bolus of the transgene can be delivered when warranted. Additionally in the dual construct, as stated, the regulation of the mRNA degradation by the ribozyme-aptamer sequence in response to the second inducing molecule provides an advantage by reducing leakiness of the constructs.

More precisely, the elements of the autonomous gene expression constructs are as follows. It is understood that all components or elements of these constructs may be codon optimized for expression in specified cells, e.g., human cells.

The Single Promoter

The single promoter in the construct or cassette may be selected from a variety of known and useful promoters. In one embodiment, as exemplified in the plasmids p794 and p826, the promoter is a cytomegalovirus (CMV) promoter or minimal CMV promoter. In another embodiment, the promoter may be a chicken β-actin (CBA) promoter. Still another useful promoter is the immediate early CMV enhancer coupled with the CBA promoter. Other useful promoters may be one of the promoters for arrestin, rhodopsin kinase, EF1 or EF1α, mGluR6, tyrosine kinase, BEST1, GFAP, or GRK1. In one embodiment, promoter is the native promoter for the gene to be expressed. Useful promoters include, without limitation, the rod opsin promoter, the red-green opsin promoter (and/or modified red-green opsin), the blue opsin promoter, the cGMP-β-phosphodiesterase promoter, the mouse opsin promoter, the rhodopsin promoter; the alpha-subunit of cone transducin; beta phosphodiesterase (PDE) promoter; the retinitis pigmentosa (RP1) promoter; the NXNL2/NXNL1 promoter, the RPE65 promoter; the retinal degeneration slow/peripherin 2 (Rds/perph2) promoter; and the VMD2 promoter. Each of these promoters is publicly available or described in publications available to those of skill in the art.

Other useful promoters include transcription factor promoters including, without limitation, promoters for the neural retina leucine zipper (Nrl), photoreceptor-specific nuclear receptor Nr2e3, and basic-leucine zipper (bZIP). In one embodiment, the promoter is of a small size, under 1000 bp. This small size of promoter is suitable to meet the size limitations of the AAV vector. In another embodiment, the promoter is under 400 bp.

Still other promoters useful herein include ubiquitous or constitutive promoters, when universal expression of the transgene is desired. In one embodiment, the promoter is selected from the phosphoglycerate kinase-1 (PGK) promoter. Other examples of constitutive promoters useful herein include, without limitation, the retroviral Rous sarcoma virus (RSV) LTR promoter (optionally with the RSV enhancer), the SV40 promoter, or the dihydrofolate reductase promoter.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. In one embodiment, the inducible promoter is selected from rapamycin/rapalog promoter, the ecdysone promoter, the estrogen-responsive promoter, and the tetracycline-responsive promoter. Examples of other inducible promoters regulated by exogenously supplied compounds which are useful herein, include, the zinc-inducible sheep metallothionine (MT) promoter, the dexamethasone (Dex)-inducible mouse mammary tumor virus (MMTV) promoter, the T7 polymerase promoter system. Other types of inducible promoters which may be useful in this context are those which are regulated by a specific physiological state, e.g., temperature, acute phase, a particular differentiation state of the cell, or in replicating cells only. In one embodiment, any type of inducible promoter which is tightly regulated and is specific for the particular target ocular cell type may be used.

One of skill in the art has ready access to the sequences and public sources of these selected promoter sequences. Examples of useful promoters are also demonstrated by the promoters used in the examples below.

The Repressor Sequence

As described herein, a number of repressor sequences may be used in the self-regulating gene expression constructs or cassettes designed herein. However, these constructs are exemplified with a bacterial repressor sequence. For example, the combination of the bacterial lacI or galR repressor/operator genetic switch with an autogenous switch organization addresses the requirements of an ideal, inducible transgene regulator for AAV-mediated gene therapy.

In one embodiment, the repressor gene is lacI In one embodiment, the lacI repressor has the wildtype protein sequence UniProtKB: P03023 SEQ ID NO: 3, encoded by a suitable nucleic acid sequence. In one embodiment, the nucleic acid sequence is, e.g., GenBank Gene ID: 945007 (also NCBI NC000913.3) SEQ ID NO: 5. In the embodiments that follow, all amino acids residues refer to SEQ ID NO: 3. In another embodiment, the lacI repressor contains a mutation at lacI repressor protein residue 18 from Q to A, and the gene contains a suitable mutation to effect this change. In another embodiment, the lacI repressor contains a mutation at lacI repressor protein residue 18 from Q to M, and the gene contains a suitable mutation to effect this change. In another embodiment, the lacI repressor contains a mutation at lacI repressor protein residue 161 from F to S, and the gene contains a suitable mutation to effect this change. In another embodiment, the lacI repressor contains a mutation at lacI repressor protein residue 161 from F to W, and the gene contains a suitable mutation to effect this change. In another embodiment, the lacI repressor contains a mutation at lacI repressor protein residue 161 from F to T, and the gene contains a suitable mutation to effect this change. In another embodiment, the lacI repressor contains a mutation at lacI repressor protein residue 291 from Q to K, and the gene contains a suitable mutation to effect this change. In another embodiment, the lacI repressor contains a mutation at lacI repressor protein residue 291 from Q to M, and the gene contains a suitable mutation to effect this change. In another embodiment, the lacI repressor contains a mutation at lacI repressor protein residue 17 from Y to H, and the gene contains a suitable mutation to effect this change. In another embodiment, the lacI repressor contains a mutation at lacI repressor protein residue 148 from L to D, and the gene contains a suitable mutation to effect this change. In another embodiment, the lacI repressor contains a mutation at lacI repressor protein residue 148 from L to W, and the gene contains a suitable mutation to effect this change.

In one embodiment, the repressor is a tetrameric lacI repressor. In another embodiment, the repressor is a dimeric lacI repressor. In one embodiment, the repressor sequence comprises a dimeric lacI repressor sequence which lacks the 11 C terminal residues of the lacI repressor (aa 350-360 of SEQ ID NO: 3). In another embodiment, the repressor is a tetrameric lacI repressor.

In another embodiment, the repressor sequence is the bacterial galR repressor, about which numerous publications are available.

In another embodiment, the repressor sequence is the bacterial tetR repressor. See, e.g., Baron U, Bujard H. 2000 *Methods Enzymol* 327: 401-21; and Schonig, K, Bujard H. 2003. In: *Transgenic Mouse Methods and Protocols*, Hofker, M, van Deursen, J (eds.) Humana Press, Totowa, N.J., pp. 69-104, incorporated herein by reference.

Particularly useful are repressor sequences that interact with an inducing molecule to which an aptamer is designed for use coupled to a ribozyme in the dual regulatory construct described herein. Still other repressor sequences are anticipated to be similarly useful in place of the exemplified bacterial repressors following the instructions of this specification. For other repressors, see, e.g., Zoltick P W, Wilson J M, December 2001, Ann. NY Acad. Sci., 953:53-63, incorporated by reference herein, among other publications.

Operator Sequences

Operator sequences used in the constructs described herein include the naturally occurring operator sequences associated with the selected repressor protein. Such sequences are known in the art. The natural lacI operon includes three operators: O1 which is located within the promoter, O2 which is 401 base pairs downstream of O1, and O3 which is 92 base pairs upstream of O1. The operators are all pseudo-palindromic and have similar, yet distinct sequences and different affinities for the lac repressor. In one embodiment, the operator is a fully symmetric operator that was created by copying the left half of the O1 operator and removing the central G base, i.e., the Lsym operator (Sadler, Sasmor, & Betzt, 1983). The sequences of four exemplary operators are:

```
O1
                                          SEQ ID NO: 6
5'-AA TT GTG AGC G GAT AAC AA TT-3'

O2
                                          SEQ ID NO: 7
5'-AA AT GTG AGC G AGT AAC AA CC-3'

O3
                                          SEQ ID NO: 8
5'-GG CA GTG AGC G CAA CGC AA TT-3'

Lsym
                                          SEQ ID NO: 9
5'-AA TT GTG AGC GCT CAC AA TT-3'
```

In one embodiment, an operator sequence is located between the TATA box and the start of transcription within the promoter. In another embodiment, an operator sequence is located upstream of the repressor gene. In another embodiment, the operator sequence is located upstream of the transgene in the cassette. In another embodiment, the operator sequence is located downstream of the promoter at about 70 bp from the start of transcription of the repressor gene or the transgene in the cassette. In still another embodiment, the operator sequence is located downstream of the promoter at about 92 bp from the start of transcription of the repressor gene or the transgene in the cassette. In one embodiment, the cassette contains multiple operator DNA sequences responsive to the expressed repressor protein. In one embodiment, the cassette contains one or two Lsym operator DNA sequences responsive to the expressed repressor protein. It is anticipated that other locations and other multiples of operators will be suitable for placement of the multiple operators in the constructs described herein. See, for example, the locations of the optimized LacI operator sequences described in FIG. 14 SEQ ID NO: 15 and Example 8 Table I.

Ribozyme-Aptamer Sequences

In the dual-regulating constructs described herein, the use of a ligand-dependent ribozyme-aptamer sequence provides a second layer of regulation and controls any leakiness of transcription that occurs from allowing the repressor to shut off transcription. Hammerhead ribozymes represent one of a number of distinct structural classes of natural self-cleaving RNAs. A hammerhead ribozyme is characterized by a three-stem junction constituting the catalytic core. Additional sequence and structural elements form an extended hammerhead motif. See, e.g., Perreault J et al, 2011 PLOS Compu. Biol., 7(5): e1002031). Coupling an aptamer, i.e., a three-dimensional nucleic acid sequence that is capable of binding a specified target, to a ribozyme has permitted the generation of ribozymes useful in the constructs herein. Such ribozymes are described in detail in Beilstein K. et al, 2015 May, ACS Synth Biol., 4(5):526-534 (ref 53), incorporated by reference herein. In fact, Example 8 below employs as one embodiment a dual self regulating construct employing the K7 tetracyline-dependent hammerhead ribozyme-aptamer as well as others. In the absence of the ligand, i.e., second inducing molecule, to which the aptamer sequence specifically binds, the ribozyme self-cleaves, thus degrading the mRNA.

A variety of ribozyme-aptamers or riboswitches are described. Further aptamer sequences may be readily designed to bind to any selected small molecule which is desired to be used as a second inducing molecule in the dual regulatory construct described herein. In one embodiment, the aptamer binds tetracycline as described[53]. However, an aptamer designed to bind another small molecules, such as IPGT, permits the first inducer and second inducer used in the dual regulatory construct to be the same molecule, thus increasing the efficiency of the dual construct in transgene expression regulation. Aptamers are generally random RNA sequences of about 40-50 nucleotides in length. High throughput screens are used to identify new aptamer RNA sequences that bind to a selected small molecule.

Therefore, the specific ribozyme and aptamer construct exemplified herein does not limit the dual constructs. Other such ribozyme-aptamer switches may be readily used in a similar manner. It is particularly desired that the ribozyme-aptamer sequence be located in the dual construct upstream of the polyadenylation sequence. In the construct exemplified in FIGS. 11 and 12, and in the sequence of FIG. 14 the ribozyme-aptamer sequence is located in the construct between the transgene and the polyA sites. In another embodiment, the ribozyme-aptamer sequence is located in the construct in any position in which it does not disrupt the open reading frame of the transgene sequence or disrupt the functioning of the other components of the dual self-regulating construct, provided that it is always upstream of the polyA sequence.

Thus, other ribozyme-aptamer sequences are anticipated to be useful in the constructs described herein.

The Selected Transgene Sequence.

The selection and composition of the transgene sequence will depend upon the use to which the resulting vector will be put. The transgene may be used to correct or ameliorate gene deficiencies which may include deficiencies in which normal genes are expressed at less than normal levels or deficiencies in which the functional gene product is not expressed. In one embodiment, a transgene sequence encodes a therapeutic protein or polypeptide which is expressed in a target cell.

In one embodiment, the transgene encodes a product which is useful in biology and medicine, such as proteins, peptides, RNA, enzymes, or catalytic RNAs. RNA molecules include shRNA, tRNA, dsRNA, ribosomal RNA, catalytic RNAs, and antisense RNAs. One example of a useful RNA sequence is a sequence which extinguishes expression of a targeted nucleic acid sequence in the treated animal.

More specifically, in one embodiment, the transgene encodes a human gene for expression in an ocular cell. The selection of transgene may be made by one of skill in the art. A variety of transgenes are useful and would generally depend upon the particular use of the virus, e.g., for the treatment of a particular disease. Thus, a suitable transgene may be soluble Flt (sFlt), angiostatin, endostatin, RdCVF, GDNF, BDNF, XIAP, BCL2, CNTF, or PEDF. Where the virus is being used to treat ocular diseases, other suitable transgenes are RHO, LCA5, CHM, ABCA4, RPE65, RDH12, CEP290, RPGR, PRPF31, CNGB3.

In one embodiment, the transgene is selected to provide optogenetic therapy. In optogenetic therapy, artificial photoreceptors are constructed by gene delivery of light-activated channels or pumps to surviving cell types in the remaining retinal circuit. This is particularly useful for patients who have lost a significant amount of photoreceptor function, but whose bipolar cell circuitry to ganglion cells and optic nerve remains intact. In one embodiment, the heterologous nucleic acid sequence (transgene) is an opsin. The opsin sequence can be derived from any suitable single- or multicellular-organism, including human, algae and bacteria. In one embodiment, the opsin is rhodopsin, photopsin, L/M wavelength (red/green)-opsin, or short wavelength (S) opsin (blue). In another embodiment, the opsin is channelrhodopsin or halorhodopsin.

In another embodiment, the transgene is selected for use in gene augmentation therapy, i.e., to provide replacement copy of a gene that is missing or defective. In this embodiment, the transgene may be readily selected by one of skill in the art to provide the necessary replacement gene. In one embodiment, the missing/defective gene is related to an ocular disorder. In another embodiment, the transgene is NYX, GRM6, TRPM1L or GPR179 and the ocular disorder is Congenital Stationary Night Blindness. See, eg., Zeitz et al, Am J Hum Genet. 2013 Jan. 10; 92(1):67-75. Epub 2012 Dec. 13 which is incorporated herein by reference.

In another embodiment, the transgene is selected for use in gene suppression therapy, i.e., expression of one or more native genes is interrupted or suppressed at transcriptional or translational levels. This can be accomplished using short hairpin RNA (shRNA) or other techniques well known in the art. See, e.g., Sun et al, Int J Cancer. 2010 Feb. 1; 126(3): 764-74 and O'Reilly M, et al. Am J Hum Genet. 2007 July; 81(1):127-35, which are incorporated herein by reference. In this embodiment, the transgene may be readily selected by one of skill in the art based upon the gene which is desired to be silenced.

In another embodiment, the transgene is selected for use in gene correction therapy. This may be accomplished using, e.g., a zinc-finger nuclease (ZFN)-induced DNA double-strand break in conjunction with an exogenous DNA donor substrate. See, e.g., Ellis et al, Gene Therapy (epub January 2012) 20:35-42 which is incorporated herein by reference. The transgenes may be readily selected by one of skill in the art based on the intended therapeutic result.

In another embodiment, the transgene is selected for use in neurotropic factor gene therapy, i.e., providing exogenous neurotropic factors to provide neuroprotection. In this embodiment, the transgene may be any neurotropic factor, including ciliary-derived neurotrophic factor (CNTF), fibroblast growth factor (FGF), glial-derived neurotrophic factor (GDNF), Rod-derived Cone Viability Factor (RdCVF) (Yang et al, Mol Ther. 2009 May; 17(5):787-95) and brain-derived neurotrophic factor (BDNF). See, e.g., Schlichtenbrede et al, Gene Therapy (2003) 10, 523-527. The neurotropic factor may be readily selected by one of skill in the art. These documents are incorporated herein by reference.

Transgenes selected for expression where the disease is not an ocular disease may include, without limitation, nucleic acid sequences encoding insulin, growth hormone, erythropoietin, antibodies (e.g., to HIV envelope proteins, herpes virus, and other pathogens), clotting factors such as factor VIII, factor IX; galactosidase, enzymes involved in lysosomal storage disease (e.g., alpha-glucocerebrosidase, alpha-iduronidase, arylsulphatase B).

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), platelet-derived growth factor (PDGF), insulin growth factors I and II (IGF-I and IGF-II), any one of the transforming growth factor $\alpha$ superfamily, including TGF$\alpha$, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattractant protein, leukemia inhibitory factor, granulocyte-macrophage colony stimulating factor, Fas ligand, tumor necrosis factors $\alpha$ and $\beta$, interferons $\alpha$, $\beta$, and $\gamma$, stem cell factor, flk-2/flt3 ligand. Gene products produced by the immune system are also useful in the invention. These include, without limitations, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. Other transgenes are receptors for cholesterol regulation and/or lipid modulation, including the low density lipoprotein (LDL) receptor, high density lipoprotein (HDL) receptor, the very low density lipoprotein (VLDL) receptor, and scavenger receptors. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZFS, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful transgene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin gene product [e.g., a mini- or micro-dystrophin]. Still other useful transgene products include enzymes such as may be useful in enzyme replacement therapy, which is useful in a variety of conditions resulting from deficient activity of enzyme. For example, enzymes that contain mannose-6-phosphate may be utilized in therapies for lysosomal storage diseases (e.g., a suitable gene includes that encoding β-glucuronidase (GUSB)).

Still other useful transgenes encode products include those used for treatment of hemophilia, including hemophilia B (including Factor IX) and hemophilia A (including Factor VIII and its variants, such as the light chain and heavy chain of the heterodimer and the B-deleted domain; U.S. Pat. Nos. 6,200,560 and 6,221,349).

In another embodiment, the transgenes useful herein include reporter sequences, which upon expression produce a detectable signal. Such reporter sequences include, without limitation, DNA sequences encoding β-lactamase, β-galactosidase (LacZ), alkaline phosphatase, thymidine kinase, green fluorescent protein (GFP), red fluorescent protein (RFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc.

These reporter coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is green fluorescent protein or luciferase, the vector carrying the signal may be measured visually by color or light production in a luminometer.

Nucleic acids sequences coding for the gene products can be obtained using recombinant methods or by deriving the sequence from a vector known to include the same. Furthermore, the sequence can be isolated directly from cells and tissues containing the same, using standard techniques, such as phenol extraction and PCR of cDNA or genomic DNA [See, e.g., texts such as the various editions of Sambrook et al, Molecular Cloning: A Laboratory Manual, Cold Spring Harbor Press, Cold Spring Harbor, N.Y. Transgene nucleotide sequences can also be produced synthetically, rather than cloned.

The transgenes useful in these cassettes are not limited to human transgenes. Indeed, it is intended that the above transgenes may be those of animals other than humans, including but not limited to companion animals (e.g., canine, felines, and equines), livestock (e.g., bovines, caprines and ovines), laboratory animals, marine mammals, large cats, etc. Such compositions and methods described herein are thus useful for treatment of plant and agricultural processes as well.

As stated throughout this specification, the selection of the transgene may be selected depending upon the therapeutic use to which the recombinant vector is to be put. The lists of transgenes described herein are not limiting.

Other Components

In one embodiment, the DNA encoding the repressor gene and the transgene are separated by an internal ribozyme entry site (IRES). IRES was originally discovered in poliovirus RNA, where it promotes translation of the viral genome in eukaryotic cells. A variety of IRES sequences have been discovered from viruses and from cellular mRNAs. IRES sequences spark translation initiation independent of the 5' cap. IRES sequences are quite large (500-600 bp). An exemplary IRES is the poliovirus internal ribosome entry sequence, which supports transgene expression in photoreceptors, RPE and ganglion cells. Still others are known and available in the art (see Mokrejs M et al, 2010 Nucl Acids Res, 39(S1):D131-D136).

As an alternative to an IRES, the DNA encoding the repressor and transgene are separated by sequences encoding a 2A peptide, which self-cleaves in a post-translational event. See, e.g., Donnelly[40]; Furler, S., et al, Gene Ther., 8(11):864-873 (June 2001); Klump H., et al., Gene Ther., 8(10):811-817 (May 2001). This 2A peptide is significantly smaller than an IRES, making it well suited for use when space is a limiting factor. A variety of such 2A cleavage sites exist. See the summary in Kim J H et al, PLoS One, 2011 6(4): e18556. doi: 10.1371/journal.pone.0018556, incorporated by reference herein. An exemplary 2A sequence is disclosed at nt.2188-2253 of SEQ ID NO: 15.

In other embodiments, the cassette further comprises a spacer sequence of about 15-25 nucleic acids interposed between the repressor sequence and the transgene in the cassette. In another embodiment, the cassette further comprises an intron spaced between the promoter and the one or more operator sequences and the repressor gene. In still another embodiment the cassette further comprises a nuclear localization sequence (NLS). In certain embodiments, each component of the cassette is codon optimized for expression in human cells.

Additional regulatory sequences for inclusion in the cassette include, without limitation, an enhancer sequence, a polyadenylation sequence, a splice donor sequence and a splice acceptor sequence, a site for transcription initiation and termination, a ribosome binding site for translation in the transcribed region, an epitope tag, a Goldberg-Hogness "TATA" element, a restriction enzyme cleavage site, a selectable marker, origins of replication, polyadenylation sequences (e.g., BGH polyA, SV40 polyA), drug resistance markers (e.g., kanamycin resistance). All such elements may also be selected from among widely known sequences. Examples of such publically available sequences are illustrated in Example 8, Table I and in FIG. 14 and SEQ ID NO: 15.

Exemplary Cassettes

In one embodiment, self-regulating expression constructs described above and are flanked on either end by a 5' AAV ITR and a 3' AAV ITR so that the repressor is arranged so that it is autogenously regulated, and optionally the mRNA degradation is similarly regulated and the construct can be used in an AAV expression cassette. The size of these gene expression constructs or switches are small, thus they are ideal for AAV delivery system. Because a single plasmid design encompasses all the elements of either embodiment of the switch, these constructs are ideal for use in recombinant AAV as vectors, although they are useful in other viral or non-viral vectors.

In one embodiment, the gene expression cassette or genetic switch comprises: a CMV promoter; the appropriate operator(s) that works with the corresponding lacI or galR repressor family member; a lacI or galR family member repressor protein that can utilize its own metabolic inducer (Isopropyl β-D-1-thiogalactopyranoside-IPTG), a 2A or IRES sequence and a selected transgene. In another embodiment, the switch further comprises a ribozyme-aptamer construct to regulate mRNA degradation.

As one example, a heterologous self-regulating gene expression cassette comprises in operative association: a single minimal CMV1 promoter controlling expression of the repressor sequence and transgene; one or two Lsym operator DNA sequences responsive to the expressed repressor protein; the lacI repressor gene sequence; a 2A sequence; and a selected transgene sequence. In another embodiment, the construct further included a hammerhead ribozyme in association with a tetracycline-binding aptamer upstream of the polyadenylation site. In another embodiment, this construct is flanked with κ' AAV ITR and 3' AAV ITR, as in FIG. 14. Optional spacers, intergenic sequences, and nuclear localization sequences among others may be included in the cassette.

As another example, a heterologous self-regulating gene expression cassette comprises in operative association, the nucleic acid sequences providing or encoding: (a) a single minimal CMV1 promoter controlling expression of the repressor sequence and transgene; (b) one Lsym operator DNA sequence responsive to the expressed repressor protein; (c) the dimeric lacI repressor gene sequence; (d) a 2A sequence; and (e) a selected transgene sequence. In another embodiment, the construct further includes a hammerhead ribozyme in association with a tetracycline-binding aptamer upstream of the polyadenylation site. In another embodiment, this construct is flanked with 5' AAV ITR and 3' AAV ITR. Optional spacers, intergenic sequences, and nuclear localization sequences among others may be included in the cassette.

As another example, a heterologous self-regulating gene expression cassette comprises in operative association, the nucleic acid sequences providing or encoding: a single minimal CMV1 promoter controlling expression of the repressor sequence and transgene; two Lsym operator DNA sequences responsive to the expressed repressor protein; the tetrameric lacI repressor gene sequence; a 2A sequence; and a selected transgene sequence. In one embodiment, the construct further includes a hammerhead ribozyme in association with a tetracycline-binding aptamer upstream of the polyadenylation site. In another embodiment, this construct is flanked with 5' AAV ITR and 3' AAV ITR. Optional spacers, intergenic sequences, and nuclear localization sequences among others may be included in the cassette.

In still another example, a heterologous self-regulating gene expression cassette comprises in operative association, the nucleic acid sequences providing or encoding: a single minimal CMV1 promoter/enhancer controlling expression of the repressor sequence and transgene; from one to three Lac operator DNA sequences responsive to the expressed repressor protein; a lacI or dimeric lacI or tetrameric lacI repressor gene sequence; a 2A cleavage sequence; a selected transgene sequence; a hammerhead ribozyme in association with a tetracycline-binding aptamer upstream of the polyadenylation site. In another embodiment, this construct is flanked with 5' AAV ITR and 3' AAV ITR, as in FIG. 14. Optional spacers, intergenic sequences, and nuclear localization sequences among others may be included in the cassette.

The examples below discuss in detail the assembly of plasmids and creation of cassettes and constructs as described herein for use in a recombinant vector as discussed below.

Another aspect of this invention is a recombinant vector containing the heterologous gene expression construct or cassette. As used herein, a vector may include any genetic element including, without limitation, naked DNA, a phage, transposon, cosmid, episome, plasmid, bacteria, virus or nanoparticle. As used herein, the term vector refers to a genetic element which expresses, or causes to be expressed, the "heterologous gene" in the host cell. In a preferred embodiment, the "heterologous gene" is a nucleic acid sequence that encodes the repressor protein and the nucleic acid sequence that encodes the transgene. The gene expression cassettes or constructs described herein can be produced in plasmid based systems, of which many are commercially available.

However, one embodiment because they are easy to deliver, are non-replicating recombinant viral vectors. Thus, in one embodiment, the vector is a non-pathogenic virus. In another embodiment, the vector is a non-replicating virus. In one embodiment, a viral vector may be a retroviral vector, such as a lentiviral vector. In another embodiment, a vector is an adenoviral vector. In still another embodiment, a suitable vector is an adeno-associated viral vector. Adenovirus, adeno-associated virus and lentiviruses infect actively dividing as well as resting and differentiated cells such as the stem cells, macrophages and neurons. A variety of adenovirus, lentivirus and AAV strains are available from the American Type Culture Collection, Manassas, Va., or available by request from a variety of commercial and institutional sources. Further, the sequences of many such strains are available from a variety of databases including, e.g., PubMed and GenBank.

In one embodiment, the recombinant vector is a recombinant adeno-associated virus (AAV). Recombinant adeno-associated virus (AAV) vectors have been developed for gene replacement therapy because they are non-pathogenic and exhibit a broad range of tissue specificity (Flotte and Carter 1995). These vectors generally retain the AAV inverted terminal repeats (ITRs) located at each end of a gene expression cassette, but lack the AAV rep and cap genes necessary for viral replication and packaging. Therefore rAAV cannot replicate, and viruses must be assembled in packaging cell lines with the rep and cap functions supplied in trans or expressed within the packaging cell itself. The gene expression cassette described above is flanked by 5' and 3' AAV inverted terminal repeats (ITRs) for insertion into the rAAV. The auto-regulated gene expression cassette described above, flanked by the AAV ITRs, may also be referred to herein as a minigene. It is this minigene which is packaged into a capsid protein to form an rAAV particle, which is delivered to a selected target for therapeutic applications.

The design and construction of the components, such as the plasmids and gene expression cassettes necessary for producing a recombinant AAV or other recombinant virus or recombinantly transfected host cells, can be quite labor intensive, due to the variety of plasmids and vectors available, and the need to modify the genes to fit into the appropriate plasmids. This complexity is further increased by pharmaceutical industry and governmental requirements surrounding obtaining approval of an rAAV for pharmaceutical use.

The AAV may have one of multiple AAV serotypes (i.e., any one of the known AAV1-10 as well as engineered AAV variants. The recombinant virus can contain an AAV capsid proteins of serotype AAV1-10, AAV variants made by directed evolution (such as AAV8B, AAV7m8; or tyrosine mutant capsid AAVs. In one embodiment, the AAV capsid is AAV8-AAV8B, AAV5, AAV7m8, AAVs with tyrosine mutants (such as Y733F, quad Y-F). See, e.g., International patent application No. PCT/US14/015340; U.S. Pat. No. 7,282,199, among other known patents discussing AAV variants.

In one embodiment, the vectors useful in compositions and methods described herein contain, at a minimum, sequences encoding a selected AAV capsid, e.g., an AAVb or AAVh capsid, or a fragment thereof. In another embodiment, useful vectors contain, at a minimum, sequences encoding a selected AAV serotype rep protein, e.g., AAV8 rep protein, or a fragment thereof. Optionally, such vectors may contain both AAV cap and rep proteins. In vectors in which both AAV rep and cap are provided, the AAV rep and AAV cap sequences can both be of one serotype origin, e.g., all AAV8 origin. Alternatively, vectors may be used in which the rep sequences are from an AAV which differs from the wild type AAV providing the cap sequences. In one embodiment, the rep and cap sequences are expressed from separate sources (e.g., separate vectors, or a host cell and a vector). In another embodiment, these rep sequences are fused in frame to cap sequences of a different AAV serotype to form a chimeric AAV vector, such as AAV2/8 described in U.S. Pat. No. 7,282,199, which is incorporated by reference herein.

In another embodiment, the AAV is a self-complementary AAV (sc-AAV) (See, US 2012/0141422 which is incorporated herein by reference). Self-complementary vectors package an inverted repeat genome that can fold into dsDNA without the requirement for DNA synthesis or base-pairing between multiple vector genomes. Because scAAV have no need to convert the single-stranded DNA (ssDNA) genome into double-stranded DNA (dsDNA) prior to expression, they are more efficient vectors. However, the trade-off for this efficiency is the loss of half the coding capacity of the vector. ScAAV are useful for small protein-coding genes (up to ~55 kd) and any currently available RNA-based therapy.

Pseudotyped vectors, wherein the capsid of one AAV is replaced with a heterologous capsid protein, are useful herein. Unless otherwise specified, the AAV ITRs, and other selected AAV components described herein, may be individually selected from among any AAV serotype, including, without limitation, AAV1, AAV2, AAV3, AAV4, AAV5, AAV6, AAV7, AAV8, AAV9, AAV10 or other known and unknown AAV serotypes. In one embodiment, the ITRs of AAV serotype 2 are used. However, ITRs from other suitable serotypes may be selected. These ITRs or other AAV components may be readily isolated using techniques available to those of skill in the art from an AAV serotype. See also, International Patent Application Publication No. WO2006/110689, incorporated herein by reference. Such AAV may be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank, PubMed, or the like.

In one embodiment, a lentiviral vector is used. Among useful vectors are the equine infectious anemia virus, and feline and bovine immunodeficiency virus, and HIV-based vectors. A variety of useful lentivirus vectors, as well as the methods and manipulations for generating such vectors for use in transducing cells and expressing heterologous genes are described in N Manjunath et al, 2009 Adv Drug Deliv Rev., 61(9): 732-745, incorporated herein by reference. In one embodiment the self-inactivating lentiviral vector (GeMCRIS 0607-793) which was successfully used to transduce T cells directed against tumor cells in leukemia patients (Porter et al., N Engl J Med. 2011 Aug. 25; 365(8):725-33) is useful to carry and express a nucleotide sequence.

Methods of producing recombinant vectors for delivery of the self-regulating gene expression constructs with its selected repressors, operators, promoters and transgenes, and ribozyme-aptamers as described above are generally known in the art. Such methods employ known recombinant methods of assembly. Given the teachings of this specification, and the knowledge extant in the art, one of skill in the art can readily assemble a recombinant vector as described herein. See, e.g., texts such as the various editions of Sambrook et al, Molecular Cloning: A Laboratory Manual, Cold Spring Harbor Press, Cold Spring Harbor, N.Y.

In one aspect, a method of producing a recombinant adeno-associated virus (AAV) containing a heterologous self-regulating gene cassette comprises (a) inserting a heterologous self-regulating gene expression cassette as described herein in an AAV cis construct with AAV ITR sequences flanking the gene expression construct or cassette. The resulting AAV cis construct is co-transfected into a mammalian cell with a packaging plasmid containing the capsid proteins of a selected AAV type and an adenoviral helper plasmid. Infectious AAV particles having a selected AAV capsid protein and comprising the gene cassette are produced. Optionally the infectious AAV particles are subjected to purification processes to separate the particles from the other components of the host cell.

The above-described recombinant viral or non-viral vectors may be delivered to host cells according to published methods. Where the delivery to a host cell is designed for in vitro expression, e.g., for research, the vectors may be delivered in any conventional manner to the selected host cell, e.g., mammalian, insect, avian, etc. The host cells may be selected from any host cell commonly used in research. Similarly the formulation of the vectors for laboratory research is well known. Where the vectors are intended for pharmaceutical use, the vectors, preferably suspended in a physiologically compatible carrier, may be administered to a human or non-human mammalian patient. Suitable carriers may be readily selected by one of skill in the art in view of the indication for which the vector is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the recombinant vector (e.g., rAAV) and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, systemic administration, depending on the disease and cells to be targeted. Conventional and pharmaceutically acceptable routes of administration include, but are not limited to, direct delivery to a desired organ or cell type (e.g., the liver/hepatic cells (optionally via the hepatic artery) or lung), oral, inhalation, intranasal, intratracheal, intraarterial, intraocular, intravenous, intramuscular, subcutaneous, intradermal, and other parental routes of administration. Routes of administration may be combined.

Concentrations, doses or dosages of the vector will depend primarily on factors such as the condition being treated, the age, weight and health of the patient, and may thus vary among patients. For example, a therapeutically effective human amount of a viral vector is generally in the range of from about 0.1 mL to about 100 mL of a suspension containing concentrations of from about $1 \times 10^9$ to $1 \times 10^{16}$ genomes virus vector. A preferred human amount for delivery to large organs (e.g., liver, muscle, heart and lung) may be about $5 \times 10^{10}$ to $5 \times 10^{13}$ AAV genomes per 1 kg, at a volume of about 1 to 100 mL of suspension. A preferred amount for delivery to eye is about $5 \times 10^9$ to $5 \times 10^{12}$ genome copies, at a suspension volume of about 0.1 mL to 1 mL. The amounts will be adjusted to balance the therapeutic benefit against any side effects and such amounts may vary depending upon the therapeutic application for which the recombinant vector is employed. The levels of expression of the transgene can be monitored to determine the frequency of delivery of viral vectors, preferably AAV vectors, containing the minigene. Optionally, delivery regimens similar to those described for therapeutic purposes may be utilized for immunization using the compositions of the invention.

In one embodiment, the recombinant AAV or other vector containing the self-regulating gene expression cassettes for use in the target ocular cells as detailed herein is optionally assessed for contamination by conventional methods and then formulated into a pharmaceutical composition intended for subretinal or intravitreal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20. In another embodiment, the pharmaceutically acceptable carrier comprises a surfactant, such as perfluorooctane (Perfluoron liquid).

In certain embodiments of the methods described herein, the pharmaceutical composition described above is administered to the subject by subretinal injection. In other embodiments, the pharmaceutical composition is administered by intravitreal injection. Other forms of administration that may be useful in the methods described herein include, but are not limited to, direct delivery to a desired organ (e.g., the eye), oral, inhalation, intranasal, intratracheal, intravenous, intramuscular, subcutaneous, intradermal, and other parental routes of administration. Routes of administration may be combined.

The volume and viral titer of each injection is determined individually, as further described below, and may be the same or different from other injections performed in the same, or contralateral, eye. In another embodiment, a single, larger volume injection is made in order to treat the entire eye. In one embodiment, the volume and concentration of the rAAV composition is selected so that only a specific region of ocular cells is impacted. In another embodiment, the volume and/or concentration of the rAAV composition is a greater amount, in order reach larger portions of the eye, including non-damaged ocular cells. When administered to treat a non-ocular cell, one of skill in the art may adjust the routes of administration and dosages.

In one embodiment, the vector composition may be delivered in a volume of from about 0.1 µL to about 1 mL, including all numbers within the range, depending on the size of the area to be treated, the viral titer used, the route of administration, and the desired effect of the method. In one embodiment, the volume is about 50 µL. In another embodiment, the volume is about 70 µL. In another embodiment, the volume is about 100 µL. In another embodiment, the volume is about 125 µL. In another embodiment, the volume is about 150 µL. In another embodiment, the volume is about 175 µL. In yet another embodiment, the volume is about 200 µL. In another embodiment, the volume is about 250 µL. In another embodiment, the volume is about 300 µL. In another embodiment, the volume is about 450 µL. In another embodiment, the volume is about 500 µL. In another embodiment, the volume is about 600 µL. In another embodiment, the volume is about 750 µL. In another embodiment, the volume is about 850 µL. In another embodiment, the volume is about 1000 µL.

An effective concentration of a recombinant adeno-associated virus carrying a autologous gene expression cassette encoding the transgene ranges between about $10^7$ and $10^{13}$ vector genomes per milliliter suspension (vg/mL) (also called genome copies/mL (GC/mL)). The rAAV infectious units are measured as described in S. K. McLaughlin et al, 1988 J. Virol., 62:1963, which is incorporated herein by reference. Preferably, the concentration in the retina is from about $1.5 \times 10^9$ vg/mL to about $1.5 \times 10^{12}$ vg/mL, and more preferably from about $1.5 \times 10^9$ vg/mL to about $1.5 \times 10^{11}$ vg/mL. In one embodiment, the effective concentration is about $1.4 \times 10^8$ vg/mL suspension. In one embodiment, the effective concentration is about $3.5 \times 10^{10}$ vg/mL. In another embodiment, the effective concentration is about $5.6 \times 10^{11}$ vg/mL. In another embodiment, the effective concentration is about $5.3 \times 10^{12}$ vg/mL. In yet another embodiment, the effective concentration is about $1.5 \times 10^{12}$ vg/mL. In another embodiment, the effective concentration is about $1.5 \times 10^{13}$ vg/mL. In one embodiment, the effective dosage (total genome copies delivered) is between $10^7$ and $10^{13}$ vector genomes. In one embodiment, the lowest effective concentration of virus is utilized in order to reduce the risk of undesirable effects, such as toxicity, retinal dysplasia and detachment. Still other dosages and administration volumes in these ranges may be selected by the attending physician, taking into account the physical state of the subject, preferably human, being treated, the age of the subject, the particular ocular disorder and the degree to which the disorder, if progressive, has developed. For extra-ocular delivery, the dosage will be increased according to the scale-up from the retina. Intravenous delivery, for example may require doses on the order of $1.5 \times 10^{13}$ vg/kg.

Amounts of inducing molecules will vary depending upon the particular use, e.g., in vitro or in vivo research or pharmaceutical use, the condition of any intended host organism, the disease being treated, the size of the organ or tissue being treat, the general health of the subject, etc. Desirably the smallest amount of inducing molecule that can achieve the effect of transiently and controllable interacting with the gene expression construct to control expression of the transgene is desired. In one embodiment the amount of administration of the first inducing molecule and timing and route of administration is the same as that for the second inducing molecule. In other embodiments, the amounts, timing and routes of administration may differ for the two inducing molecules, depending on the identity thereof.

In one embodiment a method of tightly regulating expression of a transgene in a mammalian cell comprising: (a) infecting the cell with a recombinant vector comprising an operational self-regulating inducible dual regulatory gene expression construct, wherein the gene cassette is stably expressed by the infected cell; and (b) contacting the cell in vivo with a first inducing molecule that interacts with the repressor to permit simultaneous expression of the transgene and repressor protein by the single promoter. Thereafter, the cell is contacted in vivo with a second inducing molecule that interacts with the aptamer to prevent the ribozyme from degrading the transcribed message. The first inducing molecule is stopped which permits the repressor protein to autoregulate and reduce or inhibit transcription of the repressor protein and the transgene as the repressor protein accumulates in the cells and interacts with the operator sequence in the absence of additional amounts of the molecule. Substantially simultaneously, the second inducing molecule is stopped, which permits the ribozyme to degrade any further transcription of the repressor and transgene. In one embodiment, the first inducing molecule and the second inducing molecule are the same molecule and therefore these latter steps occur simultaneously to terminate transcription in a tightly regulated manner. Subsequent contact with the inducing molecules is used repeatedly to controllably express the transgene. When the repressor is lacI, the inducing molecule or first inducing molecule is IPTG, an artificial sweetener, or a sugar substitute for sucrose. When the repressor is galR and the inducing molecule or first inducing molecule is galactose. When the repressor is tetR and the inducing molecule or first inducing molecule is tetracycline. When the aptamer binds tetracycline and the second inducing molecule is tetracycline or when the aptamer binds IPTG and the seconding inducing molecule is IPTG, the method employs a single inducing molecule. The inducing molecules are intended to be administered by any convenient and conventional route and in similar amounts.

Another aspect of this invention involves method of controlling expression of a transgene in a mammalian cell. In one embodiment, the method involves infecting the cell with a recombinant virus as described herein, and permitting the gene cassette to become stably expressed by the infected cell. A suitable amount of transgene is expressed in the infected mammalian cell by contacting the cell in vivo with a first inducing molecule that interacts with the repressor to permit simultaneous expression of the transgene and repressor protein by the single promoter. Additionally the cell is contacted in vivo with a second inducing molecule that interacts with the aptamer coupled to the ribozyme to prevent mRNA degradation at the same time. While the first inducing molecule remains in contact with the cell, the repressor protein is expressed along with the transgene. As the molecule diminishes or is no longer in contact with the cell, the increased amount of expression of the repressor protein autoregulates its own expression. As the repressor protein accumulates in the cells, it interacts with the operator sequence, and reduces or inhibits its own expression and that of the transgene in the absence of additional amounts of the molecule. In a dual construct, when the second inducing molecule is removed from the cell, the ribozyme self cleaves and degrades remaining mRNA transcript of the transgene and repressor, thereby assisting in tight control. In another embodiment, therefore, the transgene may be repeatedly increased in expression in the cell whenever the cell is contacted with the first and second molecules, which may be a single molecule which interacts with both the repressor and aptamer. One may thus control the timing and amount of transgene expression by contolling the timing and administration of the first and second inducing molecules.

In one example, where the cassette comprises the repressor is lacI, a suitable first inducing molecule is Isopropyl β-D-1-thiogalactopyranoside (IPTG) or an artificial sweetener such as "Splenda", a sugar substitute for sucrose, such as fructose, a galactoside, a fucosides, etc. Such other innocuous food supplements containing the molecule may be employed for this purpose.

In another example, where the cassette comprises the repressor galR, a suitable first inducing molecule is, for example, galactose or glucose or an artificial sweetener such as "Splenda", a sugar substitute for sucrose, such as fructose, a galactoside, a fucoside, etc.

Still other suitable molecules and repressors responsive to them may be selected or generated by one of skill in the art using the teachings of this specification.

As a specific example, a method of treating an ocular condition in a mammalian, preferably human, subject comprises administering by intravitreal or subretinal injection to a mammalian subject in need thereof a recombinant virus as described herein, wherein the gene cassette in the virus becomes stably expressed in the subject's ocular cells and its expression in the ocular cell is thereafter controllable as described above. In one embodiment, a recombinant AAV carries a heterologous self-regulating gene expression cassette as described above. For example, the cassette comprises a single minimal CMV1 promoter controlling expression of the lacI repressor sequence and a transgene encoding a protein that is absent or defective in the targeted ocular cell. The cassette also contains two Lsym operator DNA sequences responsive to the expressed lacI repressor protein. The first operator sequence is located at about 70 bp from the start of transcription of the repressor gene and the second operator sequence is located at about 90 bp from the start of transcription of the repressor gene. The cassette also contains the lacI repressor gene sequence and a 2A sequence. Additionally, the cassette contains a wildtype or mutated or codon optimized transgene sequence encoding, e.g., RHO, LCA5, CHM, ABCA4, RPE65, RDH12, CEP290, RPGR, PRPF31, or CNGB3.

The course and amount of expression of the transgene once the cassette is stably expressed in the ocular cell is controlled by subsequently and repeatedly administering to the subject a molecule that interacts with the repressor sequence to permit simultaneous expression of the transgene and repressor protein by the single promoter. The first inducing molecule can be administered to the mammalian subject by any suitable route. In certain embodiments, the route is by topical eye drops. In another embodiment, the route is oral, or by injection, e.g., intravenous or intraperitoneal or by any of the routes of administration described above. The molecule in this instance may be IPTG in a suitable formulation for ready administration by the selected route. After first administration of the molecule to the subject, the cassette components operate to turn on expression of the repressor protein and the transgene. In the absence of additional amounts of the molecule, e.g., as the first administration is used up by the subject, the repressor protein autoregulates and reduce or inhibit expression of both itself and the transgene, effectively turning off the expression of the transgene. Any need for increased expression of the transgene is thereby controlled by subsequent and timed readministration of the molecule, e.g., by treating periodically with the eye drops.

Ocular diseases which are suitably treated by this method include, without limitation, ocular neovascular disease (including choroidal neovascularization, a complication of age-related macular degeneration; diabetic retinopathy, sickle cell disease, retinal vein occlusion, retinopathy of prematurity, neovascular glaucoma); glaucoma, age-related macular degeneration, retinitis pigmentosa, Leber's congenital amaurosis, uveitis, congenital stationary nightblindness, optic atrophy, cone dystrophy, Stargardt disease, Bardet-Biedl syndrome, Usher syndrome, systemic disease with retinopathy (such as Stickler syndrome); systemic disease with ocular manifestations (such as Wilson's disease); optic neuritis; and Leber's hereditary optic neuropathy.

As another embodiment, a method of treating an inborn error of metabolism or other disease in a mammalian, preferably human, subject comprises administering by injection or any suitable route of administration to a mammalian subject in need thereof a recombinant virus as described herein, wherein the gene cassette in the virus becomes stably expressed in the subject's hepatic or other cells and its expression in the cell is thereafter controllable as described above. For example, the route of administration may be designed or the particular virus may be selected or viral capsid selected to target certain cells in the subject, such as liver cells, for expression of the transgene. In one embodiment, a recombinant AAV carries a heterologous self-regulating gene expression cassette as described above. For example, the cassette comprises a single minimal CMV1 promoter controlling expression of the galR repressor sequence and a transgene encoding a protein that is absent or defective in the targeted cell. The cassette also contains a single Lsym operator DNA sequences responsive to the expressed galR repressor protein. The operator sequence is located at about 70 bp from the start of transcription of the repressor gene. The cassette also contains the galR repressor gene sequence and a 2A sequence. Additionally, the cassette contains a wildtype or mutated or codon optimized transgene sequence encoding, e.g., insulin, growth hormone, erythropoietin, factor VIII, factor IX; galactosidase, alpha-glucocerebrosidase, alpha-iduronidase, or arylsulphatase B.

The course and amount of expression of the transgene once the cassette is stably expressed in the cell is controlled by subsequently and repeatedly administering to the subject a molecule that interacts with the galR repressor sequence to permit simultaneous expression of the transgene and repressor protein by the single promoter. The first inducing molecule can be administered to the mammalian subject by any suitable route. In certain embodiments, the route is oral. In another embodiment, the route is topical, by inhalation, or by injection, e.g., intravenous or intraperitoneal. The molecule in this instance may be glucose in a suitable formulation for ready administration by the selected route. After first administration of the molecule to the subject, the cassette components operate to turn on expression of the repressor protein and the transgene. In the absence of additional amounts of the molecule, e.g., as the first administration is used up by the subject, the repressor protein autoregulates and reduce or inhibit expression of both itself and the transgene, effectively turning off the expression of the transgene. Any need for increased expression of the transgene is thereby controlled by subsequent and timed readministration of the molecule, e.g., by treating periodically with the eye drops.

Diseases which are suitably treated by this method include, without limitation, inborn errors of metabolism, including fatty acid oxidation or gluco-neogenesis; diabetes, pituitary hormone deficiency, chronic disease (including cancer) that impacts erythropoietin production.

Another example of a method of using the self-regulating gene expression systems and recombinant vectors described herein includes in the regulated expression of anti-angiogenic inhibitors of VEGF, such as Bevacizumab (Avastin), in the eye for the treatment of the exudative form of age-related macular degeneration (or wet AMD). Current practice for this indication requires repeated ocular injections of the protein product. In one embodiment, use of the compositions of this invention, e.g., an rAAV containing a self-regulating gene expression cassette carrying an anti-angiogenic inhibitor transgene, enables, with a single injection, delivery of the therapeutic inhibitor protein to the ocular cell. Because there are safety concerns associated with expressing an anti-angiogenic factor at high levels for long periods of times, the compositions and methods described herein permit expression of the anti-angiogenic factor for limited durations and in limited amounts. Thus, this manner of treatment allows for regulated exposure to the inhibitor so that VEGF, which remains important for the maintenance of a healthy retina even in wet AMO, can be expressed in a balance with the therapeutic VEGF-antagonist. Genetic control using the compositions and method may be continuously adjustable in magnitude which is useful for AMO or any genetic therapy in which intermediate levels of gene expression are indicated.

In another embodiment, the self-regulating gene expression systems and recombinant vectors described herein can be employed in methods for delivering a neurotrophic factor for the treatment of retinal degeneration. In one embodiment one may "titer" the expression of such a factor to limit side effects to cells uninvolved in the disease process.

In another embodiment, the self-regulating gene expression systems and recombinant vectors described herein can be employed in methods for regulated expression of anti-microbial proteins, such as broadly neutralizing antibodies toward, e.g., influenza and HIV, to a mammalian subject.

In another embodiment, the self-regulating gene expression systems and recombinant vectors described herein can be employed in methods for regulated expression of insulin cDNA or erythropoietin cDNA as transgene for treatment of diabetes or anemia, respectively. Careful control of gene expression over time is necessary for either condition.

In another embodiment, the self-regulating gene expression systems and recombinant vectors described herein can be employed in known agricultural crop enhancement that employing vectors to express desired plant genes in plant cells to confer certain characteristics to the plant, e.g., resistance to drought, stress, over-ripening, etc.

In another embodiment, the self-regulating gene expression systems and recombinant vectors described herein can be employed in non-human model organisms for scientific study.

Many more indications and gene therapy strategies that require the ability to fine-tune the level of expression can be treated with the compositions and methods described herein. In one embodiment, the compositions and methods are useful to fine-tune the level of expression to physiological levels for a naturally expressed molecule or transgene. In another embodiment, the compositions and methods are useful to fine-tune the level of expression to levels with a therapeutic window for protein drugs. In another embodiment, the compositions and methods are useful to fine-tune the level of expression to control expression of silencing RNA. Delivering these and other therapeutic transgenes based on need, symptoms or circadian rhythm may be accomplished using the compositions and methods described herein. Moreover, the ability to turn off expression by withdrawing the inducing molecules is highly desirable from a safety perspective in order to remove the genetic graft following vector administration.

As instructed by the teachings of this specification, one of skill in the art may select the cassette components so as to make a recombinant vector or recombinant virus useful to treat any particular disease or defect. The compositions and method described herein may be incorporated into genetic therapies for human disease, including reducing the expression level variance in genetic therapies for human diseases caused by insufficient expression of proteins. The compositions and method described herein may be incorporated into genetic therapies for veterinary medicine. Additionally, model organisms for various genes of interest could be produced with very consistent and toggle-able levels of gene expression.

The following examples are illustrative only, and do not limit the scope of the present invention. Particular embodiments of the autogenous genetic switch and its uses are described below. We have redesigned the lacI repressor genetic switch to be autogenously regulated (regulates its own expression) to create an AAV-mediated gene therapy regulatory tool. This autogenous switch was shown to work in various cell types in cell culture. We have improved regulatory behavior of the switch through the use of multiple operator DNA sites and the restoration of the tetramerization domain in the lacI repressor. We found further improvement by making point mutations to the lacI repressor that are known to improve the phenotype in *E. coli*. Additional improvements were added by the dual regulatory embodiments which includes a second inducing molecule-dependent ribozyme-aptamer. Finally, we packaged our autogenously regulated gene expression constructs or switches in AAV vectors. These vectors were used to reversibly regulate luciferase expression in the livers of living mice as a function of IPTG as the first inducing molecule.

Example 1: Methods And Materials

Bacterial Strains and Media

The strain EPB229 (*E. coli* F-λ-ilvG-rfb-50 rph-1Δ(lacI-lacA)::frt) was used for prokaryotic GFP regulation assays. This strain was made by the laboratory of Dr. Mark Goulian and derived from MG1655 (*E. coli* F-λ-ilvG-rfb-50 rph-1). This strain is the "wild-type" K-12 strain and has a total deletion of the lacI operon allowing for a clean background within which to study our lacI genetic regulatory systems. Liquid media for GFP regulation assays with EPB229 cells used MOPS minimal media supplanted with 0.4% glucose and 50 µg/mL kanamycin.

Eukaryotic Cell Lines and Media

The following cell lines were used for eukaryotic GFP and luciferase regulation assays and also in microscopy: The cell line HEK293T is derived from human embryonic kidney cells and stably expresses the Simian Vacuolating Virus (SV40) which codes for the large T-antigen. The cell line Cos-7 was derived from the African green monkey *Cercopithecus aethiops* fibroblast-like kidney cells. This cell line was developed from the CV-1 line by transformation with SV40 to express the T-antigen. The cell line ARPE-19 was derived from human retinal pigment epithelial (RPE) cells.

The culture medium for all cell lines was Dulbecco's modified Eagle's medium (DMEM) containing 20% fetal bovine serum (FBS), L-glutamine and sodium bicarbonate. For ARPE-19 cells, DMEM was supplemented with F-12 nutrient mixture containing 20% fetal bovine serum (FBS), L-glutamine and sodium bicarbonate.

Plasmid Preparation

Plasmids were isolated using the NucleoSpin plasmid purification kit (Clontech). For both the repressor and reporter bacterial plasmids a slightly modified protocol was followed as they both are low-copy number plasmids. A larger initial volume of LB is inoculated (8 mL) and larger volumes of individual DNA purification buffers are used: 500 µL A1, 500 µL A2, and 700 µL A3 of the Macherey-Nagel quick purification kit. The remainder of the protocol was unchanged. Large volumes of plasmid were obtained using the Plasmid Plus Maxi Kit (Qiagen). This allowed for endotoxin free plasmid preparation for transient transfections and also for virus preparation from AAV encoding plasmids.

Cloning—Inverse PCR Mutagenesis

The following protocol was used for point mutations, deletions and small insertions (typically less than 10 base pairs). The primer design completely defines what the result of the cloning will be. Each primer is broken down into two parts: an annealing region that overlaps with the starting plasmid and an optional un-matched 5' tail. The annealing region is designed to follow two basic rules. First, the melting temperature should be as close to 60° C. as possible. Second, both the 3' and 5' ends should be either cytosine (C) or guanine (G). The reverse primer is designed to anneal to the left of the region to change/insert/delete and the forward primer is designed to anneal to the right of the region to change/insert/delete.

For a deletion, primers are chosen that skip the region to delete. For a point mutation, a 5' tail is added to one of the primers that matches the desired sequence. Similarly, for an insertion a 5' tail is added to one of the primers that matches the desired insertion. Finally, one of the primers is given a 5' phosphorylation. Full circle PCR is used with Phusion Hot Start High Fidelity DNA Polymerase (NEB) and the extension time is set to 20 seconds for every kilobase and follows the recommended thermal cycle. PCR follows 15 rounds of amplification and is then held at 4 C until ready to proceed. The mixture now contains plasmid (initially isolated from DH5α) and linearized PCR product which has the desired change/insert/deletion. A 10 minute ligation with 2000 Units T4 DNA Ligase (NEB), 10 µL quick ligation buffer (NEB) and 10 µL PCR product is used to ligate the linearized PCR product into closed plasmid. This is followed by a 1 hour digestion to remove the initial plasmid by adding 5 µL NEB #4 Buffer, 25 µL MilliQ, and 20 Units DpnI (NEB). The DpnI enzyme specifically cleaves DNA with the methylation pattern given by DH5α cells, therefore specifically cleaving only the starting plasmid while sparing the ligated PCR product. 2.5 µL of this mixture is transformed into 50 µL DH5α cells and plated onto LB agar with appropriate selection antibiotic.

Typically >90% of colonies that survive on the plate have the intended change/deletion/insertion. Common difficulties are 5' adenosine (A) or thymine (T) bases will not make it into the final plasmid which is why they are to be avoided if possible in the initial primer design step. It is also commonly seen that the starting plasmid will survive the DpnI digestion so it is recommended to include a DpnI negative control where primers are omitted so only starting plasmid exists.

Cloning—In-Fusion

This method is used to insert large DNA segments into plasmids. The primer design exactly follows the recommendations of the In-Fusion HD Liquid Kit (Clontech). Long DNA regions (approximately greater than 1 kilobase) were amplified with Phusion Hot Start High Fidelity DNA Polymerase (NEB) following the standard thermal cycle and extension time of 20 seconds per kilobase. Small DNA regions (approximately less than 1 kilobase) were amplified with Vent DNA Polymerase (NEB) following the standard thermal cycle and extension time of 60 seconds per kilobase. Linearized PCR fragments were isolated through 5% agarose gel filtration and the NucleoSpin Extract II (Clonetech) purification kit. Alternatively, restriction enzyme digestion was used when appropriate to linearized DNA fragments as described in the In-Fusion protocol.

Essentially, two linearized fragments are desired: the vector which typically contains the new plasmid and the insert to be placed into that plasmid. The vector and insert are designed such that 15 base pairs on each end perfectly match. The In-Fusion enzyme then anneals the insert and vector to create a final plasmid. The In-Fusion reaction follows the recommended protocol and 2.5 µL is transfected into 50 µL DH5α cells and plated onto LB-agar with appropriate antibiotic. Again >90% of the colonies typically contain the designed insert.

LacI Repressor Purification

LacI repressor constructs were cloned into a pBAD expression vector which controls expression of a gene using the arabinose repressor system. All repressor constructs were inserted into the multiple cloning site (MCS) of the pBAD vector and given a 6×-Histidine tag on the C-terminus. Cloning was achieved using in-fusion. Purification begins by first transforming the desired plasmid into BL21 (DE3) cells and plating onto LB supplemented with ampicillin and incubating overnight at 37 C. The plate is used to innoculate 100 mL 2×YT medium (Sigma) supplemented with ampicillin in the morning. Many colonies (>100) are picked in the innoculation to prevent any potential bias from selecting a single colony. This starter culture is incubated at 37° C. with shaking (~200 RPM) for 3-4 hours until the flask grows past the mid-log phase and approaches the stationary phase (optical density at 600 nm (OD600) >1.0). 10 mL of the starter culture is then used to innoculate 1 L 2×YT medium supplemented with ampicillin. The large culture is incubated at 37° C. with shaking (~200 RPM) until early mid-log growth phase (OD600=0.3-0.4). At this point, the incubator temperature is reduced to 15° C. to slow bacterial growth. Expression is also induced at this point by adding 10 mL of 20% v/v arabinose that has been sterile filtered. The liquid culture is allowed to grow overnight (~16 hours).

In the morning, the culture is removed from the incubator and placed into 1 L centrifuge flasks. The cells are centrifuged at 5000 g for 10 minutes at 4° C. to pellet the cells. The supernatant is removed and cells are resuspended 20 mL in Nickel Lysis Buffer (300 mM NaCl, 50 mM NaH2PO4, pH 8.0). Cells are lysed using three passes through a cell homogenizer (Avestin) at ~18,000 PSI and whole cell lysate is immediately stored on ice. Lysate is then centrifuged at 15,000 g for 15 minutes at 4° C. to separate soluble protein from insolubate cell lysates. Supernatant is filtered through filter paper (Whatman #3) at 4° C. to remove further insoluble materials. A sample of the supernatant is collected for analysis on an SDS-PAGE gel.

A His-tag purification column is prepared by loaded 2 mL His60 Ni Superflow Resin (Clontech) into a Flex-Column (Kontes) fitted with a stopcock to regulate flow rate through the column. All work with the his-tag column is undertaken in refrigeration at 4° C. Resin is first equilibrated with 20 mL cold Nickel Lysis Buffer and the stopcock is set to very slowly drip out the buffer such that the nickel beads will form an equilibrated bed of beads. Filtered supernatant is then carefully added to the column and flow again is set to very slowly drip. A sample of the flow through is collected for SDS-PAGE gel analysis. The beads are then washed three times with Nickel Wash Buffer (50 mM NaH2PO4, 300 mM NaCl, 20 mM Imidazole, 2.5% v/v glycerol, pH 8) and samples of each wash are collected for SDS-PAGE gel analysis. His-tagged lacI repressor is then eluted from the column using Nickel Elution (50 $NaH_2PO_4$, 300 mM NaCl, 250 mM Imidazole, 2.5% v/v glycerol, pH 8) and elutant was collected. A sample of elutant was saved for SDS-PAGE gel analysis.

Nickel elutant is then buffer exchanged using an Amicon Ultra centrifuge filter with a 30,000 molecular weight cutoff (Millipore). Elutant is centrifuged at 5,000 g for 15 minutes at 4 C and the filter flow through is discarded. Typically, depending on yield, 200-300 µL concentrated protein remains above the filter. Protein is carefully resuspended in ~3-4 mL ice-cold Gel Filtration (GF) Buffer (200 mM Tris pH 7.4, 200 mM KCl, 10 mM EDTA, 3 mM DTT). Buffer replaced in this fashion reduces the initial buffer to about 7% of its starting concentration. Buffer is replaced three times resulting in <0.1% of the elutant buffer remaining. Protein is then concentrated a final time to achieve a protein concentration in the 1-10 mg/mL range as measured using absorbence at 280 nM (A280) on a spectrophotometer (Nano-Drop).

Purified protein can be saved at this step by flash freezing the protein in liquid nitrogen and storing at −80° C. All samples from the nickel purification are boiled in LDS sample buffer (Expedeon) for 10 minutes and run on a 4-12% SDS-PAGE gel (Expedeon) at 110V for 1 hour. Protein for in vitro transcription assay underwent a size exclusion chromatography step. His-tag purified lacI repressor in GF buffer was concentrated and loaded onto a Hi Load 16/60 Superdex 75 column and sample was driven by Akta Prime FPLC. Fractions were collected and samples were SDS boiled and run on SDS-PAGE gels to determine purity.

Protein was concentrated again using centrifugal 30,000 MW filter and stored in GF buffer. Protein was flash frozen and store at −80° C.

Prokaryotic GFP and YFP Regulation Assays

GFP Regulation Assay

EPB229 cells were co-transformed with a lacI repressor plasmid providing chloramphenicol resistance and a reporter plasmid providing ampicillin resistance and plated onto LB agarose plates with ampicillin and chloramphenicol. Plates were incubated overnight at 37° C. and stored at 4° C. The repressor plasmids are all derived from pABD34 plasmid and constitutively express the lacI gene using its native promoter from E. coli. The lacII sequence has 10 C-terminal residues truncated to prevent tetramerization. Point mutations to the lacI sequence made using inverse PCR mutagenesis. For repressor quantification experiments a C-terminal mCherry tag was inserted using in-fusion cloning.

Reporter plasmid were derived from the pBR plasmid and have a reporter gene, Green or Yellow Fluorescent Protein (GFP or YFP), under control of the native LacZ/Y/A promoter. The operator sequences of the promoter used were:

```
O1:
                                        SEQ ID NO: 6
5' AA TT GTG AGC G GAT AAC AA TT 3'

Lsym:
                                        SEQ ID NO: 9
5' AA TT GTG AGC GCT CAC AA TT 3'
```

In the original assay, only GFP was monitored. Single colonies were picked into 1 mL LB supplemented with ampicillin and chloramphenicol and grown ~16 hours at 37° C. with shaking (~200 RPM). 100 µL of the sample aliquoted into a 96-well clear bottom plate (Corning) and OD600 and fluorescence (excite: 488 nm, emit: 525 nm) were measured on Infinite M1000 plate reader (Tecan). Samples to be assayed are typically picked in triplicate. Fluorescence is normalized by OD600 and averaged across replicates.

YFP and mCherry E. Coli Regulation Assay

The self-regulated reporter plasmid included the O1 operator sequence (5'-AA TT GTG AGC G GAT AAC AA TT-3' SEQ ID NO: 6) followed by yellow fluorescent protein (YFP), an ampicillin (AMP) resistance sequence and a 15 base pair spacer (5'-AAT TCA GGG TGG TGA-3' SEQ ID NO: 10), followed by the lacI repressor. A C-terminal mCherry tag was added to the lacI repressor gene after an 11 bp linker to create the LacI-mCherry construct.

We transformed the autogenously regulated reporter plasmid into EPB229 cells (F-Δ(lacI-lacA)::frt). These cells were derived from the MG1655 "wild type" line. Colonies were picked in triplicate into MOPS minimal media with 0.4% glucose, ampicillin and CAM and grown overnight at 37° C. with shaking. 50 µL of the overnight culture was used to inoculate 1 mL fresh MOPS minimal media supplanted with varying amounts of IPTG. We measured optical density at 600 nm (OD600), YFP fluorescence (excite: 510 nm emit: 535 nm), and mCherry fluorescence (excite: 585 nm emit: 610 nm) for all wells over a 12 hour period using a TECAN M1000 plate reader in 384 well optical bottom plates (Corning). In vivo data was normalized for growth by measuring cells in triplicate as they were growing. All data points collected were then fit to a 2nd order polynomial to obtain a curve which is fluorescence as a function of OD600. A positive control was established by co-transforming EPB229 cells with O1 YFP reporter and a CAM plasmid without LacmCherry (pABD34). YFP signal was normalized to the polynomial fit from the positive control. Final values for fitting were calculated for cells at approximately mid-log growth phase (0.4 OD600).

Native Gel Electrophoresis

We used the NativePage (Invitrogen) kit for native gel electrophoresis. The primary advantage of this kit is that it is based upon Blue Native Polyacrylamide Gel Electrophoresis (BN Page) which uses Coomassie G-250 as the molecule to provide charge shift for proteins. Coomassie G-250 binds to proteins providing a net negative charge without denaturing the protein.

Lac repressor was purified and was mixed in non-denaturing sample loading buffer. 10 µL of samples and NativeMark (Invitrogen) protein standard were added to wells of NativePage 4-16% Bis-Tris Gels. Gels were loaded within Novex Mini-cell (Invitrogen) gel running boxes. The interior (between the gels) was filled with NativePage cathode running buffer which contains Coomassie G-250. The exterior was filled with NativePage anode running buffer. Gels were run at 150V for 2 hours, then removed. Gels were placed in Fix (40% methanol, 10% acetic acid), microwaved on high for 45 seconds, and then shaken on an orbital shaker for 15 minutes to fix the gel. The gels were then switched to Destain (8% acetic acid), microwaved on high for 45 seconds, and placed on an orbital shaker overnight to remove any unbound Coomassie G-250. Gels were then imaged.

Eukaryotic Gene Regulation Assays

All gene regulation assays start by transiently transfecting the cell line of choice with the appropriate plasmid. Media is supplemented with effector of varying concentration in wells (IPTG for lacI repressor experiments and doxycycline for tet repressor experiments) and specific experimental conditions are typically grown side by side in triplicate. Experimental measurement times varied depending upon cell confluence but occurred 24 to 72 hours after transfection.

Fluorescence Microscopy

Fluorescence microscopy was performed in several different ways. For live cell microscopy, cells were grown as previously described. Media was switched to phosphate buffered saline (PBS) to reduce auto-fluorescence and cells were imaged on a Nikon Eclipse TE2000-U inverted microscope equipped with green and blue filters and a Nikon Intensilight C-HGFI power source. High resolution fluorescence microscopy was also performed by growing cells in the Lab-Tek II 8 well Chamber Slides system (Nunc) and cells were stained with 4',6-diamidino-2-phenylindole (DAPI). Slides were viewed on the Zeiss AX100 microscope with an X-cite series 120Q light source.

Bulk Fluorescence Assays

Quantitative fluorescence data was achieved by measuring the bulk properties of eukaryotic cells. Two assays were developed which were shown to give approximately the same result. Cells were lysed with Reporter Lysis Buffer (Promega) and fluorescent emission was read on the Tecan M1000 with the following excitation/emission wavelengths: GFP excite: 485 nm and emit: 510 nm; YFP excite: 510 nm and emit: 535 nm; and mCherry excite: 585 nm and emit: 610 nm. Second, entire cell culture plate was scanned on the Typhoon scanner using a 473 nm blue excitation laser to excite GFP and the >520 nm filter to read emission. Images were analyzed using ImageJ (NIH).

Luciferase Assay

Cells were lysed with Reporter Lysis Buffer (Promega) and 5 µL of whole cell lysate was added to 45 µL of luciferase assay buffer (Promega) containing luciferin in 384 well optical bottom plates (Corning). Plates were immediately loaded into the Tecan M1000 and luciferase signal was measured for each well over time. Peak luciferase signal values were used for quantification.

Western

Whole cell lysate is then mixed with 4×LDS sample buffer (Expedeon) and boiled at 70° C. for 10 minutes to denature the proteins. Samples were loaded into wells of 10-20% SDS-PAGE gels (Expedeon) and electrophoresed at 110V for 1 hour using the RunBlue SDS Running Buffer (Expedeon). Gels were removed and washed with MilliQ water and then prepared for semi-dry transfer to Immobilon-P transfer membrane (Millipore). Gels were soaked for 10 minutes in western transfer buffer (25 mM Tris, 200 mM glycine, 10% methanol). Transfer membrane is placed in 100% methanol for 15 seconds, moved to MilliQ for 2 minutes, and then to western transfer buffer for 5 minutes. Six pieces of 3 mm filter paper (Whatman) are also soaked in western transfer buffer. The transfer stack is prepared as follows: 3 pieces filter paper-equilibrated PVDF transfer membrane-equilibrated gel-3 pieces filter paper. The sandwich is then loaded onto the semi-dry transfer plates and run at 15V for 15 minutes.

PVDF membrane is then removed from the sandwich and blocked in Blotto (1 g non-fat powdered milk in 20 mL PBS-T (PBS with 0.1% Tween-20)) for 1 hour. Membrane was then washed three times for 10 minutes each with PBS-T. Membrane was then placed in the primary antibody at 4 C overnight on an orbital shaker. The buffer and concentration of primary antibody were determined by the manufacturers recommendation for each antibody. In the morning, the gel was washed three times with PBS-T and placed in the appropriate secondary antibody conjugated to horseradish peroxidase (HRP). The gels were then exposed to chemiluminescent substrate specific to HRP and imaged.

Animal Studies

All animal work was conducted according to relevant national and international guidelines and steps were taken to be sure there was minimal suffering. Studies were approved by the University of Pennsylvania Institutional Animal Care and Use Committee (IACUC #805057).

AAV Injection

Subretinal injections were performed as described[5] in a cohort of 2-4 month old CD-1 mice at a dose of 1×10$^9$ vg/retina. Contralateral eyes were used as uninjected controls. Animals were anesthetized with isoflurane and injections were monitored by direct visualization through the dissecting microscope. Tail vein injections were performed under direct visualization using a dose of 1×10$^{10}$ vg in a volume of 0.15 mL.

Transgene Expression

Inducer (IPTG) was given by oral gavage with a dose of 15 µM in a volume of 0.1 mL. Imaging was carried out after sedation with ketamine/xylazine using a Xenogen imager. Luciferin (150 mg/kg) was injected IV immediately prior to imaging.

Modeling

All functions from text were coded into Matlab (Mathworks) scripts to calculate the MWC model outputs. Standard linear regression minimization functions were used to minimize the difference between experimental and theoretical curves in order to fit for the thermodynamic parameters of interest. Various minimization schemes were used and all were built in Matlab functions such as a genetic algorithm and direct-pattern search. The error estimates in fit parameters were done by a monte carlo approach. Each individual data point had some random fraction of its error added to it and the data was refit. This process was repeated >100 times and then the standard deviation of the individual parameters was taken to be the error in that fit parameter. The best fit to the data without error added was taken to be the reported value for the individual parameters.

Plasmid Maps

Various plasmids were used in the development of the expression cassette and AAV vectors described herein.

Prokaryotic Plasmids pBR series reporter plasmids were derived from giving ampicillin resistance and strict plasmid copy number of approximately 10-20 per cell. The reporter cassette contains the natural lacZ/Y/A promoter from the lacI operon of *E. coli*. Only one operator is present in the plasmid and is located downstream of the promoter in the transcriptional initiation region. Regulated genes downstream of the promoter included eGFP, YFP and the polycistronic message of dimeric lacI repressor-mCherry fusion followed by YFP. An 18 base pair spacer which was the 18 base pairs that preceding the lacI-mCherry gene, had the sequence: 5' CAA TTC AGG GTG GTG AAT 3' SEQ ID NO: 11.

The pLacI series of plasmids provide chloramphenicol resistance and constitutive lacI repressor from the natural lacI promoter of *E. coli*. The lacI gene has the 11 C-terminal codons truncated. The/ad repressor-mCherry fusion includes an 18 base pair linker with the sequence: 5' GGC TCA GGT CTC GAG TTG 3' SEQ ID NO: 12. The arabinose expression plasmid is pBAD-DEST-49 (Invitrogen) and expression genes were placed within the first multiple cloning site.

Eukaryotic Plasmids

The pIRES plasmid (Clontech) has a minimal CMVI promoter with two multiple cloning sites linked by the IRES sequence. The original IRES plasmid put YFP in the first multiple cloning site and EuLacmCherry in the second multiple cloning site. The EuLac sequence was taken from the codon optimized sequence for Eukaryotic cells with the splice site fixed[15]. We first used a dimeric EuLac sequence with the 11 C-terminal codons removed. Later we used the EuLacTet sequence with the 11 C-terminal codons of wild type lacI restored for tetrameric lacI repressor. The following is the EuLacTet sequence with the 11 C-terminal amino acids that result in tetramerization highlighted in bold:

```
                                      SEQ ID NO: 13
5'-ATG AAA CCA GTA ACG TTA TAC GAC GTC GCA GAG

TAT GCC GGT GTC TCT TAT CAG ACT GTT TCC AGA GTG

GTG AAC CAG GCC AGC CAT GTT TCT GCC AAA ACC AGG

GAA AAA GTG GAA GCA GCC ATG GCA GAG CTG AAT TAC

ATT CCC AAC AGA GTG GCA CAA CAA CTG GCA GGC AAA

CAG AGC TTG CTG ATT GGA GTT GCC ACC TCC AGT CTG

GCC CTG CAT GCA CCA TCT CAA ATT GTG GCA GCC ATT

AAA TCT AGA GCT GAT CAA CTG GGA GCC TCT GTG GTG

GTG TCA ATG GTA GAA AGA AGT GGA GTT GAA GCC TGT

AAA GCT GCA GTG CAC AAT CTT CTG GCA CAA AGA GTC

AGT GGG CTG ATC ATT AAC TAT CCA CTG GAT GAC CAG

GAT GCC ATT GCT GTG GAA GCT GCC TGC ACT AAT GTT

CCA GCA CTC TTT CTT GAT GTC TCT GAC CAG ACA CCC
```

```
                                           -continued
ATC AAC AGT ATT ATT TTC TCC CAT GAA GAT GGT ACA

AGA CTG GGT GTG GAG CAT CTG GTT GCA TTG GGA CAC

CAG CAA ATT GCA CTG CTT GCG GGC CCA CTC AGT TCT

GTC TCA GCA AGG CTG AGA CTG GCC GGC TGG CAT AAA

TAT CTC ACT AGG AAT CAA ATT CAG CCA ATA GCT GAA

AGA GAA GGG GAC TGG AGT GCC ATG TCT GGG TTT CAA

CAA ACC ATG CAA ATG CTG AAT GAG GGC ATT GTT CCC

ACT GCA ATG CTG GTT GCC AAT GAT CAG ATG GCA CTG

GGT GCA ATG AGA GCC ATT ACT GAG TCT GGG CTG AGA

GTT GGT GCA GAT ATC TCG GTA GTG GGA TAC GAC GAT

ACC GAA GAC AGC TCA TGT TAT ATC CCG CCG TTA ACC

ACC ATC AAA CAG GAT TTT CGC CTG CTG GGG CAA ACC

AGC GTG GAC CGC TTG CTG CAA CTC TCT CAG GGC CAG

GCG GTG AAG GGC AAT CAG CTG TTG CCA GTC TCA CTG

GTG AAG AGA AAA ACC ACC CTG GCA CCC AAT ACA CAA

ACT GCC TCT CCC CGG GCA TTG GCT GAT TCA CTC ATG

CAG CTG GCA CGA CAG GTT TCC CGA CTG GAA AGC GGG

CAG-3'
```

The operator was placed within the CMV\IE\Promoter region of the minimal CMV promoter 13 base pairs downstream of the TATA box. The following is the sequence of the CMV\IE\Promoter region including the Lsym operator in bold:

```
                                          SEQ ID NO: 14
5'-CGC CCC GTT GAC GCA AAT GGG CGG TAG GCG TGT

ACG GTG GGA GGT CTA TAT AAG CAG AGC TCG AAT TGT

GAG CGC TCA CAA TTG AGC TCG TTT AGT GAA CCG TCA

GAT C-3'
```

Figure 4:
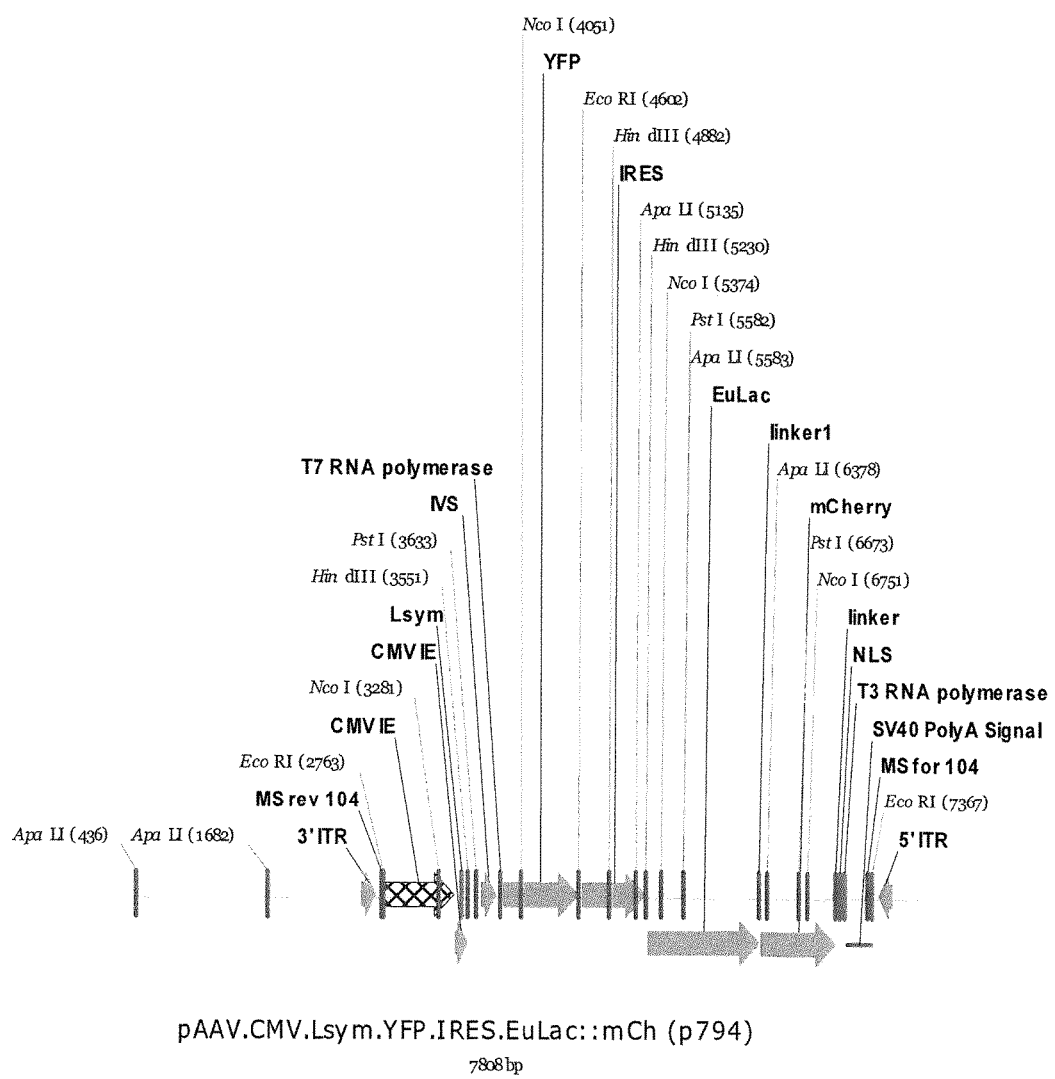
FIG. 4 is a plasmid map of p794 which is pAAV.CMV-.Lsym.YFP.IRES. EuLac::mCH SEQ ID NO: 1. This plasmid contains an autogenous gene expression cassette containing the minimal CMVI promoter under control of the Lsym operator, the YFP reporter gene separated by an IRES sequence from the lac repressor sequence, which was C-terminally tagged with mCherry to quantify the lac repressor concentration in cells. The plasmid co-expresses YFP and the lac repressor fused to mCherry, separated by an IRES sequence.

The plasmid map of pAAV.CMV.Lsym.YFP.IRES.EuLac::mCh is shown in FIG. 4. The entire cassette is flanked by ITR repeat regions for inclusion into AAV-viral capsids. The nucleic acid sequence of that plasmid is given in FIG. 5 SEQ ID NO: 1.

Figure 6:
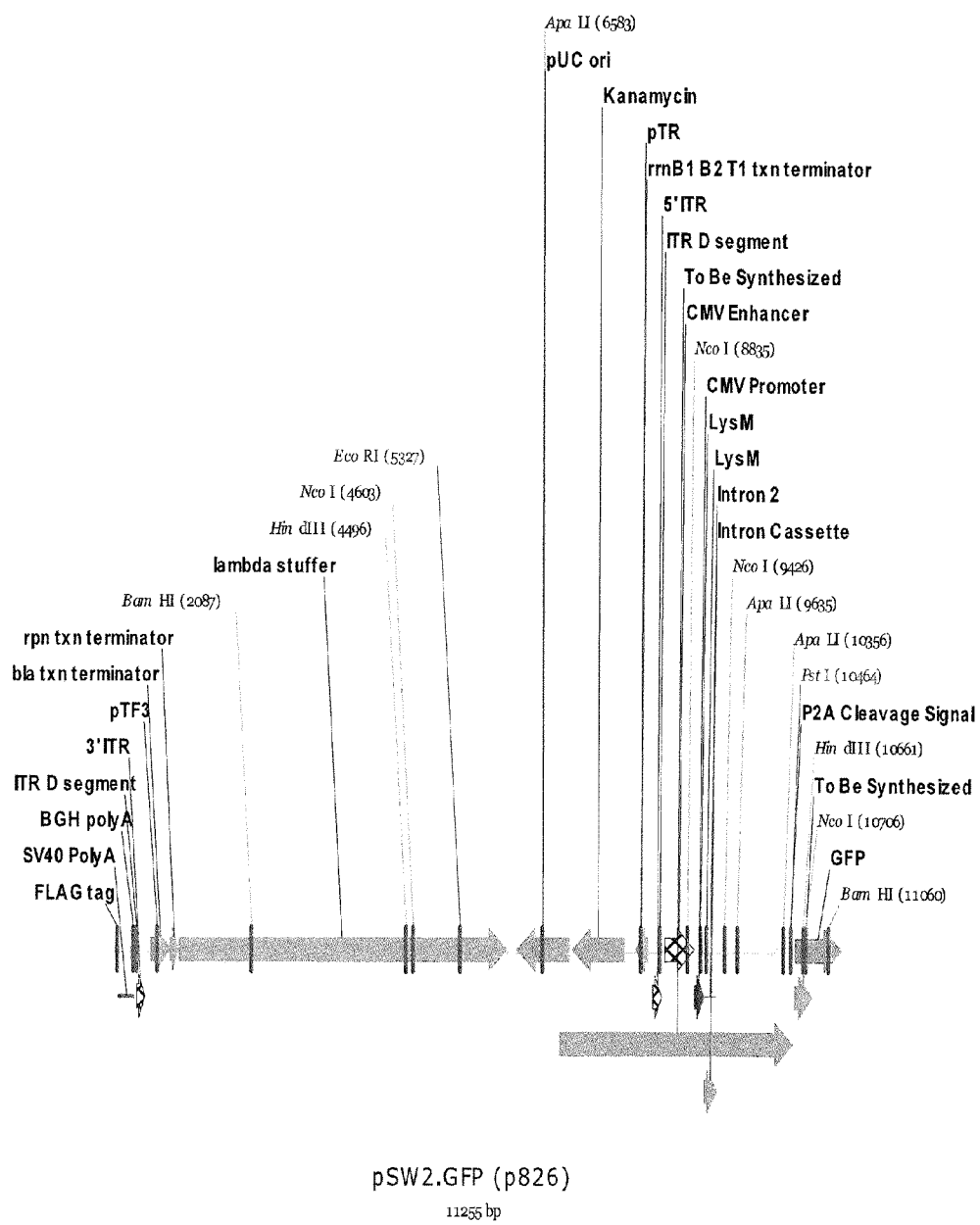
FIG. 6 is a design for a pSW-GFP plasmid map, p826 SEQ ID NO: 2. The CMV promoter in this plasmid has two Lsym (LysM) sites and a 2A sequence separating the lacI repressor from the GFP reporter gene.

The pSW plasmid that expresses EuLac followed by the 2A sequence followed by the GFP gene is shown as a plasmid map in FIG. 6. The entire cassette is flanked by ITR repeat regions for inclusion into AAV-viral capsids. The nucleic acid sequence of that plasmid is given in FIG. 7 SEQ ID NO: 2.

Example 2—Inducible Transgene Regulatory Systems (ITRS)

An ITRS was constructed for use in AAV using the control elements of the bacterial lacI operon. We have demonstrated that the allosteric properties of the lacI repressor can be tuned to improve transgene regulation. The repressor binds tightly to its operator as well as cooperatively to ancillary sites which can potentially lower basal levels of expression.

A variety of switches were studied. We first made an autogenously regulated lacI genetic switch by placing the lacI gene fused to mCherry after the natural lacI promoter. A reporter gene, YFP, was included after an 18 base pair spacer. Prokaryotes are capable of expressing a poly-cis-tronic message where multiple genes are expressed off of a single promoter (which is how the lacZ, lacY, and lacA genes are naturally expressed), therefore we expected this single plasmid to make both a lacI repressor-mCherry fusion protein and the YFP reporter gene. The native lacZ/Y/A promoter under control of the O1 natural lacI operator controls two genes: lacI repressor fused to mCherry and YFP. Lac-mCherry binds to O1 leading to autoregulation and the YFP acts as a cytoplasmic readout of the switch.

The autogenously regulated prokaryotic switch was tested in EPB229 cells growing in minimal media supplemented with glucose. Both mCherry and YFP were measured in living cells. The autogenously regulated lacI genetic switch successfully turns off YFP expression and induces to a lower value than the constitutive lacI genetic switch (data not shown). Essentially, the autoregulation diminishes the overall dynamic range of the prokaryotic switch, which is expected because the promoter that drives the lacI repressor in *E. coli* is well tuned to have a maximal dynamic range switch. Autoregulation also regulates the lacI repressor (data not shown). The induction is much less than what is seen for YFP. The calculated lacI repressor concentration from the autogenously regulated switch is actually much higher than was measured from the constitutive plasmid.

The reporter operator is much stronger than the natural lacI promoter that makes constitutive lacI repressor. The autogenously regulated stronger promoter actually makes more repressor than the constitutive weak promoter. That is why leakiness is not greater in the autogenously regulated as expected. Alternatively, there is so much repressor that the switch cannot turn fully on. Clearly the strength of the promoter that is being autogenously regulated plays a significant role in the functional output of the genetic switch.

The first generation of autogenous only repressed half of the constitutive level. In order to address this, point mutations were made in the lacI repressor of SEQ ID NO: 3 to decrease the leakiness of the switch or to increase the dynamic range. We tested both the DNA binding domain mutants (Q18A and Q18M) and effector pocket mutants (F161S, F161W, Q191K and Q291M) on the autogenously regulated lacI genetic switch in prokaryotes. The two DNA binding domain mutants clearly follow the same phenotypic changes seen in the constitutive switch therefore we can change leakiness and dynamic range by mutating the DNA binding domain. The effector pocket mutants also exhibited changes in leakiness and dynamic range.

The second generation of switch was created as follows: To evaluate autogenous regulation in mammalian cells, we created an inducible CMV promoter to regulate the synthesis of a bi-cistronic message by inserting a symmetric lacI operator between the TATA box and the transcription start site. This bi-cistronic message codes for both the repressor and reporter, separated by either Internal Ribosomal Entry Sequence (IRES) or the smaller 2A sequence. For a frame of reference, we also created a bi-directional vector by constitutively expressing the repressor.

We next sought to test the autogenously regulated lacI repressor in transiently transfected HEK293T cells to test its ability to regulate a reporter gene. We first developed a plasmid that has the minimal CMVI promoter with the Lsym lacI operator between the TATA box and the transcription start site. Eukaryotes do not translate poly-cistronic mRNA messages so an alternative strategy is needed to express the two genes. We first used an Internal Ribosomal Entry Sequence (IRES) that allows the ribosome to translate a second gene within the mRNA and therefore make an autogenously regulated switch. We used YFP as the reporter gene and the lacI repressor sequence was the codon optimized sequence corrected for a splice site, which we term EuLac, which was then fused to the mCherry[15]. The EuLac::mCherry fusion has the canonical nuclear localization sequence (NLS) on the C terminus to localize the repressor to the nucleus.

We next developed a minimal length cassette with the goal of using it in an AAV viral delivery vector. This cassette again uses the same minimal CMV I promoter with a Lsym operator DNA sequence. The gene order has been switched so the EuLac gene is first, followed by the 2A sequence, followed by GFP as the readout. Extraneous DNA was trimmed and unique restriction enzyme cleavage sites were designed around every gene in the cassette for easier downstream cloning. The same plasmid was made with luciferase as the readout gene.

One lacI repressor construct we used has the 11 C-terminal residues of the lacI repressor truncated to create a dimeric repressor. We have used a dimeric repressor in previous switches. We sought to restore the tetramerization domain and multiple operator DNA sequences to restore the allosteric of lacI repressor to two DNA operators. First, we cloned a second Lsym operator DNA sequence 92 base pairs downstream of the first Lsym site. We transiently transfected dimeric lacI repressor with one Lsym operator (pSW-Luc) and dimeric lacI repressor with two Lsym operators (pSW-Luc Lsym x2) into ARPE-19 cells and assayed for luciferase with and without IPTG (data not shown). The addition of a second operator decreased both leakiness and maximal expression.

Next, the 11 C-terminal residues (nucleotides acids encoding aa 3530-360 of SEQ ID NO: 3) were re-inserted into the EuLac gene to make EuLacTet to make the pSW2-Luc/GFP plasmids. This gene still has the 11 amino acid linker and NLS sequence following the full lacI repressor itself, and the partial 2A protein appended to the C-terminus. We first wanted to see if the EuLacTet protein could form tetramers after 2A breakage. We cloned the EuLacTet with a 6x Histidine tag (His-tag) into our standard pBAD expression vector and followed the standard lacI repressor purification protocol. We also purified the original construct without the 11 C-terminal insertion which should be dimeric. These putative dimeric and tetrameric proteins were run on a native electrophoresis gel where oligomeric state is preserved and stained for protein. The native gel confirmed that the tetrameric protein ran at twice the molecular weight of the dimeric protein.

Example 3—Testing an Autogenously Regulated Laci Genetic Switch in E. Coli

We first verified that the lac repressor can autogenously regulate a gene of interest in E. coli. Bacteria have many natural autogenous gene regulatory circuits and will express multiple mRNAs from a single promoter if they are linked in cis with short DNA spacer elements.[25]

We made an autogenous switch by taking the lac repressor gene and linking it, with a 21 base pair space, after the YFP reporter gene. The lac repressor sequence was C-terminally tagged with mCherry to quantify the lac repressor concentration in the cells. The constitutive and autogenous switches were transformed into EPB225 bacteria, which lack the native lac operon, and YFP and mCherry fluorescence were measured as a function of IPTG concentration in the media.

Both the constitutive and autogenous switches repressed YFP expression in the absence of IPTG and showed full induction at low mM IPTG concentrations (data not shown). As expected, the autogenous switch also showed increased mCherry signal upon induction as expression of the lac repressor is also induced; the constitutive switch showed no significant increase in mCherry signal (data not shown). Thus, the autogenous lac genetic switch is functional in E. coli.

Figure 1B:
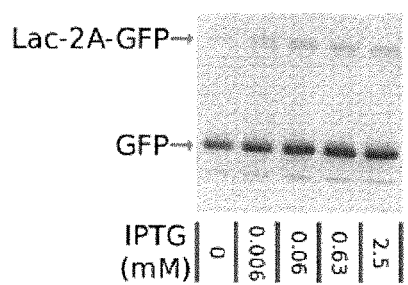
FIG. 1B is a Western gel analysis that provides a preliminary assessment of the autogenous regulatory system, showing that approximately 90% of protein product was correctly split by the 2A sequence in the cassette.
Figure 1C:
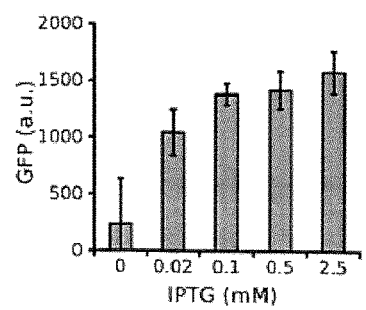
FIG. 1C is a bar graph showing that the cassette demonstrated a rheostat-like dose response to isopropylthio-β-galactoside (IPTG) that agrees with the autogenous regulation in E. coli.

Example 4—Testing an Autogenously Regulated lacI Genetic Switch in Mammalian Cells Next we established that the lac autogenous switch appropriately regulates gene expression in mammalian cells. We used a lac repressor gene (synlacI) which has been demonstrated to be capable of constitutive regulation in mice[15,30]. This gene includes a C-terminal nuclear localization sequence (NLS) to target the repressor to the nucleus. We verified that the lac repressor correctly localized to the nucleus by fusing mCherry to the C-terminus and visualizing mCherry localization through fluorescent microscopy (figure not shown). We next created a minimal length autogenous regulatory cassette for use in AAV (FIG. 1A). It is capable of accommodating a transgene up to approximately 2400 base pairs in an AAV vector. This cassette has the minimal CMV with a symmetric lac operator (Lsym) between the TATA box and the transcription start site and a second Lsym placed 92 base pairs downstream in order to facilitate cooperative binding of the lac repressor tetramer. We verified that the synlacI gene does form a tetramer using native gel electrophoresis (data not shown). We co-expressed a transgene (either firefly luciferase or GFP) by linking synlacI and the transgene with a 2A sequence. This spontaneously splits into two separate proteins as it is being transcribed by the ribosome (Trichas et al, 2008). We used anti-GFP western analysis to show that approximately 90% of protein product was correctly split by the 2A sequence (FIG. 1B). We also showed that the cassette demonstrated a rheostat-like dose response to IPTG that agrees with the autogenous regulation in E. coli (FIG. 1C).

Figure 1D:
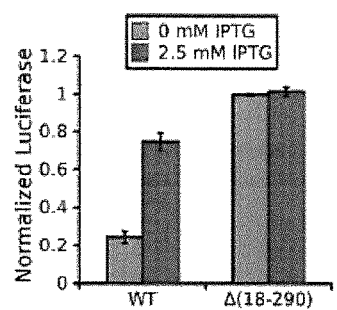
FIG. 1D is a bar graph indicating that transfection into human retinal pigment epithelium (ARPE-19) cells showed approximately 20% basal expression with a 3.5-fold induction ($p<0.05$). Expression of luciferase did not change with IPTG induction with the modified lac repressor (i.e. unregulated expression).

The plasmid containing the cassette controlling luciferase was transfected into human retinal pigment epithelium (ARPE-19) cells and grown with and without 2.5 mM IPTG. We measured approximately 20% basal expression with a 3.5-fold induction ($p<0.05$) (FIG. 1D).

To determine that the full length lac repressor is responsible for the signal change, we made a deletion in the lac repressor from amino acids 18-290. We saw high expression of luciferase which did not change with IPTG induction with this modified lac repressor (i.e. unregulated expression) (FIG. 1D). These data demonstrate that the autogenous lac genetic switch is functional in eukaryotic cell culture and that mutations in this sequence can eliminate its function.

HEK293T cells were transiently transfected with either: (1) the original autogenous IRES plasmid, (2) the new autogenous 2A plasmid, or (3) a constitutively expressed GFP under control of the chicken β-actin (CBA) promoter. Cells were grown in varying concentrations of IPTG and whole cell lysate was harvested for western. We performed a western with α-GFP antibodies. The original plasmid only has a single band for YFP (which is also detected with α-GFP) which induces ~2-fold with IPTG. The autogenous 2A plasmid has three primary bands: the highest band corresponds to lacI::2A::GFP fusion protein, the middle band is truncated 2A fused to GFP, and the third band is likely a degradation product. Comparing the highest band to the middle band we estimate ~90% breakage of the fusion protein to separated lacI repressor and GFP. We also see induction of GFP with increasing IPTG, again approximately 2-fold.

We demonstrated that an autogenously regulated lacI genetic switch functioned in both *E. coli* and three different eukaryotic cell types in cell culture (HEK293T, Cos-7, and ARPE-19). We found that our first generation of eukaryotic autogenous lacI switches were not ideal; we measured 45% leakiness and only 2-fold induction. Addition of a second operator DNA site downstream of the promoter decreased leakiness. Restoration of the tetramerization domain of the lacI repressor marginally increased dynamic range while maintaining the decreased leakiness. The Q18M mutation of lac I SEQ ID NO: 3 in the DNA binding domain decreased leakiness at the expense of maximal expression; Q18M functions has the same phenotype in *E. coli*. The F161W mutation decreased leakiness and increased dynamic range in the dimeric lacI repressor but may not function the same for the tetrameric lacI repressor.

These two regulatory systems were evaluated in cell culture by measuring production of reporter (GFP) and repressor fused to mCherry in HEK 293T cells. As we observed in bacteria, both the reporter and repressor are inducible. The GFP is dispersed throughout the cell while the mCherry signal is localized to the nucleus (data not shown). Both regulatory circuits produce similar basal levels of reporter transcript and the most noticeable difference is minimal basal synthesis of the repressor in the un-induced state. The utility of this regulatory circuit was also evaluated in COS-7 and ARPE-19 (Retinal Pigment Epithelial) cells, which produced similar results, suggesting there is not a cell specific bias. In cell culture, the autogenously regulated switch appears to have many of the advantageous characteristics for an ITRS.

An ITRS should have minimal leakiness. In order for the self-regulating system to have the same dose response profile, a tighter binding repressor is needed. We have identified many mutated repressors that bind more tightly to the operator and will decrease the leakiness and restore optimal function. Furthermore, the use of multiple DNA operator sites and a tetrameric lacI repressor could were found to decrease the leakiness of the switch and increase the dynamic range.

We reduced basal expression and improved repression by incorporating a second operator sequence or by increasing the binding affinity of the repressor for its operator. In bacteria, lacI repressor binds to an operator immediately downstream of its promoter as well as to an ancillary site either located 93 bp upstream or 401 bp downstream from the start of transcription. When the tetrameric repressor binds to the primary and one of the ancillary operators levels of repression increase 40-70-fold[11]. The second operator increases operator occupancy of the primary operator.

We introduced an ancillary operator ($O_B$) 93 bp downstream of the $O_A$. The vector was transfected into HEK293T cells and induction profiles measured to evaluate the leakiness, dynamic range, and $E_{50}$. Unlike bacteria, these modifications produced a modest decrease in leakiness and marginal improvement of the induction. The potential cooperative effect was much less than has typically been seen in *E. coli*.

Point mutations introduced in the repressor can decrease leakiness, increase dynamic range, or change/alter the affinity for effector molecules in bacterial cells. A particular mutation, Q18M, decreases leakiness by improving operator binding while another mutant, F161W, decreases leakiness and improves dynamic range by altering the allosteric equilibria. These point mutations were introduced into the repressor and induction measured in ARPE-19 cells. Both mutant repressors displayed the same phenotype observed in *E. coli*. Q18M exhibited decreased leakiness as well as the commensurate decreased dynamic range; while F161W exhibited both decreased leakiness and increased dynamic range. These modifications allowed us to improve the regulatory properties of this ITRS.

In order to develop a minimal length cassette, extraneous DNA was trimmed and unique restriction enzyme cleavage sites were designed around every gene in the cassette for easier downstream cloning. Since the switch is autogenously expressed, it has 1) reduced immunogenicity: only minimal lacI repressor concentration is needed; 2) increased sensitivity: the switch is highly sensitive to its inducer (i.e. IPTG in our example); 3) the response to effector is faster; 4) highly stable; 5) tight regulation via point mutation at DNA binding site.

Example 5—Evaluation of Effector Molecule

An inducible regulatory system is only valuable for gene therapy if the effector molecule can penetrate the appropriate tissue and the intracellular concentration is sufficient to induce transgene expression.

Before carrying out comparative studies in mice, we wanted to test the autogenous lac genetic switch in living mice. Prior to this, we carried out pilot studies evaluating the bioavailability of the effector molecule, IPTG, after oral administration. Three mice were given a 10 mM oral gavage twice a day for 3 days. At the end of the third day, the animals were sacrificed and their organs harvested. The lysate from liver, kidney, skeletal muscle and neural retina was used to measure the steady state concentration of IPTG in those tissues. Levels were determined to be approximately 100 µM in each of the organs after comparison of expression generated reference levels of IPTG (data not shown). The lac repressor-IPTG $K_D$ is approximately 15 µM indicating that levels of IPTG reaching the different tissues after oral gavage are more than sufficient to induce the autogenous switch[48].

Example 6—In Vivo Studies

To evaluate this regulatory cassette in an animal model, AAVs with inducible expression employing the lacI repressors and operators as described are designed. Briefly, transcriptional cassettes (promoters, operators, transgene and polyadenylation signals) are inserted in ITR-flanked AAV cis constructs, thereby allowing them to be packaged into AAV particles. These constructs are co-transfected in HEK293 cells alongside an AAV8 packaging plasmid and an adenoviral helper plasmid in order to generate infectious AAV particles. The lysate and supernatant are purified according to established protocols on a density gradient and chromatography columns in order to obtain a high-titer vector.

Two in vivo settings are explored, i.e., hepatic targeted gene transfer and retinal targeted gene transfer approaches.

Administration to the retina provides data relating to CNS applications of this inducible self-regulating system. For that, we administer the vector in the subretinal space of the CD1 mice, a specialized technique successfully translated from mice to dogs, monkeys and most recently humans. We demonstrate the time course of reporter gene expression non-invasively both qualitatively (ophthalmoscopy) and quantitatively (luciferase imaging).

Figure 2A:
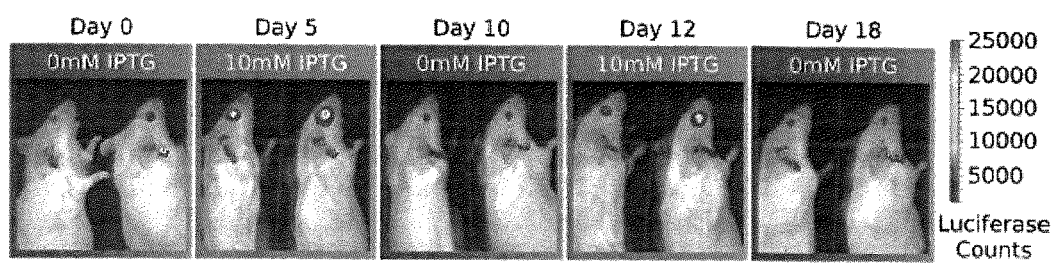
FIGS. 2A and 2B demonstrate reversible regulation mediated by the lac autogenous switch in the retina.

We tested the capability of the lac autogenous switch to reversibly regulate the reporter gene, firefly luciferase, in the retina after subretinal injection of the relevant AAV. Specifically, we packaged an ITR-flanked AAV cis construct (FIG. 4) into AAV particles using an AAV8 packaging plasmid and an adenoviral helper plasmid to generate infectious AAV particles. Nine adult mice were given unilateral (right) subretinal injections of autogenously regulated firefly luciferase in an AAV serotype 8 vector (AAV8.lac.ffLuc). The left eye of each mouse served as an uninjected, negative control. Two weeks post-injection, mice were given an intraperitoneal (IP) injection of the luciferase substrate, luciferin, and the left and right eyes of each animal were imaged (without providing the IPTG inducer) to establish a baseline level of luciferase expression (FIG. 2A). This baseline expression is significantly higher than background across the 9 animals reflecting leakiness associated with the autogenous regulation system ($p<0.05$).

Figure 2B:
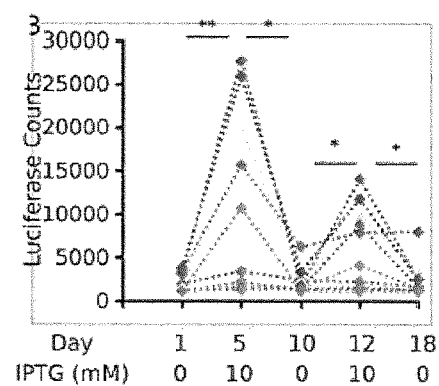

The mice were then subjected to repeated cycles of three days of IPTG oral gavage to turn on the switch followed by ≥5 days without gavage to allow the switch to return to the off state. The right (injected) eyes of the mice showed robust induction and return to baseline through two on/off cycles (FIG. 2A). The left control eyes did not luminesce above background (FIG. 2A). Quantification of the right eyes of the nine mice shows significant first induction ($p<0.01$), significant repression after IPTG is first removed ($p<0.05$), significant second induction ($p<0.05$), and significant return a repressed state after IPTG is again removed ($p<0.05$) (FIG. 2B). On average, an approximate 5-fold increase in signal was measured for the first induction which would indicate that the baseline level of expression is less than 20% of an equivalent un-regulated AAV vector. A preliminary evaluation of immunofluorescence staining for luciferase after the last induction is being conducted and the data evaluated. Preliminary results appear to show high levels of luciferase in retinal pigment epithelium (RPE) and photoreceptors, as would have been predicted about transgene expression after subretinal injection of AAV8. There is no luciferase present in the control (uninjected) eyes. (FIG. 3C).

Administration to the liver provides data on systemic applications of this system and expression is monitored by serial luciferase imaging studies.

Figure 3A:
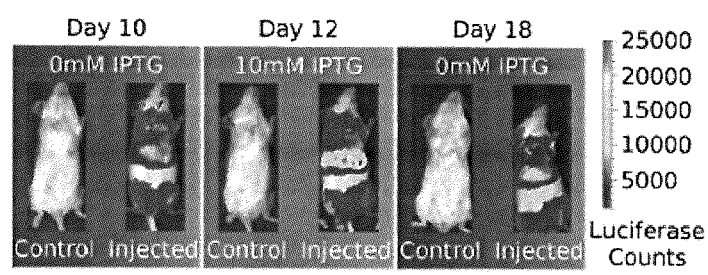
FIGS. 3A and 3B show reversible regulation mediated by the lac autogenous switch in the liver.
Figure 3B:
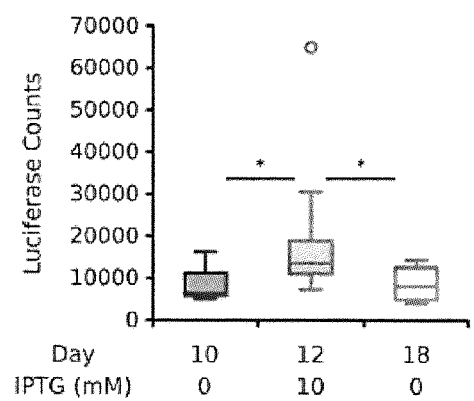

We also evaluated the same AAV vector delivered through tail-vein injection to 9 adult mice in order to assess function of this regulatory system in the liver. Four mice were given saline tail-vein injections to serve as negative controls. All animals were subjected to one on/off cycle through oral gavage of IPTG (FIG. 3A). Similar to the eye results, the quantification showed: (i) baseline expression revealing that the switch is inherently leaky ($p<0.01$); (ii) significant induction upon IPTG oral gavage in the liver ($p<0.05$); and (iii) significant return to baseline levels upon removal of IPTG ($p<0.05$) (FIG. 3B). The liver on average showed a two-fold change in luciferase signal upon induction. Histology results are pending and are expected to show luciferase in hepatocytes in the treated, induced animals, but no luciferase in control (PBS-injected) animals (FIG. 3C).

In another version of this experiment, immunocompetent CD1 mice receive $10^{11}$ GC AAV particles, administered via parenteral route (a tail vein intravenous injection). Three weeks after virus is administered the animals are imaged (Day 1), detectable but lows levels of luciferace is observed (accessed by non-invasive bioluminescence imaging). Similar levels are observed a week later.

On day 9, animals are gavaged a solution that contains the inducer, (IPTG) and production of the luciferase was again determined by non-invasive bioluminescence imaging (BLI). Gross anatomical localization of expression illustrates that the ITRS confined to the liver. Five days after being induced (day 13) the animals are again imaged and low detectable levels of luciferase were observed. On day fifteen, animals are again induced and luciferase bioluminescence increased dramatically. The switch is functional and quantitative measurements of transgene expression show that when induced, levels of luciferase increased 20-30-fold. Moreover, the switch can be cycled on and off. Although this ITRS exhibits some basal leakiness, it is immediately clear that the switch of the lac operon has the potential to regulate transgene delivery. The optimized autogenous switch functions from transductions of AAV virus encoding transgenes in cell culture and in living mice. The living mice are stably expressing the AAV-encoded luciferase nearly 1 month post infection and are capable of reversibly regulating the expression of luciferase in their liver.

In another experiment, we insert the cassette from the pSW2 plasmid which has two Lsym operators and tetrameric lacI into a plasmid which will make serotype 8-AAV virus. Virus was made at a virus core facility and confirmed to function in HEK293T cells. We performed tail-vein injections of 12 nude mice with SW2-Luc (same cassette as pSW2-Luc) virus (Multiplicity of Infection (MOI): $1 \times 10^{11}$) to target the liver.

The 12 mice were split into two cohorts of 6 to differentiate between time dependent changes in luciferase signal and IPTG dependent changes in luciferase signal. Noninjected mice were also included as a control and showed no measurable luciferase signal. Four mice died in the study, either due to complications with gavage or unknown circumstances. Of the remaining mice, two from each cohort appeared to have luciferase correctly targeted to their livers in the imaging. Many mice had significant luciferase signal in muscle tissue in the tail and surrounding region and were excluded from further analysis. Mice were fed sequential diets of either water or gavaged (force feeding) 1M IPTG. We previously confirmed that gavage of 1M ITPG provides concentrations of IPTG in excess of 100 µM in brain, retina, vitreous, muscle, liver, kidney, serum and urine.

Mice were given intraperitoneal (IP) injections of luciferin and scanned on a live animal imaging scanner throughout the experiment. All four animals have low but measurable levels of luciferase one month after the tail-vein injection. There is noticeable animal to animal variation. The mice were not age and gender matched and they were all given the same amount of viral vector regardless of weight which could account for some of the variation.

The first cohort were initially kept on a normal water diet throughout the first week. There is a ~2-fold increase in luciferase signal throughout this time. The second cohort were gavaged two times a day for three days; there is a potent increase (>20-fold increase) in luciferase signal in these two mice. All four animals have low but measurable levels of luciferase one month after the tail-vein injection. There is noticeable animal to animal variation with mouse #281 being particularly leaky. The mice were not age and gender matched and they were all given the same amount of viral vector regardless of weight which could account for some of the variation.

The first cohort was then gavaged with IPTG and saw a ~4-fold increase in luciferase. Meanwhile the second cohort was put back on regular water and saw a ~3-fold decrease in signal after 2 days and ~8-fold decrease after 6 days. Both cohorts were then re-gavaged with IPTG to re-induce and there was a wide range of luciferase signal increase from ~3-fold to ~30-fold. This re-induction confirms that the mice still have AAV infected cells capable of regulating luciferase signal through the lacI autogenous genetic switch.

In summary, transgene regulatory systems should: (i) maintain a low level of basal expression of the transgene; (ii) exhibit functional levels of transgene upon induction; (iii) have an inducing dynamic range that provides useful dose response control, i.e. the system should resemble a rheostat as opposed to an on-off switch; (iv) should be dynamic and respond quickly to changes in the effector concentration; (v) should respond to effector molecules that are orally active, small molecules with no effect on endogenous gene expression and minimal toxicity; (vi) should minimize potential immunogenicity; and finally (vii) if the transgene is to be delivered by AAV, then the regulatory system needs to be compact enough to fit (together with the transgene) into the AAV viral capsid.

The inducible trangene regulatory system described herein specifically addresses many of these concerns by using an autogenously regulated lac repressor to control transgene expression. By employing the lac repressor, the inventors have provided a regulatory system which is simple and compact consisting only of a 360 amino acid protein and 20-21 base pair DNA operator sequences. The allosteric properties of the repressor can be tuned to improve transgene regulation. It allosterically induces gene expression by binding an orally active, small molecule isopropyl β-D-thiogalactopyranoside (IPTG) that is non-toxic to mammalian cells at inducing concentrations. Further the compositions described herein employ autogenous regulation. In this system, the lac repressor regulates its own transcription and the transgene is co-regulated. A basal amount of leakiness is required to maintain the repressed state of the switch, but this can be minimized by inclusion of multiple operator DNA sequences and high affinity lac repressor/operator pairs. This system in a viral vector has many features of an ideal gene therapy switch including that co-expression of the lac repressor and the transgene reduces the overall size of the cassette allowing larger transgenes to fit into an AAV capsid.

The results of the above examples demonstrate an autogenously regulated lac repressor can be used successfully for controlling transgene expression in a variety of cell types and in vivo in the retina and in the liver in mice after delivery of an AAV vector. The system showed low baseline expression in retinal tissue (<20% of constitutive expression) and approximately 5-fold induction of transgene. More importantly this regulation was reversible and capable of being turned on and off by giving an oral dose of a non-toxic effector (IPTG). The lac autogenous switch takes advantage of the inherent properties of autogeny: the response to effector is linear, fast and stable and minimal lac repressor concentrations are produced. The latter property would minimize potential immunogenic effects. The size of the switch allows for transgenes up to approximately 2400 base pairs to be packaged in AAV and the regulation is built-in; the level transgene product is regulated in every cell that is transduced by the AAV. Use of the lac repressor and operator has the advantage of providing malleability in designing future versions of lac autogenous switches. Different combinations of mammalian promoters, multiple lac operator sites, different lac operator sequences, and different mutants of the lac repressor with altered regulatory profiles can be used to engineer unique lac autogenous switches for specific diseases. Additional alterations could minimize leakiness of the system. This work illustrates that it is possible to translate our fundamental understanding of transcriptional regulation to create an inducible transgene regulatory system that can ultimately be used for AAV-mediated gene therapy.

Example 7—Additional Studies

An alternate approach for regulating gene expression, used by many biosynthetic operons, is autogeny[8,9]. Autogenous systems rely on a single regulated promoter that controls the expression of both the regulatory protein as well as the functional gene. The fundamental advantage of autogeny is that it eliminates the need to balance promoter productivity. In theory, autogenous expression of the regulator protein ensures a steady state level of a transcriptional regulator, regardless of the model system, cell type, copy number, or functional gene. Moreover, autogenous regulation has been shown to exhibit a linearized effector response (rheostatic)[10], have a quicker response upon effector dosage (sensitivity)[11], and is inherently less noisy than classically regulated gene circuits (stable)[12]. An additional practical advantage of an autogenously regulated system for gene replacement therapy is that using a single promoter significantly increases the effective cargo capacity of the viral delivery vector. For some vectors, such as AAV, the size of the vector poses a real physical limitation. The utility of autogeny has been recently demonstrated using a tetracycline regulated promoter[13], however, there have not been any direct comparisons of autogenously and classically regulated expression systems. Here we compare classical and autogenous regulation in a variety of model systems and explore the utility of autogenous regulation for gene therapy.

To evaluate the regulatory properties of an autogenously regulated expression system, we first compared the induction profiles of constitutively and autogenously expressed reporter protein in bacteria, with both systems utilizing the lacI repressor protein of the lac operon as the transcriptional regulator. The following methods and materials were employed:

Bacterial Strains and Media: The strain EPB229 (*E. coli* F-λ-ilvG-rfb-50 rph-1 Δ(lacI-lacA)::frt) was used for prokaryotic YFP regulation assays. This strain was made by the laboratory of Dr. Mark Goulian and derived from MG1655 (*E. coli* F-λ-ilvG-rfb-50 rph-1). This strain is the "wild-type" K-12 strain and has a total deletion of the lac operon allowing for a clean background within which to study our lac genetic regulatory systems. Liquid media for YFP regulation assays cells used LB media supplemented with appropriate concentrations of antibiotics and the inducer isopropyl thiogalactoside (IPTG).

Figure 9A:
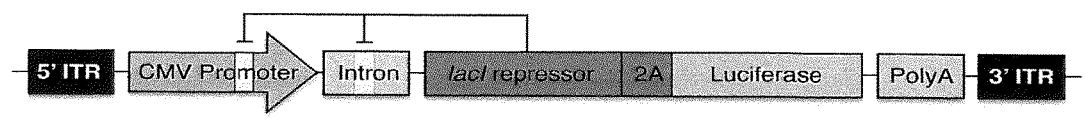
FIG. 9A is a map of the autogenously regulated expression system (ARES) within an AAV production vector (AAV8.ARES.Luciferase). A CMV promoter controls the expression of both the lacI repressor and Luciferase, linked via a 2A peptide cleavage sequence. Lac operator sites are indicated by orange boxes. Intronic, polyadenylation, and AAV ITR sequences are indicated. The autogenous regulatory system is functional in mouse retina in vivo.

Plasmid Construction: The prokaryotic constitutive lac repressor and YFP reporter plasmids were made as previously described[23]. Prokaryotic autogenously regulated reporter plasmid was made with the O1 operator sequence (5'-AA TT GTG AGC GAT AAC AA TT-3' SEQ ID NO: 6) followed by YFP, a 15 base pair spacer (5'-AAT TCA GGG TGG TGA-3' SEQ ID NO: 10) followed by the lac repressor with a C-terminal mCherry tag that was added to the gene after an 11 bp linker to create the Lac-mCherry fusion protein. The classical eukaryotic gene regulatory plasmid was constructed using the commercially available pBI-CMV1 plasmid (Clontech, Mountain View, Calif.) by subcloning a eukaryotic codon-optimized lac repressor gene linked at it's 3' end to an in-frame mCherry gene followed by a nuclear localization sequence (NLS) into the MCS immediately following the $P_{minCMV2}$ promoter. The gene encoding YFP was subcloned into the MCS immediately following the P$_{minCMV1}$ promoter, which we had modified by inserting the high affinity symmetric lac operator sequence[16] between the TATA box and the transcription start site. The autogenously regulated eukaryotic gene regulatory plasmid was constructed using the same pBI-CMV1 plasmid. The modified (as above) inducible P$_{minCMV1}$ promoter was used to drive expression of a transcript coding for both the Eukaryotic codon-optimized lac repressor linked to mCherry and an NLS (as above) in addition to the YFP reporter, with the two genes linked via a 2A peptide cleavage sequence[17]. To generate the eukaryotic ARES system expressing luciferase, the entire construct as depicted in FIG. 9A was synthesized by DNA2.0 and subcloned via restriction enzyme digestion and ligation into a previously described AAV production plasmid[19].

Prokaryotic YFP and mCherry E. coli regulation assay: We transformed the autogenously regulated reporter plasmid into EPB229 cells (F-Δ(lacI-lacA)::frt). These cells were derived from the MG1655 "wild type" line. Colonies were picked in triplicate into LB media with AMP and CAM and grown overnight at 37° C. with shaking. 50 µL of the overnight culture was used to inoculate 0.5 mL fresh LB media supplemented with varying amounts of IPTG. We measured optical density at 600 nm (OD600), in addition to YFP and mCherry fluorescence for all wells after 24 hours of growth using a TECAN M1000 plate reader in 96 well optical bottom plates (Corning, Corning, N.Y.). All data points collected were normalized to OD600 to account for differences in culture density.

Eukaryotic Cell Culture, Transfection, Transduction, and Induction: HEK293T cells were grown in Dulbecco's modified Eagle's medium (DMEM) supplemented with 10% fetal bovine serum (FBS). All cells were grown in humidified 5% $CO_2$ incubators at 37° C. All transfections were carried out with Fugene 6 reagent following the manufacturer's protocol. Cells were infected with AAV8.ARES.Luciferase at a concentration of 1×10$^6$ vg/cell. Cell media was supplemented with various concentrations of IPTG and cells were harvested 48 hours post-transduction/transfection and processed for luminescence/fluorescence analysis.

Mammalian cell luminescence and fluorescence assays: For luminescence assays, cells were washed with DPBS, lysed with Reporter Lysis Buffer (Promega, Madison, Wis.), and 10 µL of whole cell lysate was added to 80 µL of luciferase assay buffer (Promega, Madison, Wis.) containing luciferin within a well of a 96 well optical bottom plate (Corning, Corning, N.Y.). Plates were immediately loaded into a Tecan M1000 instrument and luciferase signal from each well was quantified. For fluorescence assays, cells were washed with DPBS and dislodged from the culture vessel by vigorous pipetting. Cells were resuspended in 50 µL of DPBS and added to individual wells of a 96 well optical bottom plate (Corning, Corning, N.Y.) and YFP fluorescence (excite: 510 nm emit: 535 nm) for all wells was determined using a XXX.

Mouse husbandry: Animals were housed in a 12 hour light:dark cycle facility. Animal care was in compliance with the Association for Research in Vision and Ophthalmology statement for the Use of Animals in Ophthalmic and Vision Research, and all procedures were approved performed with approval by the local Institutional Animal Care and Use Committee and were in compliance with federal guidelines.

Subretinal injections: Subretinal injections of AAV vectors were performed in 6 months old CD1 mice at a dose of 1×10$^{10}$ Vg. All surgeries were performed under inhaled anesthesia, and all efforts were made to minimize suffering. Contralateral eyes were used as uninjected controls. Injections were performed as described previously.[5] Administration of IPTG: Induction of luciferase expression was accomplished by oral gavage of 2 doses of IPTG twice a day over a 3 day period, with each dose consisting of 25 µl of 1M IPTG/10 g body weight.

Bioavailability of IPTG: Three CD-1 adult mice were gavaged with 25 µL of 1M IPTG per 10 g of body weight twice a day for 3 days. Animals were then sacrificed and major organs were harvested, mechanically homogenized, and steady state concentrations of IPTG in liver, kidney, skeletal muscle, and retina were determined using a beta-galacosidase assay[24]. The data (Figure not shown) showed that oral gavage provides sufficient IPTG concentrations in diverse tissues for ITRS induction in mice. IPTG concentrations were tracked in various mouse tissues after a single 3-day IPTG gavage induction cycle. Data points represent mean+/-SD, n=3. The $K_D$ of the interaction between lacI and inducer is ~4 µM[21] Furthermore, both the gavage concentration and steady state concentrations of IPTG are 50-fold and 500-fold less, respectively, than concentrations where IPTG is found to be toxic to cells.[15,22]

In vivo animal imaging: All mice were imaged before each cycle of IPTG gavage, immediately after each cycle of IPTG gavage, and again after 5-8 days of IPTG abstinence. The D-luciferin substrate (Goldbio, St Louis, Mo.) was injected intraperitoneally, at a dose of 15 µg/g of body weight. Animals were then anesthetized using isofluorane and imaging began 10 min after administration of D-luciferin. The mice were then placed in a light-tight chamber, and images were generated using a cryogenically cooled charge-coupling device camera IVIS 100 (Xenogen, Alameda, Calif.). Grey scale surface images of mice were collected, and the in vivo bioluminescence was represented as a pseudocolor images. The visual output represents the number of photons emitted/second/cm$^2$ as a false color image, where the maximum is red and the minimum is dark blue.

Tissue fixation, cryosectioning and histology: At the end of final IPTG administration, animals were imaged and sacrificed. Eyes were collected and fixed in 4% paraformaldehyde. Tissues were then cryoprotected and embedded in optimal cutting temperature media (Fisher Scientific Co., Pittsburgh, Pa., USA) and frozen. Cryosections were made using a Leica CM1850 cryostat (Leica Microsystems, Wetzlar, Germany). Sections were then stained with hematoxylin and eosin (H&E).

Mouse Retinal Data Analysis: Custom image analysis software was written in Matlab (Mathworks) and the files can be found on the Matlab File Exchange File ID: #48972. All analyses were performed on 5-second exposure raw luciferase images. Background was measured from an image of an un-injected, negative control left eye and the mean and standard deviation was recorded. A background threshold was defined as background mean+6 standard deviations; pixels higher than this are considered to be true luciferase signal from the AAV8.ITRS.luciferase vector. To isolate a single mouse eye, a region of interest is drawn around the entire mouse head and all pixels above the threshold are recorded. Each pixel intensity has the background mean subtracted and then is summed to integrate over the entire eye. Integrated values were used for statistics and are reported in the text and figures.

Statistics: Statistical analysis of fold changes in bacterial experiments, eukaryotic tissue culture experiments and mouse experiments were carried out using a Student's T-test using Gnumeric (gnumeric.org).

Figure 8A:
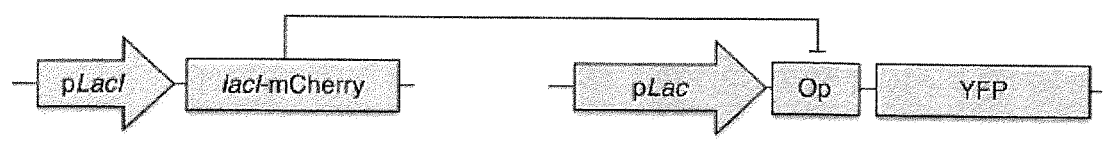
FIG. 8A is a schematic diagram of a bacterial classically regulated expression system (CRES). Promoters, regulator genes, reporter genes, and operator sequence are indicated.
Figure 8B:
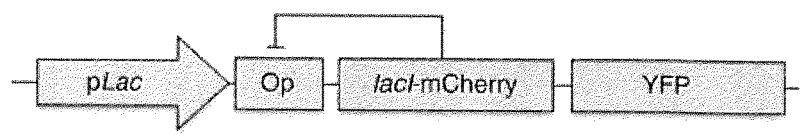
FIG. 8B is a schematic of an autogenously regulated expression system (ARES). Promoters, regulator genes, reporter genes, and operator sequence are indicated.

The results are described in summary and with reference to FIGS. 8A through 9F, the classically regulated expression system (CRES) was constructed using a weak constitutive bacterial promoter (pLacI) to drive the expression of the lacI repressor protein fused to mCherry. This repressor regulates a stronger inducible promoter (pLac) expressing yellow fluorescent protein (YFP) (FIG. 8A). The autogenously regulated expression system (ARES) relied on the same pLac inducible promoter to drive expression of a polycistronic message containing both YFP and the lacI protein fused to mCherry (FIG. 8B). Induction profiles were measured as a function of inducer (isopropyl thiogalactoside, IPTG), and both regulatory systems demonstrated inducible YFP expression, as expected, producing low levels of YFP in the absence of inducer and showing nearly full induction at low millimolar IPTG concentrations (FIG. 8C). In ARES, mCherry fluorescence, indicative of levels of mCherry-tagged lacI repressor protein, was also found to be significantly inducible with increasing doses of IPTG, confirming that in autogenously regulated systems repressor protein levels are appropriately titrated to the given conditions (FIG. 8D). We did also notice a very small increase in mCherry fluorescence in CRES with increasing inducer concentrations, and suspect that this is simply due to an overlap of the emission spectra of YFP and mCherry rather than a true increase in levels of LacI-mCherry fusion protein.

Figure 8C:
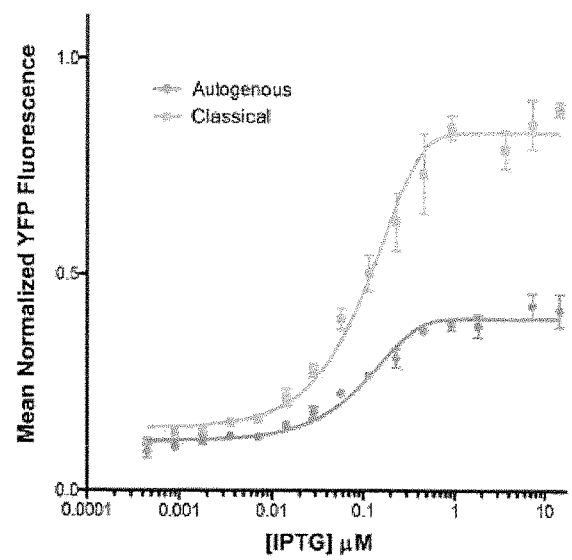
FIG. 8C shows the mean normalized YFP fluorescence as a function of IPTG concentration for both the CRES of FIG. 8A and ARES of FIG. 8B in *E. coli*. Data were normalized to an *E. coli* tranformant expressing YFP under the control of a constitutive promoter. Data points represent mean+/−SEM, n=5.
Figure 8D:
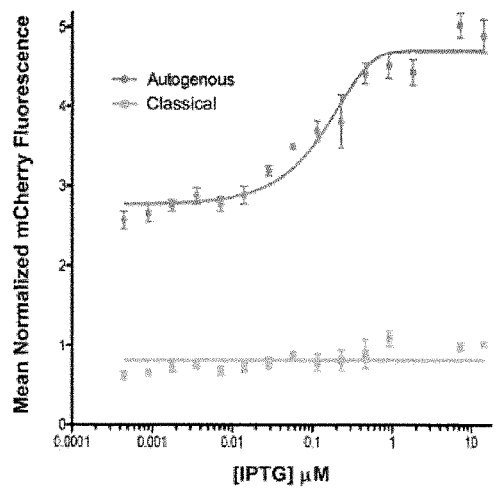
FIG. 8D shows the mean normalized mCherry fluorescence of the lacI-mCherry fusion as a function of IPTG concentration for both CRES of FIG. 8A and ARES of FIG. 8B in *E. coli*. Data were normalized to an *E. coli* tranformant expressing lacI-mCherry under the control of a constitutive promoter. Data points represent mean+/−SEM, n=5.

One significant advantage of the ARES system was immediately apparent in our data: whereas ARES automatically titrates repressor protein levels to maintain appropriate levels, CRES cannot fine-tune its own expression for different inducer levels or model systems. This was apparent when looking both at repressor levels and at the leakiness of our systems. Levels of repressor in CRES, as indicated by mCherry fluorescence, were too low (nearly 5-fold lower than in ARES at the maximally induced state (FIG. 8D)) to maintain tight control of YFP expression, and thus CRES was characterized by significant leakiness of YFP expression when uninduced (FIG. 8C). On the other hand, the lower levels of repressor protein also afforded CRES a greater induction profile than ARES, with YFP levels nearly double those of the autogenous system in the maximally induced state (FIG. 8C). Thus, ARES was found to be less leaky and more adaptable, but with a smaller fold change in YFP expression than CRES, as would be expected[14]. Given the kinetic advantages of autogeny and the appropriate thermodynamic properties, we next wanted to establish how ARES would function in eukaryotic cells.

Figure 8E:
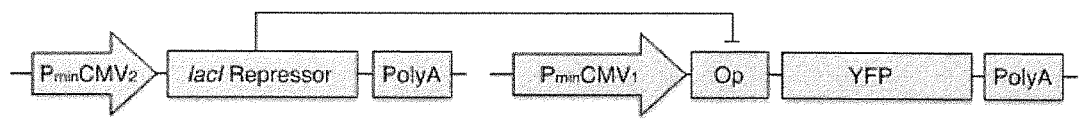
FIG. 8E is a schematic diagram of another eukaryotic classically regulated expression system (CRES). Promoters, regulator genes, reporter genes, polyadenylation sites, 2A cleavage signal, and operator sequence are indicated.
Figure 8F:
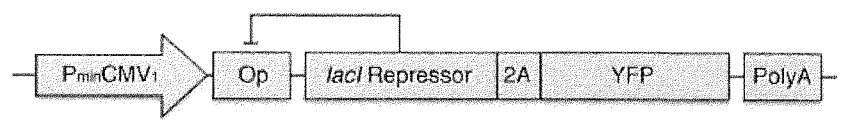
FIG. 8F is a schematic diagram of another autogenously regulated expression system (ARES). Promoters, regulator genes, reporter genes, polyadenylation sites, 2A cleavage signal, and operator sequence are indicated.
Figure 8G:
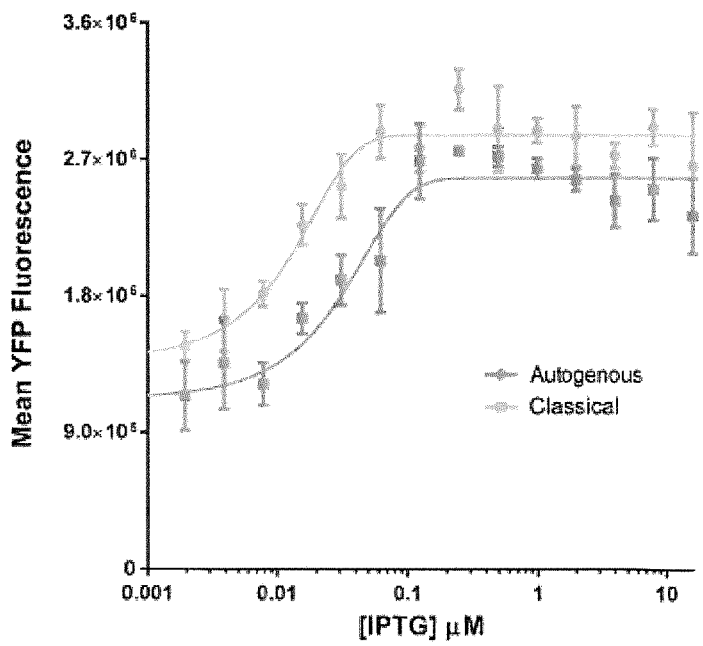
FIG. 8G shows the mean YFP fluorescence as a function of IPTG concentration for both the CRES of FIG. 8E and ARES of FIG. 8F in transfected 293T cells. Data points represent mean+/−SEM, n=3.
Figure 8H:
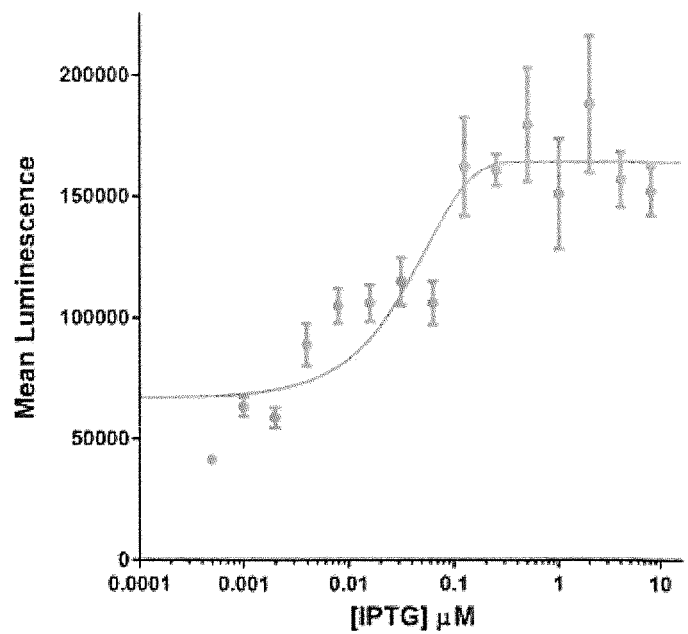
FIG. 8H shows the mean luminescence as a function of IPTG concentration for the ARES encoding luciferase as a reporter in AAV-transduced 293T cells. Data points represent mean+/−SEM, n=3.

To establish how these expression systems behave in eukaryotic cells, we created eukaryotic expression systems that are classically and autogenously regulated and compared their regulatory properties in transfected HEK293T cells. Analogous to the prokaryotic system, a constitutively regulated expression system (CRES) was produced using a bi-directional expression system (Clontech, Mountain View, Calif.) where a weak minimal cytomegalovirus promoter ($P_{minCMV2}$) drives expression of a eukaryotic codon-optimized lac repressor[15] and a second, stronger minimal cytomegalovirus promoter ($P_{minCMV1}$), modified by inserting the high affinity symmetric lac operator sequence[16] between the TATA box and the transcription start site, drives inducible expression of the YFP reporter gene (FIG. 8E). An autogenously regulated expression system (ARES) was built using the same modified inducible CMV promoter ($P_{minCMV1}$) to drive expression of a transcript that codes for both the lac repressor and the YFP reporter, linked via a 2A peptide cleavage sequence[17] (FIG. 8F). These expression systems were transiently transfected into HEK293T cells and YFP fluorescence was measured as a function of the inducer (FIG. 8G). Upon induction, gene expression increased roughly 2.5-fold ($p<0.001$) in both systems, confirming that the lac repressor is functional in eukaryotic systems. The induction profiles were similar to what we had observed in prokaryotes, with ARES exhibiting lower levels of expression when maximally induced and slightly lower fold change than what was observed for CRES, but again with significantly lower leakiness in YFP expression in the uninduced state (FIG. 9G).

The autogenously regulated system was further evaluated by replacing YFP with luciferase as a reporter and by the addition of an ancillary operator sequence within the intron, a modification that previous studies have reported to result in tighter transgene regulation[18]. This new construct was sub-cloned into an AAV production vecto[19], and packaging into AAV8 virions (AAV8.ARES.luciferase) (FIG. 9A). HEK293T cells were transduced with AAV8.ARES.luciferase and induction profiles were measured as a function of inducer. Again we observed a robust dose-response (FIG. 8H), this time with a nearly 4-fold induction of luciferase activity between the off and maximally induced states ($p<0.05$), confirming that the ARES, when delivered virally, can also successfully regulate eukaryotic gene expression.

Figure 9B:
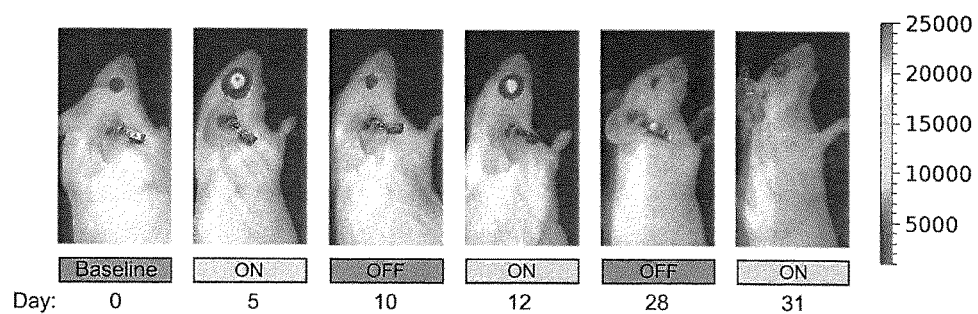
FIG. 9B shows live imaging of luciferase activity over a 33-day period in a representative animal subretinally injected with AAV8.ARES.luciferase in the right eye.

To examine the utility of this ARES in vivo, eight, age-matched, adult CD-1 mice received unilateral subretinal injections with AAV8.ARES.luciferase. These mice were then subjected to cycles of IPTG gavage for three days at doses that we had previously found to result in sufficient tissue concentrations of inducer for ARES induction (figure not shown), followed by at least 5 days without IPTG gavage. Luciferase levels were determined using an IVIS Series Pre-clinical in vivo Imaging System immediately before and immediately after each cycle of IPTG administration over a total of three induction cycles during a period of 33 days (FIG. 9B).

Figure 9C:
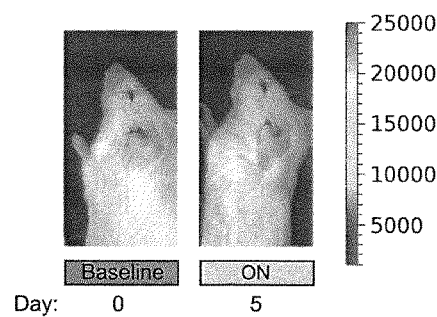
FIG. 9C shows live imaging of luciferase activity in the left, un-injected eye of the same animal as in FIG. 9A.
Figure 9D:
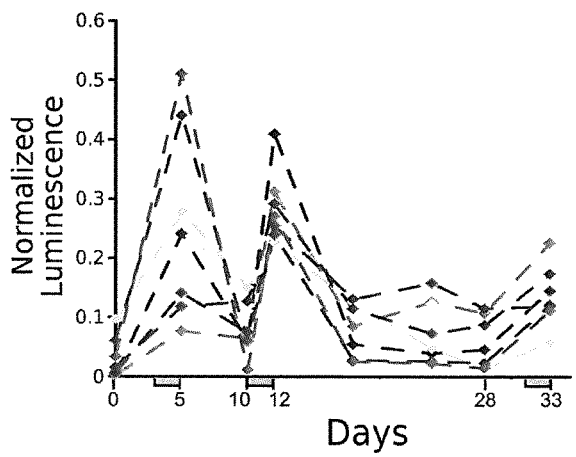
FIG. 9D shows the normalized integrated luminescence of the right, injected eye for each animal on each imaging day. Bars on the X axis represent days of IPTG gavage.
Figure 9E:
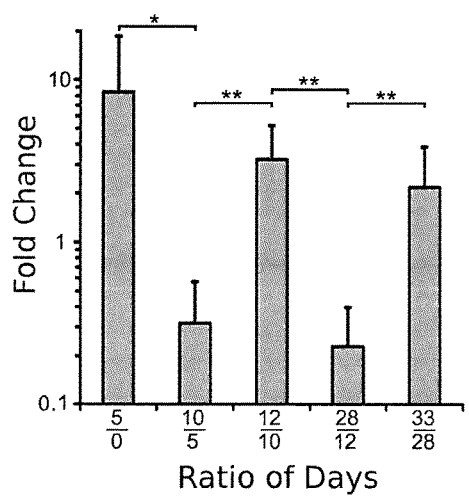
FIG. 9E shows the fold change in integrated right eye luminescence on each imaging day. Fold change >1 indicates induction of luciferase expression while fold change <1 indicates repression of luciferase expression. *p<0.05, **p<0.01, n=8.
Figure 9F:
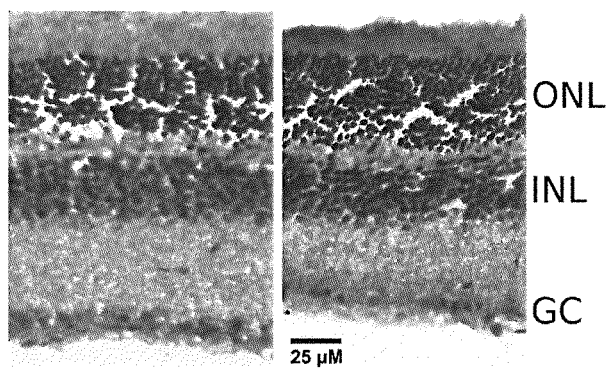
FIG. 9F shows histological sections of injected mouse retina from two representative animals stained with hematoxylin and eosin. (ONL, outer nuclear layer, INL, inner nuclear layer. GC, ganglion cells layer).

Injected retinas displayed substantial luminescence localized to the injected eye, with the intensity of the signal being significantly increased following IPTG dosage (FIG. 9B, 9D); the un-injected eyes never showed luminescence (FIG. 9C). For each induction cycle, we observed a significant increase in integrated retinal luciferase signal over baseline luminescence when induced ($p<0.01$, $p<0.001$, and $p<0.001$, respectively) and a return to baseline upon withdrawal of IPTG ($p<0.05$ and $p<0.001$, respectively) (FIG. 9D). The first induction was the most robust, with an average 8-fold increase in signal, whereas the second and third inductions showed a 2-3-fold increase in signal, similar to results we had observed in cultured cells (FIG. 9E). Histological evaluation of retinal sections from both injected and un-injected eyes did not reveal any abnormalities or immune infiltrates, suggesting that the autogenous regulation is effective and well tolerated in the murine retina (FIG. 9F).

Here we have established that an autogenously regulated expression system exhibits similar steady state induction profiles compared to the classical operon model system. Although both regulatory systems successfully control transgene expression in a variety of cell types both in vitro and in vivo, the autogenous system may be more useful for gene therapy. While a two-promoter system has the desired effect of being able to regulate the transgene and the repressor independently, if the promoters are not properly balanced the switch is ineffective; too much repressor prevents transgene production while transgene production is effectively constitutive if there is too little repressor. The simple architecture of the autogenous system ensures a proper balance of the regulator to minimize leakiness and maximize dynamic range regardless of the system being tested and without the need to empirically balance promoters. On a more practical note, the compact nature of the autogenous system lends itself more readily to packaging within viral vectors for gene therapeutic applications.

A variety of inducible systems that rely on small bioactive effector molecules have been developed for regulating transgene expression. A lac repressor-based system, however, such as the one described here, has a variety of features that are potentially superior for regulating transgene production. The binding affinity of this repressor is modulated with the addition of a metabolite that is non-toxic with no known off-target effects. The allosteric properties of the lac repressor can be tuned to both decrease basal expression and to increase the induction ratio[20]. Such allosteric modifications, along with optimization of promoter/terminator machinery and operator DNA number and placement could improve the performance of the ARES described here while still maintaining its compact size. Finally, lac repressor binds cooperatively to appropriately spaced operators, which in bacteria decrease the leakiness and greatly improve its regulatory properties—this strategy could similarly be applied to the ARES we describe here to affect improved dynamic range and decreased leakiness.

Building a regulatory circuit specifically for gene therapy requires optimizing several variables: The regulatory system needs have a large dynamic range, respond quickly to changes in effector concentration, and must be small, providing sufficient space for the therapeutic gene, given the limited capacity of a viral capsid. An autogenously regulated system satisfies these objectives and, as we have shown here, is comparable in kinetics and dynamic range to traditional constitutively expressed transgene regulatory systems without the need for promoter balancing or empiric tuning for different applications. These data establish the proof-of-concept of using autogeny and the lac repressor to control transgenes in AAV-mediated gene therapeutic applications.

The autogenous transgene regulatory system (ARES) based on the bacterial lac repressor is comparable to constitutive transgene regulation in terms of kinetics and induction profiles, but is superior in that it titrates the level of repressor to maintain appropriate levels under all conditions, and is small enough to easily fit within the limited packaging constraints of viral vectors such as adeno-associated virus (AAV). Transgene expression increased several fold after induction.

Example 8—Gene Expression Employing Two Levels of Regulation

To optimize and enhance the expression of the gene inducible ARES system described above, a second layer of regulation was introduced to create a robust transgene regulatory system that layers two different regulatory systems: one to control the synthesis of the mRNA and the other to control the degradation of mRNA.

The first level of regulation is the synthesis of mRNA, which is controlled by transcriptional regulators. Repressors decrease the probability a promoter is occupied while activators increase the probability of promoter occupancy. In general, repressors attenuate transcription by interfering with polymerase binding. A variety of mechanisms have been observed; the simplest is steric hindrance. In this situation a repressor binds to a site located within, or close to, the promoter and competes with polymerase binding. Binding of the repressor to an operator downstream of the promoter, physically blocks polymerase from binding to the promoter. The repressor is allosterically regulated such that in the absence of effector molecules (e.g., first inducing molecule), the repressor binds to its operator and decreases the probability that polymerase binding to the promoter. In the presence of the effector, the repressor no longer can bind to its operator, allowing polymerase to bind to the promoter. A paradigm of this form of regulation is the lactose operon.

The second level of regulation is controlling the degradation of mRNA. The rate of the messenger RNA is degraded, $\gamma_m$, will determine the steady state level of mRNA and therefore the production of the transgene. An inducible hammerhead ribozymes was created that that cleaves itself in the absence of effector molecule. When the ribozyme is placed immediately upstream of a polyA tail, the degradation of the mRNA is inducible. Combining two different inducible systems, one that regulates the synthesis of mRNA with a second that regulates the degradation of the mRNA, creates a novel transgene regulatory system. Layering two regulatory systems will potentially be less leaky than existing systems and has a better dynamic range.

Based on this theoretical underpinning, this was accomplished by inserting an inducible hammerhead ribozyme upstream of the polyA tail. The first level of regulation (which involves regulating the promoter) is provided by the ARES systems and is accomplished by inserting a symmetric lac operator sequence between the TATA box and the transcription start site. The regulation of this system is controlled in a first example by IPTG. The second layer of regulation is accomplished by inserting an inducible hammerhead ribozyme upstream of the polyA tail. In one example, this second regulation can be controlled by tetracycline. The first and second inducing molecules can be altered based on the selection of components forming the construct. In a cell culture system, when this dual regulatory system was tested there was more than one log unit change in transgene expression. This dual regulatory system maintains the ARES system (compact, inducible, functional in eukaryotic cells) but now enhances the level of induction significantly. Further, additional manipulations (in progress) will be used to fine-tune the expression and allow incorporation of additional enhancer molecules.

Figure 10:
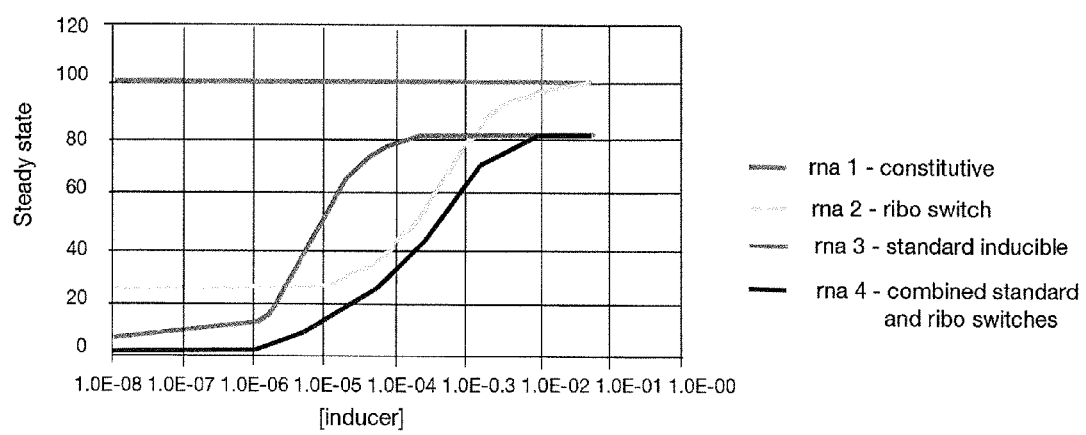
FIG. 10 is a graph showing the theoretical steady state RNA production vs. inducer for constitutive expression of a transgene (rna1—horizontal line at steady state of 100); a ribozyme switch with 4 fold reduction (rna2—line starting at about 24 and ending at about 100); a standard inducible switch (rna3-line starting at about 8 and ending at about 80) and for the dual gene switch described herein (rna4—dark black line). The Y axis represents luciferase activity (relative light units/mg protein), which was standardized to total protein. The constitutive expression sample was assigned a relative value of 100% and all others adjusted accordingly. The X axis represents relative molar concentration of inducers (IPTG and/or Tet, depending on construct tested).

Another embodiment of a self-regulatory, inducible gene expression construct employs layering two regulatory systems into a single construct to control both the synthesis and the degradation of mRNA of a transgene. FIG. 10 illustrates that the first level of regulation (rna3) and the second level of regulation (rna 2) are both leaky and have a modest dynamic range. When the two regulatory systems are layered (rna4), the basal level of expression is very low so it is less leaky and the dynamic range or fold-change is much greater.

Figure 11:
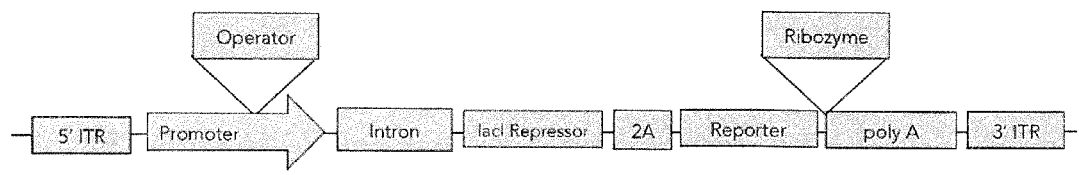
FIG. 11 is a schematic diagram of a regulatory system that contains two levels of regulation, e.g., inducible plus ribozyme switch.
Figure 12:
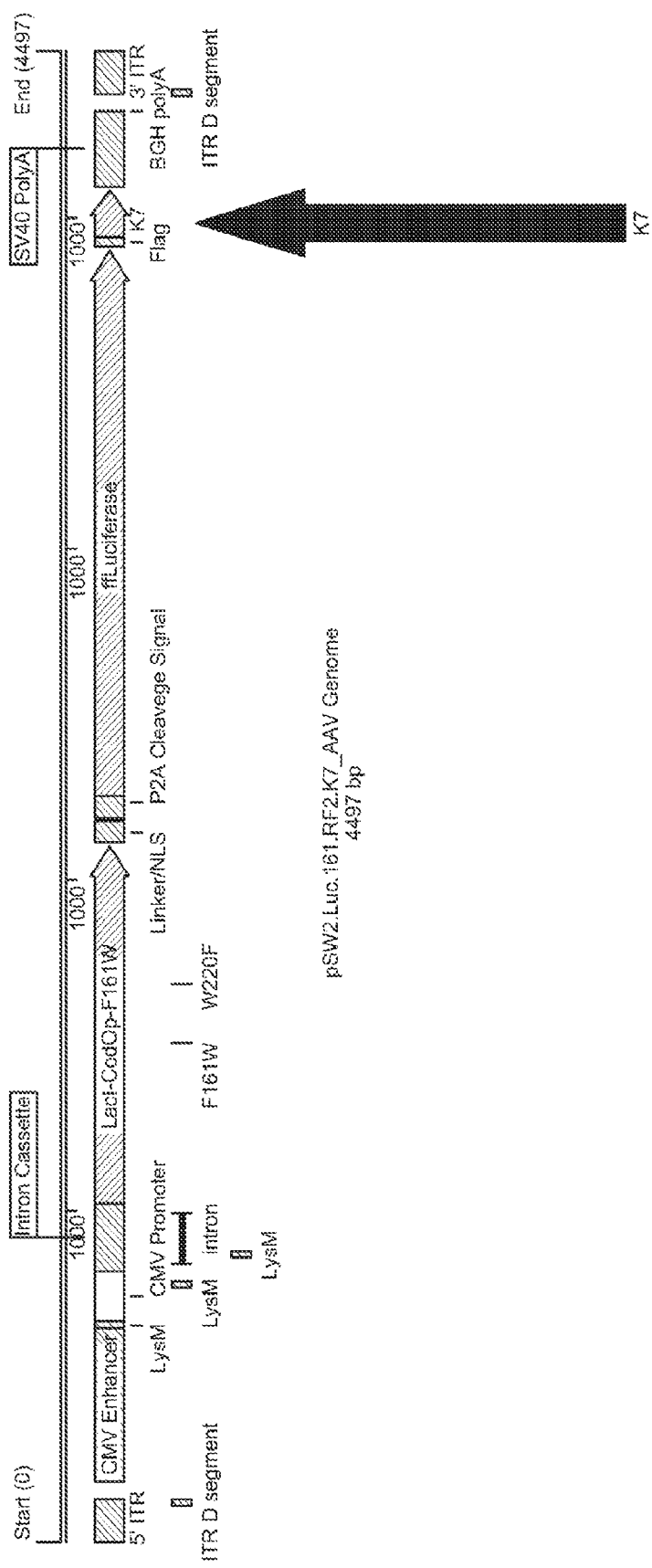
FIG. 12 is a schematic diagram of the regulatory construct pSW2.Luc.161.RF2.K7 flanked by a 5' AAV ITR and a 3' AAV ITR, that contains two levels of regulation, e.g., inducible with a CMV enhance/promoter, codon-optimized lacI operator and repressor, P2A cleavage sequence, luciferase transgene and the tetracycline dependent ribozyme sequence, K7.

To evaluate the benefit of layering different these regulatory mechanism on transgene production we built an autogenously regulated expression system (FIGS. 11 and 12). The system is driven by a minimal cytomegalovirus promoter (PminCMV1) to express a eukaryotic codon-optimized lac repressor and a luciferase reporter, linked via a 2A peptide cleavage sequence. The first level of regulation involved regulating the CMV promoter, which was accomplished by inserting a symmetric lac operator sequence between the TATA box and the transcription start site.

The second layer of regulation was to control the degradation of the mRNA transcript. It relies on incorporation of an inducible hammerhead ribozyme to control the degradation of the mRNA transcript. An inducible tetracycline dependent hammerhead ribozyme K7 (see also Bielstein[53])

was inserted upstream of the polyA tail. See, the schematic map of FIG. 12 and the sequence of an exemplary construct pSW2.Luc.161.RF2.K7 in FIG. 14 (SEQ ID NO: 15). The elements of pSW2.Luc.161.RF2.K7 and the first and last nucleic acid positions of each element in SEQ ID NO: 15 are set out in the following Table I:

TABLE I

Elements of Dual Switch Construct of SEQ ID NO: 15

| Element | First nucleotide | Last nucleotide |
|---|---|---|
| 5' ITR | 1 | 130 |
| CMV Enhancer | 181 | 647 |
| Optimized Lac I operator (referred to as Lsym or LysM) | 648 | 667 |
| CMV Promoter | 670 | 819 |
| Optimized Lac I operator (referred to as Lsym or LysM) | 774 | 793 |
| Intron | 843 | 995 |
| Optimized Lac I operator (referred to as Lsym or LysM) | 866 | 885 |
| Lac I repressor | 1027 | 2113 |
| P2A cleavage sequence | 2188 | 2253 |
| Luciferase transgene | 2260 | 3909 |
| K7 Ribozyme-Aptamer (Aptazyme) | 3943 | 4090 |
| SV40 PolyA | 4097 | 4318 |
| 3' AAV ITR | 4368 | 4497 |

In pSW2.Luc.161.RF2.K7, the first regulatory component (i.e., the promoter-operators-LacI repressor) is inducible with a galactoside (IPTG) and second regulatory component, provided by the ribozyme-aptamer placed upstream of the polyA sequence is inducible by tetracycline.

The AAV ITR-flanked construct pSW2.Luc.161.RF2.K7 was transfected into HEK293T cells as follows. HEK293T cells were grown in Dulbecco's modified Eagle's medium (DMEM) supplemented with 10% fetal bovine serum (FBS). Cells were grown in humidified 5% $CO_2$ incubators at 37° C. All transfections were carried out with Fugene 6 reagent following the manufacturer's protocol. For induction, cell media was supplemented with either 2.5 mM IPTG or 250 uM Tetracycline (or both 2.5 mM IPTG and 250 uM Tetracycline) and cells were harvested 48 hours post-transfection and processed for luminescence analysis.

For luminescence assays, cells were washed with DPBS, lysed with Reporter Lysis Buffer (Promega, Madison, Wis.), and 10 μL of whole cell lysate was added to 80 μL of luciferase assay buffer (Promega, Madison, Wis.) containing luciferin within a well of a 96 well optical bottom plate (Corning, Corning, N.Y.). Plates were immediately loaded into a Tecan M1000 instrument and luciferase signal from each well was quantified.

Figure 13A:
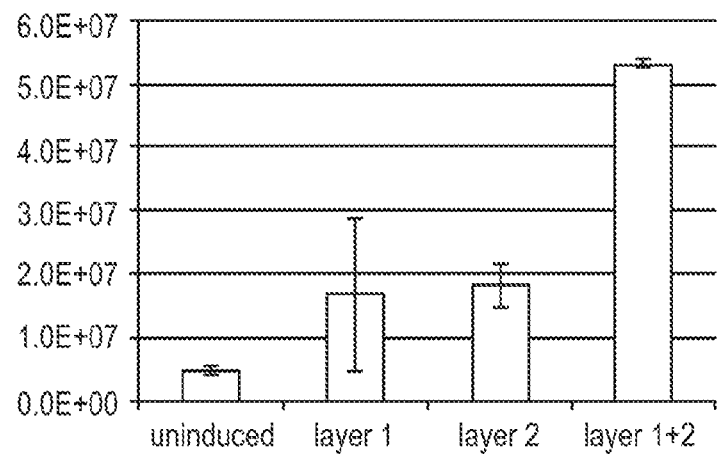
FIG. 13A is a bar graph showing luciferase levels (ranging from 0 to 6×10$^7$) for the regulatory system when uninduced and induced with the inducible switch only (layer 1), the ribozyme switch only (layer 2) and with the dual switch (layer 1+2).
Figure 13B:
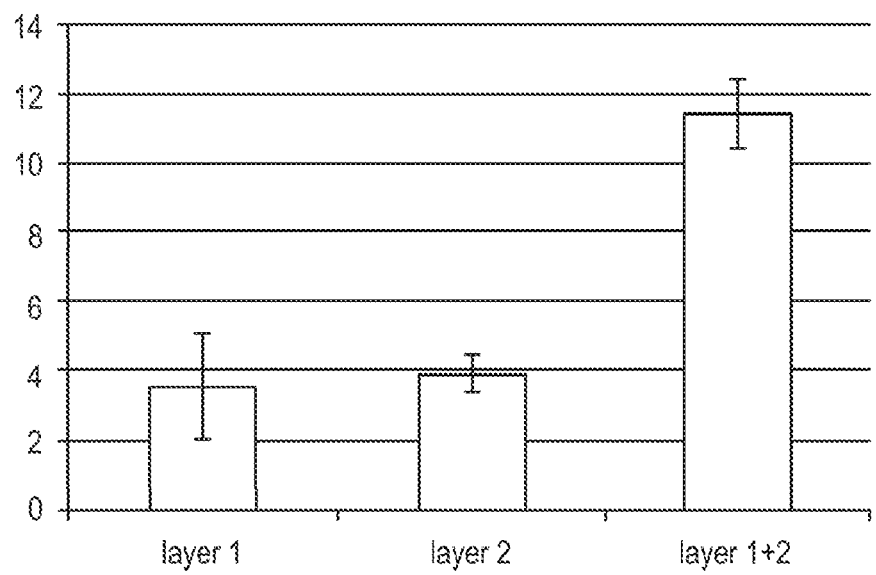
FIG. 13B is a bar graph showing the fold change in transgene expression for individual switches: inducible only, ribozyme only and combined (symbols as in FIG. 12A).

We observed nearly 4-fold induction of luciferase activity between the off and maximally induced states using either IPTG or tetracycline. When both effectors molecules were added to the media, we observed nearly a 12-fold change in luciferase levels (FIGS. 13A and 13B). The dynamic range or fold-change is much greater. This dual regulatory gene expression system provides a significantly wider "tuning spectrum" and lower baseline levels of transgene expression than the ARES system. This dual regulatory system maintains the originally described ARES system (compact, inducible, functional in eukaryotic cells) but now enhances the level of induction significantly.

Further, additional manipulations, including the incorporation of additional enhancer molecules, the use of additional ribozymes (or other aptamers) and inducers, and the placement of the ribozymes in other positions in the construct are anticipated to produce additional useful examples of the dual switches.

Example 9—In Vivo Studies

Subretinal injections of AAV vectors containing the construct of FIG. 14 are performed in 6 months old CD1 mice at a dose of $1 \times 10^{10}$ Vg. All surgeries are performed under inhaled anesthesia, and all efforts are made to minimize suffering. Contralateral eyes are used as uninjected controls. Injections are performed as described previously.[5] Administration of IPTG: Induction of luciferase expression is accomplished by oral gavage of 2 doses of IPTG twice a day over a 3 day period, with each dose consisting of 25 μl of 1M IPTG/10 g body weight. Administration of tetracycline: Induction of mRNA degradation is accomplished by oral administration gavage of sufficient doses of tetracycline over the same 3 day period.

Animals are then sacrificed and major organs are harvested, mechanically homogenized, and steady state concentrations of IPTG in liver, kidney, skeletal muscle, and retina are determined using a beta-galacosidase assay[24]. Oral gavage provides sufficient IPTG concentrations in diverse tissues for ITRS induction in mice. IPTG concentrations are tracked in various mouse tissues after a single 3-day IPTG gavage induction cycle. Furthermore, both the gavage concentration and steady state concentrations of IPTG and tetracycline are less than concentrations where IPTG or tetracycline is found to be toxic to cells.

In vivo animal imaging: All mice are imaged before each cycle of IPTG gavage, immediately after each cycle of gavage, and again after 5-8 days of first and second inducing molecule abstinence. The D-luciferin substrate (Goldbio, St Louis, Mo.) is injected intraperitoneally, at a dose of 15 μg/g of body weight. Animals are then anesthetized using isofluorane and imaging began 10 min after administration of D-luciferin. The mice are then placed in a light-tight chamber, and images are generated using a cryogenically cooled charge-coupling device camera IVIS 100 (Xenogen, Alameda, Calif.). Grey scale surface images of mice are collected, and the in vivo bioluminescence is represented as a pseudocolor images. The visual output represents the number of photons emitted/second/$cm^2$ as a false color image, where the maximum is red and the minimum is dark blue. Tissue fixation, cryosectioning and histology: At the end of final first and second inducing molecule administration, animals are imaged and sacrificed. Eyes are collected and fixed in 4% paraformaldehyde. Tissues are then cryoprotected and embedded in optimal cutting temperature media (Fisher Scientific Co., Pittsburgh, Pa., USA) and frozen. Cryosections are made using a Leica CM1850 cryostat (Leica Microsystems, Wetzlar, Germany). Sections are then stained with hematoxylin and eosin (H&E).

Mouse Retinal Data Analysis: Custom image analysis software is written in Matlab (Mathworks). All analyses are performed on 5-second exposure raw luciferase images. Background is measured from an image of an un-injected, negative control left eye and the mean and standard deviation is recorded. A background threshold is defined as background mean+6 standard deviations; pixels higher than this are considered to be true luciferase signal from the vector. It is anticipated that results for this assay show equal effectiveness of transgene regulation but less leakiness and more dynamic control of transgene expression.

All publications cited in this specification, and the sequence listing, are incorporated herein by reference. While the invention has been described with reference to particular embodiments, it will be appreciated that modifications can be made without departing from the spirit of the invention. Such modifications are intended to fall within the scope of the appended claims.

TABLE (SEQUENCE LISTING FREE TEXT)

The following information is provided for sequences containing free text under numeric identifier <223>.

| SEQ ID NO: (containing free text) | Free text under <223> |
|---|---|
| 1 | Synthetic construct containing minimal CMVI promoter, optimized E. coli Lac 1 operator (Lsym), yellow fluorescent protein reporter gene separated by an IRES sequence from an E. coli lac repressor sequence, C-terminal tag |
| 2 | Synthetic construct containing minimal CMVI promoter having two Lsym sites, a green fluorescent protein reporter gene separated by a 2A cleavage sequence from the E. coli lac repressor sequence. |
| 10 | Synthetic construct spacer sequence |
| 11 | Synthetic construct spacer sequence |
| 12 | Synthetic construct linker sequence |
| 13 | Synthetic construct for codon optimized Lac sequence from E. coli |
| 14 | Synthetic construct for optimized CMV/IE promoter region including E coli Lsym operator |
| 15 | Synthetic construct containing CMV enhancer/promoter, E. coli lacI operon, P2A cleavage site; luciferase reporter, hammerhead ribozyme with tetracycline aptamer and poly A, flanked by AAV ITRs |

REFERENCES

1. Toniatti, C., et al. Gene therapy progress and prospects: transcription regulatory systems. *Gene Ther.* 11, 649-57 (2004).
2. Chtarto, A. et al. A next step in adeno-associated virus-mediated gene therapy for neurological diseases: regulation and targeting. *Br. J. Clin. Pharmacol.* 76, 217-32 (2013)
3. Ginn, S. L., et al, J. Gene therapy clinical trials worldwide to 2012—an update. *J. Gene Med.* 15, 65-77 (2013).
4. Maguire, A. et al. Safety and Efficacy of Gene Transfer for Leber's Congenital Amaurosis. *N. Engl. J. Med.* 358, 2240-2248 (2008).
5. Bennett, J., Chung, D. C. & Maguire, A. Gene delivery to the Retina: From mouse to man. Methods Enzymol. 507, 255-274 (2012).
6. Karlsson, M., et al. De novo design and construction of an inducible gene expression system in mammalian cells. Methods Enzymol. 497, 239-53 (Elsevier Inc., 2011).
7. Jacob, F. & Monod, J. Genetic regulatory mechanisms in the synthesis of proteins. *J. Mol. Biol.* 3, 318-356 (1961).
8. Goldberger, R. F. Autogenous regulation of gene expression. Science 183, 810-816 (1974).
9. Savageau, M. A. Comparison of classical and autogenous systems of regulation in inducible operons. Nature 252, 546-549 (1974).
10. Nevozhay, D., et al. Negative autoregulation linearizes the dose-response and suppresses the heterogeneity of gene expression. *Proc. Natl. Acad. Sci. U.S.A* 106, 5123-8 (2009).
11. Rosenfeld, N., et al. Negative Autoregulation Speeds the Response Times of Transcription Networks. *J. Mol. Biol.* 323, 785-793 (2002).
12. Becskei, A. & Serrano, L. Engineering stability in gene networks by autoregulation. *Nature* 405, 590-3 (2000).
13. Chen, Y. et al. RANGE: Gene Transfer of Reversibly Controlled Polycistronic Genes. Mol. Ther. Nucleic Acids 2, e85 (2013).
14. Daber, R. et al. One is not enough. *J. Mol. Biol.* 392, 1133-44 (2009).
15. Cronin, C. A., et al. The lac operator-repressor system is functional in the mouse. *Genes Dev.* 15, 1506-1517 (2001).
16. Sadler, J et al. A perfectly symmetric lac operator binds the lac repressor very tightly. Proc. Natl. Acad. Sci, USA, 80, 6785-6789 (1983).
17. Trichas G, et al 2008 Use of the viral 2A peptide for bicistronic expression in transgenic mice. BMC Biol 6: 40
18. Oehler, S. et al. 1990 The three operators of the lac operon cooperate in repression. EMBO J., 9, 973-979.
19. Vasireddy, V. et al AAV-Mediated Gene Therapy for Choroideremia: Preclinical Studies in Personalized Models. PLoS One 8, (2013).
20. Daber, R., Sochor, M. A. & Lewis, M. Thermodynamic analysis of mutant lac repressors. *J. Mol. Biol.* 409, 76-87 (2011).
21. Barkley, M. D. & Bourgeois, S. in The Operon (Miller, J. H. & Reznikoff, W. S.) 177-220 (Cold Spring Harbor Laboratory, 1980).
22. Figge, J., et al. 1988 Stringent regulation of stably integrated chloramphenicol acetyl transferase genes by *E. coli* lac repressor in monkey cells. *Cell* 52, 713-22.
23. Daber, R. & Lewis, M. A novel molecular switch. *J. Mol. Biol.* 391, 661-670 (2009).
24. Miller, J. H. Experiments in Molecular Genetics. (Cold Spring Harbor Laboratory, 1982).
25. Swint-Kruse, L. & Matthews, K. S. Allostery in the LacI/GalR family: variations on a theme. *Curr. Opin. Microbiol.* 12, 129-37 (2009).
26. Sharp, K. A. Allostery in the lac operon: population selection or induced dissociation? *Biophys. Chem.* 159, 66-72 (2011).
27. Hu, M. C. & Davidson, N. The inducible lac operator-repressor system is functional in mammalian cells. *Cell* 48, 555-66 (1987).
28. Hu M C, Davidson N (1991) Targeting the *Escherichia coli* lac repressor to the mammalian cell nucleus. Gene 99: 141-150
29. Scrable, H. & Stambrook, P. J. Activation of the lac Repressor in the Transgenic Mouse. *Genetics* 147, 297-304 (1997).
30. Cronin C A, et al. 2003 Tyrosinase expression during neuroblast divisions affects later pathfinding by retinal ganglion cells. J Neurosci 23: 11692-11697
31. Weiss R et al, 2003 Genetic Circuit Building Blocks for Cellular Computation, Communications, and Signal Processing", *Natural Computing* 2:47-84
32. Santoso, L et al, 2006 Proceedings of the 45$^{th}$ IEEE Conference on Decision and Control, "On the Modeling of a Bistable Genetic Switch"
33. U.S. Pat. No. 6,340,741
34. U.S. Pat. No. 6,004,941
35. Burcin M M et al, 1999 Adenovirus-mediated regulatable target gene expression in vivo. PNAS 96: 355-360
36. Danielian P S, et al. 1998 Modification of gene activity in mouse embryos in utero by a tamoxifen-inducible form of Cre recombinase. Curr Biol 8: 1323-1326
37. Dejneka N S, et al. 2001 Pharmacologically regulated gene expression in the retina following transduction with viral vectors. Gene Ther 8: 442-446

38. Dejneka, N. et al, 2003 Gene therapy and animal models for retinal disease. *Opthalmology* 37, 188-198.
39. Donnelly M L, et al 2001 Analysis of the aphthovirus 2A/2B polyprotein 'cleavage' mechanism indicates not a proteolytic reaction, but a novel translational effect: a putative ribosomal 'skip'. J Gen Virol 82: 1013-1025
40. Donnelly M L, et al, 1997 J. Gen. Virol., 78(Pt 1):13-21
41. Lewis M (2005) The lac repressor. C R Biol 328: 521-548
42. Bujard H (1992) Tight control of gene expression in mammalian cells by tetracycline-responsive promoters. Proc Natl Acad Sci USA 89
43. Liang F-Q, et al. 1999 Transplantation of transduced postmitotic human neuronal cell lines: A potential vehicle for therapetuic gene transfer into retina. Invest Ophthalmol Vis Sci 40: 5723
44. Liang F-Q, et al. 2000 Intraocular delivery of recombinant virus. In Methods in Molecular Medicine: Ocular Molecular Biology Protocols, Rakoczy P E (ed) pp 125-139. Totowa, N.J.: Humana Press Inc
45. Manfredsson F P, et al. 2012 Regulated protein expression for in vivo gene therapy for neurological disorders: progress, strategies, and issues. Neurobiol Dis 48: 212-221
46. Milk L, et al. 2010 Functional rules for lac repressor-operator associations and implications for protein-DNA interactions. Protein Sci 19: 1162-1172
47. No D, et al. 1996 Ecdysone-inducible gene expression in mammalian cells and transgenic mice. Proc Natl Acad Sci USA 93: 3346-3351
48. Sochor M A (2014) In vitro transcription accurately predicts lac repressor phenotype in vivo in *Escherichia coli*. Peer J e498
49. Szymczak A L, Vignali D A (2005) Development of 2A peptide-based strategies in the design of multicistronic vectors. Expert Opin Biol Ther 5: 627-638
50. Ptashne, M. *A Genetic Switch: Phage Lambda Revisited*. (2004).
51. Maloy, S. & Stewart, V. Autogenous regulation of gene expression. *J. Bacteriol.* 175, 307-16 (1993).
52. Oehler, S., et al, 1994 Quality and position of the three lac operators of *E. coli* define efficiency of repression. *EMBO J*. 13, 3348-3355.
53. Beilstein, K et al, 2015 May, Conditional control of mammalian gene expression by tetracycline-dependent hammerhead ribozyme. ACS Synth Biol., 4(5):526-534

The invention claimed is:

1. A self-regulating inducible gene expression construct comprising in operative association,
   (a) a single promoter controlling expression of a tetracycline bacterial repressor sequence (tetR) and a transgene;
   (b) one or more operator sequences responsive to the expressed repressor protein;
   (c) the tetR bacterial repressor gene sequence, said repressor sequence capable of interacting with a first inducer molecule and thereby initiating transcription by the promoter;
   (d) a 2A sequence;
   (e) a selected the transgene sequence, which is separated from the repressor sequence by the 2A sequence;
   (f) a ribozyme in association with an aptamer sequence, said aptamer sequence capable of interacting with a second inducer molecule to terminate mRNA degradation by the ribozyme, said ribozyme located upstream of a polyadenylation sequence;
   (g) the polyadenylation sequence; and
   (h) a 5' AAV ITR and a 3' AAV ITR flanking components (a) through (g);
   wherein when operative in a cell, in the absence of the first and second inducer molecules the combined operation of the repressor and ribozyme reduces transcription of the transgene and degrades any mRNA produced by basal levels of transcription, and in the presence of the first inducer and second inducer molecules, transcription of the transgene is increased.

2. A recombinant adeno-associated vector (rAAV) comprising an operational self-regulating inducible gene expression construct of claim 1.

3. The vector according to claim 2,
   further comprising AAV capsid proteins of serotype of any one of AAV 1 to 10, AAV8B, AAV7m8; tyrosine mutant capsid AAVs or other recombinant, synthetic or mutant AAV capsids.

4. A recombinant cell comprising the rAAV of claim 2.

5. A method of tightly regulating expression of a transgene in a mammalian cell comprising:
   (a) infecting the cell with a recombinant vector comprising an operational self-regulating inducible gene expression construct of claim 1, wherein the gene construct is stably expressed by the infected cell; and
   (b) contacting the cell in vivo with a first inducing molecule that interacts with the repressor to permit simultaneous expression of the transgene and repressor protein by the single promoter;
   (c) contacting the cell in vivo with a second inducing molecule that interacts with the aptamer to prevent the ribozyme from degrading the transcribed message;
   (d) discontinuing the first inducing molecule which permitting the repressor protein to autoregulate and reduce or inhibit transcription of the repressor protein and the transgene as the repressor protein accumulates in the cells and interacts with the operator sequence in the absence of additional amounts of the molecule; and
   (e) discontinuing the second inducing molecule, which permits the ribozyme to degrade any further transcription of the repressor and transgene.

6. A method of controlling expression of a transgene in a mammalian cell comprising:
   infecting the cell with the recombinant vector of claim 2, wherein the gene construct is stably expressed by the infected cell; and
   expressing a transgene in the cell by contacting the cell in vivo with an inducing molecule that interacts with the repressor to permit simultaneous expression of the transgene and repressor protein by the single promoter; and
   permitting the repressor protein to autoregulate and reduce or inhibit expression of the repressor protein and the transgene as the repressor protein accumulates in the cells and interacts with the operator sequence in the absence of additional amounts of the molecule.

7. The method according to claim 6, further comprising repeatedly expressing the transgene by subsequent contact with the inducing molecule.

8. The construct according to claim 1, wherein the first inducer molecule and the second inducer molecule are the same molecule.

9. The construct according to claim 1, wherein the inducing molecule or first inducing molecule is tetracycline.

10. The construct according to claim 1, wherein the aptamer binds tetracycline and the second inducing molecule is tetracycline.

11. The construct according to claim 1, wherein the transgene encodes a human gene for expression in selected human cell.

12. The construct according to claim 1, wherein the cell is an ocular cell and the transgene is RHO, LCA5, CHM, ABCA4, RPE65, RDH12, CEP290, RPGR, PRPF31, or CNGB3.

13. The construct according to claim 1, wherein each component of the construct is codon optimized for expression in human cells.

14. The construct according to claim 1, wherein the promoter is a single minimal CMV1 promoter/enhancer controlling expression of the repressor sequence and transgene.

15. The construct according to claim 1, wherein the ribozyme is a hammerhead ribozyme in association with a tetracycline-binding aptamer.

16. A recombinant AAV for controllable expression of a therapeutic transgene in a cell comprising the construct of claim 1, wherein the promoter is a single minimal CMV1 promoter/enhancer controlling expression of the repressor sequence and transgene and the ribozyme is a hammerhead ribozyme in association with a tetracycline-binding aptamer.

* * * * *

SEQUENCE LISTING

<160> NUMBER OF SEQ ID NOS: 15

<210> SEQ ID NO 1
<211> LENGTH: 7808
<212> TYPE: DNA
<213> ORGANISM: Artificial Sequence
<220> FEATURE:
<223> OTHER INFORMATION: Synthetic construct containing minimal CMVI
      promoter, optimized E. coli Lac 1operator (Lsym), yellow
      fluorescent protein reporter gene separated by an IRES sequence
      from an E. coli lac repressor sequence, C-terminal tag

<400> SEQUENCE: 1
cttccgcttc ctcgctcact gactcgctgc gctcggtcgt tcggctgcgg cgagcggtat      60
cagctcactc aaaggcggta atacggttat ccacagaatc aggggataac gcaggaaaga     120
acatgtgagc aaaaccgcag caaaaggcca ggaaccgtaa aaaggccgcg ttgctggcgt     180
ttttccatag gctccgcccc cctgacgagc atcacaaaaa tcgacgctca agtcagaggt     240
ggcgaaaccc gacaggacta taaagatacc aggcgtttcc ccctggaagc tccctcgtgc     300
gctctcctgt tccgaccctg ccgcttaccg gatacctgtc cgcctttctc ccttcgggaa     360
gcgtggcgct ttctcatagc tcacgctgta ggtatctcag ttcggtgtag gtcgttcgct     420
ccaagctggg ctgtgtgcac gaaccccccg ttcagcccga ccgctgcgcc ttatccggta     480
actatcgtct tgagtccaac ccggtaagac acgacttatc gccactggca gcagccactg     540
gtaacaggat tagcagagcg aggtatgtag gcggtgctac agagttcttg aagtggtggc     600
ctaactacgg ctacactaga aggacagtat ttggtatctg cgctctgctg aagccagtta     660
ccttcggaaa aagagttggt agctcttgat ccggcaaaca accaccgct ggtagcggtg     720 gtttttttgt ttgcaagcag cagattacgc gcagaaaaaa aggatctcaa gaagatcctt     780
tgatcttttc tacggggtct gacgctcagt ggaacgaaaa ctcacgttaa gggattttgg     840
tcatgagatt atcaaaaagg atcttcacct agatcctttt aaattaaaaa tgaagtttta     900
aatcaatcta aagtatatat gagtaaactt ggtctgacag ttaccaatgc ttaatcagtg     960
aggcacctat ctcagcgatc tgtctatttc gttcatccat agttgcctga ctccccgtcg    1020

```
tgtagataac tacgatacgg gagggcttac catctggccc cagtgctgca atgataccgc      1080
gagacccacg ctcaccggct ccagatttat cagcaataaa ccagccagcc ggaagggccg      1140
agcgcagaag tggtcctgca actttatccg cctccatcca gtctattaat tgttgccggg      1200
aagctagagt aagtagttcg ccagttaata gtttgcgcaa cgttgttacc attactacag      1260
gcatcgtggt gtcacgctcg tcgtttggta tggcttcatt cagctccggt tcccaacgat      1320
caaggcgagt tacatgatcc cccatgttgt gcaaaaaagc ggttagctcc ttcggtcctc      1380
cgatcgttgt cagaagtaag ttggccgcag tgttatcact catggttatg gcagcactgc      1440
ataattctct tactgtcatg ccatccgtaa gatgcttttc tgtgactggt gagtactcaa      1500
ccaagtcatt ctgagaatag tgtatgcggc gaccgagttg ctcttgcccg cgtcaatac       1560 gggataatac cgcgccacat agcagaactt taaaagtgct catcattgga aaacgttctt      1620
cggggcgaaa actctcaagg atcttaccac tattgagatc cagttcgatg taacccactc      1680
gtgcacccaa ctgatcttca gcatctttta ctttcaccag cgtttctggg tgagcaaaaa      1740
caggaaggca aaatgccgca aaaagggaa  taagggcgac acggaaatgt tgaatactca      1800
tactcttcct ttttcaatat tattgaagca tttatcaggg ttattgtctc atgagcggat      1860
acatatttga atgtatttag aaaaataaac aaataggggg tccgcgcaca tttccccgaa      1920
agatgccacc tgaaattata acgttaata  ttttgttaaa attcgcgtta aattttttgtt     1980 aaatcagctc attttttaac cataggccg  aaatcggaaa aatcccttat aaatcaaaag      2040
aatagaccga gatagggttg agtgttgttc cagtttggaa caagagtcca ctattgagga      2100
acgtgaactc cagcgtcaaa gggcgaaaaa ccgtctatcg gggcgatggc ccactacgtg      2160
aaccatcacc ctaatcaagt tttttggggt cgaggtgccg taaagcacta atcggaacc       2220 ctaaagggag cccccgattt agagcttgac ggggaaagcc ggcgaacgtg gcgagaaagg      2280
aagggaagaa agcgaaagga gcgggcgcta gggcgctggc aagtgtagcg gtcacgctgc      2340
gcgtaaccac cacacccgcc gcgcttaatg cgccgctaca gggcgcgtcc cattcgccat      2400
tcaggctgcg caactgttgg gaagggcgat cggtgcgggc ctcttcgcta ttacgccagc      2460
tggcgaaagg gggatgtgct gcaaggcgat taagttgggt aacgccaggg ttttcccagt      2520
cacgacgttg taaaacgacg gccagtgaat taggttaatt aaggctgcgc gctcgctcgc      2580
tcactgagcg cgcccgggca aagcccgggc gtcgggcgac ctttggtcgc ccggcctcag      2640
tgagcgagcg agcgcgcaga gagggagtgg ccaactccat cactaggggt tccttgtagt      2700
taatgattaa cccgccatgc tacttatcta cgtagccatg ctctaggaag atcctaatcg      2760
ggaattctca atattggcca ttagccatat tattcattgg ttatatagca taaatcaata      2820
ttggctattg gccattgcat acgttgtatc tatatcataa tatgtacatt tatattggct      2880
catgtccaat atgaccgcca tgttggcatt gattattgac tagttattaa tagtaatcaa      2940
ttacggggtc attagttcat agcccatata tggagttccg cgttacataa cttacgtaa       3000 atggcccgcc tggctgaccg cccaacgacc cccgcccatt gacgtcaata atgacgtatg      3060
ttcccatagt aacgccaata gggactttcc attgacgtca atgggtggag tatttacggt      3120
aaactgccca cttggcagta catcaagtgt atcatatgcc aagtccgccc cctattgacg      3180
tcaatgacgg taaatggccc gcctggcatt atgcccagta catgacctta cgggactttc      3240
ctacttggca gtacatctac gtattagtca tcgctattac catggtgatg cggttttggc      3300
agtacaccaa tgggcgtgga tagcggtttg actcacgggg atttccaagt ctccacccca     3360
ttgacgtcaa tgggagtttg ttttggcacc aaaatcaacg ggactttcca aaatgtcgta     3420
```

```
acaactgcga tcgcccgccc cgttgacgca aatgggcggt aggcgtgtac ggtgggaggt    3480
ctatataagc agagctcgaa ttgtgagcgc tcacaattga gctcgtttag tgaaccgtca    3540
gatcactaga agctttattg cggtagttta tcacagttaa attgctaacg cagtcagtgc    3600
ttctgacaca acagtctcga acttaagctg cagtgactct cttaaggtag ccttgcagaa    3660
gttggtcgtg aggcactggg caggtaagta tcaaggttac aagacaggtt taaggagacc    3720
aatagaaact gggcttgtcg agacagagaa gactcttgcg tttctgatag cacctattg     3780 gtcttactga catccacttt gcctttctct ccacaggtgt ccactcccag ttcaattaca    3840
gctcttaagg ctagagtact taatacgact cactataggc tagcctcagt aaaggagaag    3900
aacttttcac tggagttgtc ccaattcttg ttgaattaga tggtgatgtt aatgggcaca    3960
aattttctgt cagtggagag ggtgaaggtg atgcaacata cggaaaactt acccttaaat    4020
ttatttgcac tactggaaaa ctacctgttc catggccaac acttgtcact actttcggtt    4080
atggtctaaa atgctttgct agatacccag atcatatgaa acggcatgac ttttcaaga    4140 gtgccatgcc cgaaggttat gtacaggaaa gaactatatt tttcaaagat gacgggaact    4200
acaagacacg tgctgaagtc aagtttgaag gtgataccct tgttaataga atcgagttaa    4260
aaggtattga ttttaaagaa gatggaaaca ttcttggaca caaattggaa tacaactata    4320
actcacacaa tgtatacatc atggcagaca acaaaagaa tggaatcaaa gttaacttca    4380
aaattagaca caacattgaa gatggaagcg ttcaactagc agaccattat caacaaaata    4440
ctccaattgg cgatggccct gtccttttac cagacaacca ttacctgtcc tatcaatctg    4500 cccttttcgaa agatcccaac gaaaagagag accacatggt ccttcttgag tttgtaacag    4560
ctgctgggat tacacatggc atggatgaac tatacaaaga gaattcacgc gtcgagcatg    4620
catctagggc ggccaattcc gcccctctcc cccccccccc tctccctccc ccccccctaa    4680
cgttactggc cgaagccgct tggaataagg ccggtgtgcg tttgtctata tgttattttc    4740
caccatattg ccgtcttttg gcaatgtgag ggcccggaaa cctggccctg tcttcttgac    4800
gagcattcct aggggtcttt cccctctcgc caaaggaatg caaggtctgt tgaatgtcgt    4860
gaaggaagca gttcctctgg aagcttcttg aagacaaaca acgtctgtag cgaccctttg    4920
caggcagcgg aaccccccac ctggcgacag gtgcctctgc ggccaaaagc cacgtgtata    4980
agatacacct gcaaaggcgg cacaaccca gtgccacgtt gtgagttgga tagttgtgga    5040
aagagtcaaa tggctctcct caagcgtatt caacaagggg ctgaaggatg cccagaaggt    5100
accccattgt atgggatctg atctgggggcc tcggtgcaca tgctttacat gtgtttagtc    5160
gaggttaaaa aaacgtctag gccccccgaa ccacggggac gtggttttcc tttgaaaaac    5220
acgatgataa gcttgccaca acccgggatc tatgaaacca gtaacgttat acgacgtcgc    5280
agagtatgcc ggtgtctctt atcagactgt ttccagagtg gtgaaccagg ccagccatgt    5340
ttctgccaaa accagggaaa aagtggaagc agccatggca gagctgaatt acattcccaa    5400
cagagtggca caacaactgg caggcaaaca gagcttgctg attggagttg ccacctccag    5460
tctggccctg catgcaccat ctcaaattgt ggcagccatt aaatctagag ctgatcaact    5520
gggagcctct gtggtggtgt caatggtaga aagaagtgga gttgaagcct gtaaagctgc    5580
agtgcacaat cttctggcac aaagagtcag tgggctgatc attaactatc cactggatga    5640
ccaggatgcc attgctgtgg aagctgcctg cactaatgtt ccagcactct tcttgatgct    5700
ctctgaccag acacccatca acagtattat tttctcccat gaagatggta caagactggg    5760
```

```
tgtggagcat ctggttgcat tgggacacca gcaaattgca ctgcttgcgg gcccactcag    5820
ttctgtctca gcaaggctga gactggccgg ctggcataaa tatctcacta ggaatcaaat    5880
tcagccaata gctgaaagag aaggggactg gagtgccatg tctgggtttc aacaaaccat    5940
gcaaatgctg aatgagggca ttgttcccac tgcaatgctg gttgccaatg atcagatggc    6000
actgggtgca atgagagcca ttactgagtc tgggctgaga gttggtgcag atatctcggt    6060
agtgggatac gacgataccg aagacagctc atgttatatc cgccgttaa ccaccatcaa     6120 acaggatttt cgcctgctgg ggcaaaccag cgtggaccgc ttgctgcaac tctctcaggg    6180
ccaggcggtg aagggcaatc agctgttgcc agtctcactg gtgaagagaa aaaccaccct    6240
ggcacccaat acacaaactg cctctccccg ggcattggct gattcactca tgcagctggg    6300
ctcaggtctc gagttggtgg tgagcaaggg cgaggaggat aacatggcca tcatcaagga    6360
gttcatgcgc ttcaaggtgc acatggaggg ctccgtgaac ggccacgagt tcgagatcga    6420
gggcgagggc gagggccgcc cctacgaggg cacccagacc gccaagctga aggtgaccaa    6480
gggtggcccc ctgcccttcg cctgggacat cctgtcccct cagttcatgt acggctccaa    6540
ggcctacgtg aagcaccccg ccgacatccc cgactacttg aagctgtcct tccccgaggg    6600
cttcaagtgg gagcgcgtga tgaacttcga ggacggcggc gtggtgaccg tgacccagga    6660
ctcctccctg caggacggcg agttcatcta caaggtgaag ctgcgcggca ccaacttccc    6720
ctccgacggc cccgtaatgc agaagaagac catgggctgg gaggcctcct ccgagcggat    6780 gtacccccgag gacggcgccc tgaagggcga gatcaagcag aggctgaagc tgaaggacgg    6840
cggccactac gacgctgagg tcaagaccac ctacaaggcc aagaagcccg tgcagctgcc    6900
cggcgcctac aacgtcaaca tcaagttgga catcacctcc cacaacgagg actacaccat    6960
cgtggaacag tacgaacgcg ccgagggccg ccactccacc ggcggcatgg acgagctgta    7020
caaggcaaga caggtttcca gactggaaag tgggcaggca gctctgccca gaagaagcg     7080 aaaggtgtga tagagtcgac ccgggcggcc gcttcccttt agtgagggtt aatgcttcga    7140
gcagacatga taagatacat tgatgagttt ggacaaacca caactagaat gcagtgaaaa    7200
aaatgcttta tttgtgaaat ttgtgatgct attgctttat ttgtaaccat tataagctgc    7260
aataaacaag ttaacaacaa caattgcatt cattttatgt ttcaggttca ggggggagatg     7320 tgggaggttt tttaaagcaa gtaaaacctc tacaaatgtg gtaaagaatt ccgatcttcc     7380
tagagcatgg ctacgtagat aagtagcatg gcgggttaat cattaactac aaggaacccc    7440
tagtgatgga gttggccact ccctctctgc gcgctcgctc gctcactgag gccgggcgac    7500
caaaggtcgc ccgacgcccg ggctttgccc gggcggcctc agtgagcgag cgagcgcgca    7560
gccttaatta aatctggcgt aatcatggtc atagctgttt cctgtgtgaa attgttatcc    7620
gctcacaatt ccacacaaca tacgagccgg aagcataaag tgtaaagcct ggggtgccta    7680
atgagtgagc taactcacat taattgcgtt gcgctcactg cccgctttcc agtcgggaaa    7740
cctgtcgtgc cagctgcatt aatgaatcgg ccaacgcgcg gggagaggcg gtttgcgtat    7800
tgggcgct                                                             7808
```

<210> SEQ ID NO 2
<211> LENGTH: 11255
<212> TYPE: DNA
<213> ORGANISM: Artificial Sequence
<220> FEATURE:
<223> OTHER INFORMATION: Synthetic construct containing minimal CMVI
      promoter having two Lsym sites, a green fluorescent protein
      reporter gene separated by a 2A cleavage sequence from the E. coli lac repressor sequence.

<400> SEQUENCE: 2

```
ggccgcagat tacaaggatg acgatgacaa gtaaagtact gacatgataa gatacattga        60
tgagtttgga caaaccacaa ctagaatgca gtgaaaaaaa tgctttattt gtgaaatttg       120
tgatgctatt gctttatttg taaccattat aagctgcaat aaacaagtta acaacaacaa       180
ttgcattcat tttatgtttc aggttcaggg ggagatgtgg gaggttttt aaagcaagta        240
aaacctctac aaatgtggta aactcgagtt ctacgtagat aagtagcatg gcgggttaat       300
cattaactac aaggaacccc tagtgatgga gttggccact ccctctctgc gcgctcgctc       360
gctcactgag gccgggcgac caaggtcgc ccgacgcccg ggctttgccc gggcggcctc        420
agtgagcgag cgagcgcgca gccttaatta acctaaggaa aatgaagtga agttcctata       480
ctttctagag aataggaact tctatagtga gtcgaataag ggcgacacaa aatttattct       540
aaatgcataa taaatactga taacatctta tagtttgtat tatattttgt attatcgttg       600
acatgtataa ttttgatatc aaaaactgat tttcccttta ttattttcga gatttatttt       660
cttaattctc tttaacaaac tagaaatatt gtatatacaa aaaatcataa ataatagatg       720
aatagtttaa ttataggtgt tcatcaatcg aaaaagcaac gtatcttatt taaagtgcgt       780
tgcttttttc tcatttataa ggttaaaataa ttctcatata tcaagcaaag tgacaggcgc       840
ccttaaatat tctgacaaat gctctttccc taaactcccc ccataaaaaa acccgccgaa       900
gcgggttttt acgttatttg cggattaacg attactcgtt atcagaaccg cccagggggc       960
ccgagcttaa cctttttatt tggggagag ggaagtcatg aaaaaactaa cctttgaaat       1020
tcgatctcca gcacatcagc aaaacgctat tcacgcagta cagcaaatcc ttccagaccc      1080
aaccaaacca atcgtagtaa ccattcagga acgcaaccgc agcttagacc aaaacaggaa      1140
gctatgggcc tgcttaggtg acgtctctcg tcaggttgaa tggcatggtc gctggctgga      1200
tgcagaaagc tggaagtgtg tgtttaccgc agcattaaag cagcaggatg ttgttcctaa      1260
ccttgccggg aatggctttg tggtaatagg ccagtcaacc agcaggatgc gtgtaggcga      1320
atttgcggag ctattagagc ttatacaggc attcggtaca gagcgtggcg ttaagtggtc      1380
agacgaagcg agactggctc tggagtggaa agcgagatgg ggagacaggg ctgcatgata      1440
aatgtcgtta gttctccgg tggcaggacg tcagcatatt tgctctggct aatggagcaa       1500
aagcgacggg caggtaaaga cgtgcattac gttttcatgg atacaggttg tgaacatcca      1560
atgacatatc ggtttgtcag ggaagttgtg aagttctggg atataccgct caccgtattg      1620
caggttgata tcaacccgga gcttggacag ccaaatggtt atacggtatg gaaccaaag      1680
gatattcaga cgcgaatgcc tgttctgaag ccatttatcg atatggtaaa gaatatggc      1740
actccatacg tcggcggcgc gttctgcact gacagattaa aactcgttcc cttcaccaaa      1800
tactgtgatg accatttcgg gcgagggaat tacaccacgt ggattggcat cagagctgat      1860
gaaccgaagc ggctaaagcc aaagcctgga atcagatatc ttgctgaact gtcagacttt      1920
gagaaggaag atatcctcgc atggtggaag caacaaccat tcgatttgca ataccggaa      1980
catctcggta actgcatatt ctgcattaaa aaatcaacgc aaaaaatcgg acttgcctgc      2040
aaagatgagg agggattgca gcgtgttttt aatgaggtca tcacgggatc ccatgtgcgt      2100
gacggacatc gggaaacgcc aaaggagatt atgtaccgag gaagaatgtc gctggacggt      2160
atcgcgaaaa tgtattcaga aaatgattat caagccctgt atcaggacat ggtacgagct      2220
aaaagattcg ataccggctc ttgttctgag tcatgcgaaa tatttggagg cagcttgat      2280
```

```
ttcgacttcg ggagggaagc tgcatgatgc gatgttatcg gtgcggtgaa tgcaaagaag    2340
ataaccgctt ccgaccaaat caaccttact ggaatcgatg gtgtctccgg tgtgaaagaa    2400
caccaacagg ggtgttacca ctaccgcagg aaaaggagga cgtgtggcga gacagcgacg    2460
aagtatcacc gacataatct gcgaaaactg caaatacctt ccaacgaaac gcaccagaaa    2520
taaacccaag ccaatcccaa aagaatctga cgtaaaaacc ttcaactaca cggctcacct    2580
gtgggatatc cggtggctaa gacgtcgtgc gaggaaaaca aggtgattga ccaaaatcga    2640
agttacgaac aagaaagcgt cgagcgagct ttaacgtgcg ctaactgcgg tcagaagctg    2700
catgtgctgg aagttcacgt gtgtgagcac tgctgcgcag aactgatgag cgatccgaat    2760
agctcgatgc acgaggaaga agatgatggc taaaccagcg cgaagacgat gtaaaaacga    2820
tgaatgccgg gaatggtttc accctgcatt cgctaatcag tggtggtgct ctccagagtg    2880
tggaaccaag atagcactcg aacgacgaag taaagaacgc gaaaaagcgg aaaaagcagc    2940
agagaagaaa cgacgacgag aggagcagaa acagaaagat aaacttaaga ttcgaaaact    3000
cgccttaaag ccccgcagtt actggattaa acaagcccaa caagccgtaa acgccttcat    3060
cagagaaaga gaccgcgact taccatgtat ctcgtgcgga acgctcacgt ctgctcagtg    3120
ggatgccgga cattaccgga caactgctgc ggcacctcaa ctccgattta atgaacgcaa    3180
tattcacaag caatgcgtgg tgtgcaacca gcacaaaagc ggaaatctcg ttccgtatcg    3240
cgtcgaactg attagccgca tcgggcagga agcagtagac gaaatcgaat caaaccataa    3300
ccgccatcgc tggactatcg aagagtgcaa ggcgatcaag gcagagtacc aacagaaact    3360
caaagacctg cgaaatagca gaagtgaggc cgcatgacgt tctcagtaaa aaccattcca    3420
gacatgctcg ttgaagcata cggaaatcag acagaagtag cacgcagact gaaatgtagt    3480
cgcggtacgg tcagaaaata cgttgatgat aaagacggga aaatgcacgc catcgtcaac    3540
gacgttctca tggttcatcg cggatggagt gaaagagatg cgctattacg aaaaaattga    3600
tggcagcaaa taccgaaata tttgggtagt tggcgatctg cacggatgct acacgaacct    3660
gatgaacaaa ctggatacga ttggattcga caacaaaaaa gacctgctta tctcggtggg    3720
cgatttggtt gatcgtggtg cagagaacgt tgaatgcctg gaattaatca cattcccctg    3780
gttcagagct gtacgtggaa accatgagca aatgatgatt gatggcttat cagagcgtgg    3840
aaacgttaat cactggctgc ttaatggcgg tggctggttc tttaatctcg attacgacaa    3900
agaaattctg gctaaagctc ttgcccataa agcagatgaa cttccgttaa tcatcgaact    3960
ggtgagcaaa gataaaaaat atgttatctg ccacgccgat tatccctttg acgaatacga    4020
gtttggaaag ccagttgatc atcagcaggt aatctggaac cgcgaacgaa tcagcaactc    4080
acaaaacggg atcgtgaaag aaatcaaagg cgcggacacg ttcatctttg gtcatacgcc    4140
agcagtgaaa ccactcaagt ttgccaacca aatgtatatc gataccggcg cagtgttctg    4200
cggaaaccta acattgattc aggtacaggg agaaggcgca tgagactcga aagcgtagct    4260
aaatttcatt cgccaaaaag cccgatgatg agcgactcac cacgggccac ggcttctgac    4320
tctctttccg gtactgatgt gatggctgct atggggatgg cgcaatcaca agccggattc    4380
ggtatggctg cattctgcgg taagcacgaa ctcagccaga acgacaaaca aaaggctatc    4440
aactatctga tgcaatttgc acacaaggta tcggggaaat accgtggtgt ggcaaagctt    4500
gaaggaaata ctaaggcaaa ggtactgcaa gtgctcgcaa cattcgctta tgcggattat    4560
tgccgtagtg ccgcgacgcc gggggcaaga tgcagagatt gccatggtac aggccgtgcg    4620
```

```
gttgatattg ccaaaacaga gctgtggggg agagttgtcg agaaagagtg cggaagatgc      4680
aaaggcgtcg gctattcaag gatgccagca agcgcagcat atcgcgctgt gacgatgcta      4740
atcccaaacc ttacccaacc cacctggtca cgcactgtta agccgctgta tgacgctctg      4800
gtggtgcaat gccacaaaga agagtcaatc gcagacaaca ttttgaatgc ggtcacacgt      4860
tagcagcatg attgccacgg atggcaacat attaacggca tgatattgac ttattgaata      4920
aaattgggta aatttgactc aacgatgggt taattcgctc gttgtggtag tgagatgaaa      4980
agaggcggcg cttactaccg attccgccta gttggtcact tcgacgtatc gtctggaact      5040
ccaaccatcg caggcagaga ggtctgcaaa atgcaatccc gaaacagttc gcaggtaata      5100
gttagagcct gcataacggt tcgggatttt tttatatctg cacaacaggt aagagcattg      5160
agtcgataat cgtgaagagt cggcgagcct ggttagccag tgctcttttcc gttgtgctga      5220 attaagcgaa taccggaagc agaaccggat caccaaatgc gtacaggcgt catcgccgcc      5280
cagcaacagc acaacccaaa ctgagccgta gccactgtct gtcctgaatt cattagtaat      5340
agttacgctg cggcctttta cacatgacct tcgtgaaagc gggtggcagg aggtcgcgct      5400
aacaacctcc tgccgttttg cccgtgcata tcggtcacga acaaatctga ttactaaaca      5460
cagtagcctg gatttgttct atcagtaatc gaccttattc ctaattaaat agagcaaatc      5520
cccttattgg gggtaagaca tgaagatgcc agaaaaacat gacctgttgg ccgccattct      5580
cgcggcaaag gaacaaggca tcggggcaat ccttgcgttt gcaatggcgt accttcgcgg      5640
cagatataat ggcggtgcgt ttacaaaaac agtaatcgac gcaacgatgt gcgccattat      5700
cgcctggttc attcgtgacc ttctcgactt cgccggacta agtagcaatc tcgcttatat      5760
aacgagcgtg tttatcggct acatcggtac tgactcgatt ggttcgctta tcaaacgctt      5820
cgctgctaaa aaagccggag tagaagatgg tagaaatcaa taatcaacgt aaggcgttcc      5880
tcgatatgct ggcgtggtcg gagggaactg ataacggacg tcagaaaacc agaaatcatg      5940
gttatgacgt cattgtaggc ggagagctat ttactgatta ctccgatcac cctcgcaaac      6000
ttgtcacgct aaacccaaaa ctcaaatcaa caggcgctta agactggccg tcgttttaca      6060
acacagaaag agtttgtaga aacgcaaaaa ggccatccgt caggggcctt ctgcttagtt      6120
tgatgcctgg cagttcccta ctctcgcctt ccgcttcctc gctcactgac tcgctgcgct      6180
cggtcgttcg gctgcggcga gcggtatcag ctcactcaaa ggcggtaata cggttatcca      6240
cagaatcagg ggataacgca ggaaagaaca tgtgagcaaa aggccagcaa aaggccagga      6300
accgtaaaaa ggccgcgttg ctggcgtttt tccataggct ccgcccccct gacgagcatc      6360
acaaaaatcg acgctcaagt cagaggtggc gaaacccgac aggactataa agataccagg      6420
cgtttccccc tggaagctcc ctcgtgcgct ctcctgttcc gaccctgccg cttaccggat      6480
acctgtccgc ctttctccct tcgggaagcg tggcgctttc tcatagctca cgctgtaggt      6540
atctcagttc ggtgtaggtc gttcgctcca agctgggctg tgtgcacgaa ccccccgttc      6600
agcccgaccg ctgcgcctta tccggtaact atcgtcttga gtccaacccg gtaagacacg      6660
acttatcgcc actggcagca gccactggta acaggattag cagagcgagg tatgtaggcg      6720
gtgctacaga gttcttgaag tggtgggcta actacggcta cactagaaga acagtatttg      6780
gtatctgcgc tctgctgaag ccagttacct tcggaaaaag agttggtagc tcttgatccg      6840
gcaaacaaac caccgctggt agcggtggtt tttttgtttg caagcagcag attacgcgca      6900
gaaaaaaagg atctcaagaa gatcctttga tcttttctac ggggtctgac gctcagtgga      6960
acgacgcgcg cgtaactcac gttaagggat tttggtcatg agcttgcgcc gtcccgtcaa      7020
```

```
gtcagcgtaa tgctctgctt ttagaaaaac tcatcgagca tcaaatgaaa ctgcaattta    7080
ttcatatcag gattatcaat accatatttt tgaaaaagcc gtttctgtaa tgaaggagaa    7140
aactcaccga ggcagttcca taggatggca agatcctggt atcggtctgc gattccgact    7200
cgtccaacat caatacaacc tattaatttc ccctcgtcaa aaataaggtt atcaagtgag    7260
aaatcaccat gagtgacgac tgaatccggt gagaatggca aaagtttatg catttctttc    7320
cagacttgtt caacaggcca gccattacgc tcgtcatcaa aatcactcgc atcaaccaaa    7380
ccgttattca ttcgtgattg cgcctgagcg aggcgaaata cgcgatcgct gttaaaagga    7440
caattacaaa caggaatcga gtgcaaccgg cgcaggaaca ctgccagcgc atcaacaata    7500
ttttcacctg aatcaggata ttcttctaat acctggaacg ctgttttttcc ggggatcgca    7560 gtggtgagta accatgcatc atcaggagta cggataaaat gcttgatggt cggaagtggc    7620
ataaattccg tcagccagtt tagtctgacc atctcatctg taacatcatt ggcaacgcta    7680
cctttgccat gtttcagaaa caactctggc gcatcgggct tcccatacaa gcgatagatt    7740
gtcgcacctg attgcccgac attatcgcga gcccatttat acccatataa atcagcatcc    7800
atgttggaat ttaatcgcgg cctcgacgtt tcccgttgaa tatggctcat attcttcctt    7860
tttcaatatt attgaagcat ttatcagggt tattgtctca tgagcggata catatttgaa    7920
tgtatttaga aaaataaaca aataggggtc agtgttacaa ccaattaacc aattctgaac    7980
attatcgcga gcccatttat acctgaatat ggctcataac accccttgtt tgcctggcgg    8040
cagtagcgcg gtggtcccac ctgaccccat gccgaactca gaagtgaaac gccgtagcgc    8100
cgatggtagt gtggggactc cccatgcgag agtagggaac tgccaggcat caaataaaac    8160
gaaaggctca gtcgaaagac tgggcctttc gcccgggcta attaggggggt gtcgccctta    8220 ttcgactcta tagtgaagtt cctattctct agaaagtata ggaacttctg aagtgggggtc    8280 gacttaatta aggctgcgcg ctcgctcgct cactgaggcc gcccgggcaa agcccgggcg    8340
tcgggcgacc tttggtcgcc cggcctcagt gagcgagcga gcgcgcagag agggagtggc    8400
caactccatc actaggggtt ccttgtagtt aatgattaac cgccatgct acttatctac    8460 gtagcaagct agcctagtta ttaatagtaa tcaattacgg ggtcattagt tcatagccca    8520
tatatggagt tccgcgttac ataacttacg gtaaatggcc cgcctggctg accgcccaac    8580 gaccccccgcc cattgacgtc aataatgacg tatgttccca tagtaacgcc aatagggact    8640
ttccattgac gtcaatgggt ggagtattta cggtaaactg cccacttggc agtacatcaa    8700
gtgtatcata tgccaagtac gccccctatt gacgtcaatg acggtaaatg gcccgcctgg    8760
cattatgccc agtacatgac cttatgggac tttcctactt ggcagtacat ctacgtatta    8820
gtcatcgcta ttaccatggt gatgcggttt tggcagtaca ccaatgggcg tggatagcgg    8880
tttgactcac ggggatttcc aagtctccac cccattgacg tcaatgggag tttgttttgg    8940
caccaaaatc aacgggactt tccaaaatgt cgtaacaact ccgccccgtt gacgcaaatg    9000
ggcggtaggc gtgtacggtg ggaggtctat ataagcagag ctcgaattgt gagcgctcac    9060
aattgaggtc gtttagtgaa ccgtcagatc gttggtcgtg aggcactggg caggtaagta    9120
tcaaggttac aagacaaatt gtgagcgctc acaattggtt taaggagacc aatagaaact    9180
gggcttgtcg agacagagaa gactcttgcg tttctgatag gcacctattg gtcttactga    9240
catccacttt gcctttctct ccacaggtgt ccactcccag ttcaattaca gatcaggcct    9300
accatgaaac cagtaacgtt atacgacgtc gcagagtatg ccggtgtctc ttatcagact    9360
```

```
gtttccagag tggtgaacca ggccagccat gtttctgcca aaaccaggga aaaagtggaa    9420
gcagccatgg cagagctgaa ttacattccc aacagagtgg cacaacaact ggcaggcaaa    9480
cagagcttgc tgattggagt tgccacctcc agtctggccc tgcatgcacc atctcaaatt    9540
gtggcagcca ttaaatctag agctgatcaa ctgggagcct ctgtggtggt gtcaatggta    9600
gaaagaagtg gagttgaagc ctgtaaagct gccgtgcaca atcttctggc acaaagagtc    9660
agtgggctga tcattaacta tccactggat gaccaggatg ccattgctgt ggaagctgcc    9720
tgcactaatg ttccagcact ctttcttgat gtctctgacc agacacccat caacagtatt    9780
attttctccc atgaagatgg tacaagactg gtgtggagc atctggttgc attgggacac    9840
cagcaaattg cactgcttgc gggcccactc agttctgtct cagcaaggct gagactggcc    9900
ggctggcata aatatctcac taggaatcaa attcagccaa tagctgaaag agaaggggac    9960
tggagtgcca tgtctgggtt tcaacaaacc atgcaaatgc tgaatgaggg cattgttccc    10020
actgcaatgc tggttgccaa tgatcagatg gcactgggtg caatgagagc cattactgag    10080
tctgggctga gagttggtgc agatatctcg gtagtggat acgacgatac cgaagacagc    10140
tcatgttata tcccgccgtt aaccaccatc aaacaggatt ttcgcctgct ggggcaaacc    10200
agcgtggacc gcttgctgca actctctcag gccaggcgg tgaagggcaa tcagctgttg    10260
ccagtctcac tggtgaagag aaaaaccacc ctggcaccca atacacaaac tgcctctccc    10320
cgggcattgg ctgattcact catgcagctg actagtgcac acaggtttc ccgactggaa    10380 agcgggcaga ctagtgcaag acaggtttcc agactggaaa gtgggcaggc agctctgccc    10440
aagaagaagc gaaggtgct gcagggaagc ggagctacta acttcagcct gctgaagcag    10500
gctggagacg tggaggagaa ccctggacct agatctatgg ccagcaaagg agaagaactt    10560
ttcactggag ttgtcccaat tcttgttgaa ttagatggtg atgttaatgg cacaaatt    10620 tctgtcagtg gagagggtga aggtgatgct acatacggaa agcttaccct taaatttatt    10680
tgcactactg gaaaactacc tgttccatgg ccaacacttg tcactacttt ctcttatggt    10740
gttcaatgct tttcccgtta tccggatcat atgaaacggc atgacttttt caagagtgcc    10800
atgcccgaag ttatgtaca ggaacgcact atatctttca agatgacgg aactacaag    10860 acgcgtgctg aagtcaagtt tgaaggtgat acccttgtta atcgtatcga gttaaaggt    10920 attgattta aagaagatgg aaacattctc ggacacaaac tcgagtacaa ctataactca    10980
cacaatgtat acatcacggc agacaaacaa aagaatggaa tcaaagctaa cttcaaaatt    11040
cgccacaaca ttgaagatgg atccgttcaa ctagcagacc attatcaaca aaatactcca    11100
attggcgatg gccctgtcct tttaccagac aaccattacc tgtcgacaca atctgccctt    11160
tcgaaagatc ccaacgaaaa gcgtgaccac atggtccttc ttgagtttgt aactgctgct    11220
gggattacac atggcatgga tgagctctac aaagc                              11255
```

<210> SEQ ID NO 3
<211> LENGTH: 360
<212> TYPE: PRT
<213> ORGANISM: Escherichia coli

<400> SEQUENCE: 3

```
Met Lys Pro Val Thr Leu Tyr Asp Val Ala Glu Tyr Ala Gly Val Ser
1               5                   10                  15

Tyr Gln Thr Val Ser Arg Val Val Asn Gln Ala Ser His Val Ser Ala
            20                  25                  30

Lys Thr Arg Glu Lys Val Glu Ala Ala Met Ala Glu Leu Asn Tyr Ile
```

```
            35                  40                  45
Pro Asn Arg Val Ala Gln Gln Leu Ala Gly Lys Gln Ser Leu Leu Ile
 50                  55                  60
Gly Val Ala Thr Ser Ser Leu Ala Leu His Ala Pro Ser Gln Ile Val
 65                  70                  75                  80
Ala Ala Ile Lys Ser Arg Ala Asp Gln Leu Gly Ala Ser Val Val Val
                 85                  90                  95
Ser Met Val Glu Arg Ser Gly Val Glu Ala Cys Lys Ala Ala Val His
            100                 105                 110
Asn Leu Leu Ala Gln Arg Val Ser Gly Leu Ile Ile Asn Tyr Pro Leu
        115                 120                 125
Asp Asp Gln Asp Ala Ile Ala Val Glu Ala Ala Cys Thr Asn Val Pro
    130                 135                 140
Ala Leu Phe Leu Asp Val Ser Asp Gln Thr Pro Ile Asn Ser Ile Ile
145                 150                 155                 160
Phe Ser His Glu Asp Gly Thr Arg Leu Gly Val Glu His Leu Val Ala
                165                 170                 175
Leu Gly His Gln Gln Ile Ala Leu Leu Ala Gly Pro Leu Ser Ser Val
            180                 185                 190
Ser Ala Arg Leu Arg Leu Ala Gly Trp His Lys Tyr Leu Thr Arg Asn
        195                 200                 205
Gln Ile Gln Pro Ile Ala Glu Arg Glu Gly Asp Trp Ser Ala Met Ser
    210                 215                 220
Gly Phe Gln Gln Thr Met Gln Met Leu Asn Glu Gly Ile Val Pro Thr
225                 230                 235                 240
Ala Met Leu Val Ala Asn Asp Gln Met Ala Leu Gly Ala Met Arg Ala
                245                 250                 255
Ile Thr Glu Ser Gly Leu Arg Val Gly Ala Asp Ile Ser Val Val Gly
            260                 265                 270
Tyr Asp Asp Thr Glu Asp Ser Ser Cys Tyr Ile Pro Pro Leu Thr Thr
        275                 280                 285
Ile Lys Gln Asp Phe Arg Leu Leu Gly Gln Thr Ser Val Asp Arg Leu
    290                 295                 300
Leu Gln Leu Ser Gln Gly Gln Ala Val Lys Gly Asn Gln Leu Leu Pro
305                 310                 315                 320
Val Ser Leu Val Lys Arg Lys Thr Thr Leu Ala Pro Asn Thr Gln Thr
                325                 330                 335
Ala Ser Pro Arg Ala Leu Ala Asp Ser Leu Met Gln Leu Ala Arg Gln
            340                 345                 350
Val Ser Arg Leu Glu Ser Gly Gln
        355                 360

<210> SEQ ID NO 4
<211> LENGTH: 340
<212> TYPE: PRT
<213> ORGANISM: Escherichia coli

<400> SEQUENCE: 4

Met Ala Thr Ile Lys Asp Val Ala Arg Leu Ala Gly Val Ser Val Ala
  1               5                  10                  15
Thr Val Ser Arg Val Ile Asn Asn Ser Pro Lys Ala Ser Glu Ala Ser
                 20                  25                  30
Arg Leu Ala Val His Ser Ala Met Glu Ser Leu Ser Tyr His Pro Asn
            35                  40                  45
```

Ala Asn Ala Arg Ala Leu Ala Gln Gln Thr Thr Glu Thr Val Gly Leu
 50                  55                  60

Val Val Gly Asp Val Ser Asp Pro Phe Phe Gly Ala Met Val Lys Ala
 65                  70                  75                  80

Val Glu Gln Val Ala Tyr His Thr Gly Asn Phe Leu Leu Ile Gly Asn
                 85                  90                  95

Gly Tyr His Asn Glu Gln Lys Glu Arg Gln Ala Ile Glu Gln Leu Ile
            100                 105                 110

Arg His Arg Cys Ala Ala Leu Val His Ala Lys Met Ile Pro Asp
        115                 120                 125

Ala Asp Leu Ala Ser Leu Met Lys Gln Met Pro Gly Met Val Leu Ile
130                 135                 140

Asn Arg Ile Leu Pro Gly Phe Glu Asn Arg Cys Ile Ala Leu Asp Asp
145                 150                 155                 160

Arg Tyr Gly Ala Trp Leu Ala Thr Arg His Leu Ile Gln Gln Gly His
                165                 170                 175

Thr Arg Ile Gly Tyr Leu Cys Ser Asn His Ser Ile Ser Asp Ala Glu
            180                 185                 190

Asp Arg Leu Gln Gly Tyr Tyr Asp Ala Leu Ala Glu Ser Gly Ile Ala
        195                 200                 205

Ala Asn Asp Arg Leu Val Thr Phe Gly Glu Pro Asp Glu Ser Gly Gly
210                 215                 220

Glu Gln Ala Met Thr Glu Leu Leu Gly Arg Gly Arg Asn Phe Thr Ala
225                 230                 235                 240

Val Ala Cys Tyr Asn Asp Ser Met Ala Ala Gly Ala Met Gly Val Leu
                245                 250                 255

Asn Asp Asn Gly Ile Asp Val Pro Gly Glu Ile Ser Leu Ile Gly Phe
            260                 265                 270

Asp Asp Val Leu Val Ser Arg Tyr Val Arg Pro Arg Leu Thr Thr Val
        275                 280                 285

Arg Tyr Pro Ile Val Thr Met Ala Thr Gln Ala Ala Glu Leu Ala Leu
290                 295                 300

Ala Leu Ala Asp Asn Arg Pro Leu Pro Glu Ile Thr Asn Val Phe Ser
305                 310                 315                 320

Pro Thr Leu Val Arg Arg His Ser Val Ser Thr Pro Ser Leu Glu Ala
                325                 330                 335

Ser His His Ala
            340

<210> SEQ ID NO 5
<211> LENGTH: 1083
<212> TYPE: DNA
<213> ORGANISM: Escherichia coli

<400> SEQUENCE: 5
gtgaaaccag taacgttata cgatgtcgca gagtatgccg gtgtctctta tcagaccgtt    60
tcccgcgtgg tgaaccaggc cagccacgtt tctgcgaaaa cgcgggaaaa agtggaagcg   120
gcgatggcgg agctgaatta cattcccaac cgcgtggcac aacaactggc gggcaaacag   180
tcgttgctga ttggcgttgc cacctccagt ctggccctgc acgcgccgtc gcaaattgtc   240
gcggcgatta atctcgcgcg cgatcaactg ggtgccagcg tggtggtgtc gatggtagaa   300
cgaagcggcg tcgaagcctg taaagcggcg gtgcacaatc ttctcgcgca acgcgtcagt   360
gggctgatca ttaactatcc gctggatgac caggatgcca ttgctgtgga agctgcctgc   420

```
actaatgttc cggcgttatt tcttgatgtc tctgaccaga cacccatcaa cagtattatt    480
ttctcccatg aagacggtac gcgactgggc gtggagcatc tggtcgcatt gggtcaccag    540
caaatcgcgc tgttagcggg cccattaagt tctgtctcgg cgcgtctgcg tctggctggc    600
tggcataaat atctcactcg caatcaaatt cagccgatag cggaacggga aggcgactgg    660
agtgccatgt ccggttttca acaaaccatg caaatgctga atgagggcat cgttcccact    720
gcgatgctgg ttgccaacga tcagatggcg ctgggcgcaa tgcgcgccat taccgagtcc    780
gggctgcgcg ttggtgcgga tatctcggta gtgggatacg acgatccga agacagctca    840 tgttatatcc cgccgttaac caccatcaaa caggattttc gcctgctggg gcaaaccagc    900
gtggaccgct tgctgcaact ctctcagggc caggcggtga agggcaatca gctgttgccc    960
gtctcactgg tgaaaagaaa aaccaccctg gcgcccaata cgcaaaccgc ctctccccgc   1020
gcgttggccg attcattaat gcagctggca cgacaggttt cccgactgga aagcgggcag   1080
tga                                                                 1083
```

<210> SEQ ID NO 6
<211> LENGTH: 21
<212> TYPE: DNA
<213> ORGANISM: Escherichia coli

<400> SEQUENCE: 6
aattgtgagc ggataacaat t                                              21

<210> SEQ ID NO 7
<211> LENGTH: 21
<212> TYPE: DNA
<213> ORGANISM: Escherichia coli

<400> SEQUENCE: 7
aaatgtgagc gagtaacaac c                                              21

<210> SEQ ID NO 8
<211> LENGTH: 21
<212> TYPE: DNA
<213> ORGANISM: Escherichia coli

<400> SEQUENCE: 8
ggcagtgagc gcaacgcaat t                                              21

<210> SEQ ID NO 9
<211> LENGTH: 20
<212> TYPE: DNA
<213> ORGANISM: Escherichia coli

<400> SEQUENCE: 9
aattgtgagc gctcacaatt                                                20

<210> SEQ ID NO 10
<211> LENGTH: 15
<212> TYPE: DNA
<213> ORGANISM: Artificial Sequence
<220> FEATURE:
<223> OTHER INFORMATION: Synthetic construct -spacer sequence

<400> SEQUENCE: 10
aattcagggt ggtga                                                     15

<210> SEQ ID NO 11
<211> LENGTH: 18

```
<212> TYPE: DNA
<213> ORGANISM: Artificial Sequence
<220> FEATURE:
<223> OTHER INFORMATION: Synthetic construct spacer sequence

<400> SEQUENCE: 11
caattcaggg tggtgaat                                                       18

<210> SEQ ID NO 12
<211> LENGTH: 18
<212> TYPE: DNA
<213> ORGANISM: Artificial Sequence
<220> FEATURE:
<223> OTHER INFORMATION: Synthetic construct linker sequence

<400> SEQUENCE: 12
ggctcaggtc tcgagttg                                                       18

<210> SEQ ID NO 13
<211> LENGTH: 1080
<212> TYPE: DNA
<213> ORGANISM: Artificial Sequence
<220> FEATURE:
<223> OTHER INFORMATION: Synthetic construct for optimized CMV/IE
      promoter region including E coli Lsym operator

<400> SEQUENCE: 13
atgaaaccag taacgttata cgacgtcgca gagtatgccg gtgtctctta tcagactgtt         60
tccagagtgg tgaaccaggc cagccatgtt tctgccaaaa ccagggaaaa agtggaagca        120
gccatggcag agctgaatta cattcccaac agagtggcac aacaactggc aggcaaacag        180
agcttgctga ttggagttgc cacctccagt ctggccctgc atgcaccatc tcaaattgtg        240
gcagccatta aatctagagc tgatcaactg ggagcctctg tggtggtgtc aatggtagaa        300
agaagtggag ttgaagcctg taaagctgca gtgcacaatc ttctggcaca aagagtcagt        360
gggctgatca ttaactatcc actggatgac caggatgcca ttgctgtgga agctgcctgc        420
actaatgttc cagcactctt tcttgatgtc tctgaccaga cacccatcaa cagtattatt        480
ttctcccatg aagatggtac aagactgggt gtggagcatc tggttgcatt gggacaccag        540
caaattgcac tgcttgcggg cccactcagt tctgtctcag caaggctgag actggccggc        600
tggcataaat atctcactag gaatcaaatt cagccaatag ctgaaagaga aggggactgg        660
agtgccatgt ctgggtttca acaaaccatg caaatgctga atgagggcat tgttcccact        720
gcaatgctgg ttgccaatga tcagatggca ctgggtgcaa tgagagccat tactgagtct        780
gggctgagag ttggtgcaga tatctcggta gtgggatacg acgataccga agacagctca        840
tgttatatcc cgccgttaac caccatcaaa caggattttc gcctgctggg gcaaaccagc        900
gtggaccgct tgctgcaact ctctcagggc caggcggtga agggcaatca gctgttgcca        960
gtctcactgg tgaagagaaa aaccacccctg gcacccaata cacaaactgc ctctccccgg     1020
gcattggctg attcactcat gcagctggca cgacaggttt cccgactgga aagcgggcag     1080

<210> SEQ ID NO 14
<211> LENGTH: 109
<212> TYPE: DNA
<213> ORGANISM: Artificial Sequence
<220> FEATURE:
<223> OTHER INFORMATION: Synthetic construct for optimized CMV/IE
      promoter region including E coli Lsym operator

<400> SEQUENCE: 14
```

```
cgccccgttg acgcaaatgg gcggtaggcg tgtacggtgg gaggtctata taagcagagc    60
tcgaattgtg agcgctcaca attgagctcg tttagtgaac cgtcagatc              109

<210> SEQ ID NO 15
<211> LENGTH: 4497
<212> TYPE: DNA
<213> ORGANISM: Artificial Sequence
<220> FEATURE:
<223> OTHER INFORMATION: Synthetic construct containing CMV enhancer/
      promoter, E. coli lacI operon, P2A cleavage site; luciferase
      reporter, hammerhead ribozyme with tetracycline aptamer and poly
      A, flanked by AAV ITRs

<400> SEQUENCE: 15
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctacgta gcaagctagc   180
ctagttatta atagtaatca attacggggt cattagttca tagcccatat atggagttcc   240
gcgttacata acttacggta aatggcccgc ctggctgacc gcccaacgac ccccgcccat   300
tgacgtcaat aatgacgtat gttcccatag taacgccaat agggactttc cattgacgtc   360
aatgggtgga gtatttacgg taaactgccc acttggcagt acatcaagtg tatcatatgc   420
caagtacgcc ccctattgac gtcaatgacg gtaaatggcc cgcctggcat tatgcccagt   480
acatgacctt atgggacttt cctacttggc agtacatcta cgtattagtc atcgctatta   540
ccatggtgat gcggttttgg cagtacacca atgggcgtgg atagcggttt gactcacggg   600
gatttccaag tctccacccc attgacgtca atgggagttt gttttggaat tgtgagcgct   660
cacaattgac accaaaatca acgggacttt ccaaaatgtc gtaacaactc cgccccgttg   720
acgcaaatgg gcggtaggcg tgtacggtgg gaggtctata taagcagagc tcgaattgtg   780
agcgctcaca attgagctcg tttagtgaac cgtcagatcg ttggtcgtga ggcactgggc   840
aggtaagtat caaggttaca agacaaattg tgagcgctca caattggttt aaggagacca   900
atagaaactg gcttgtcga cagagaag actcttgcgt ttctgatagg cacctattgg   960
tcttactgac atccactttg cctttctctc cacaggtgtc cactcccagt tcaattacag   1020
atcaggccta tggtgaagcc cgtgaccctg tacgacgtgg ccgaatatgc cggcgtgtcc   1080
taccagaccg tgtcccgggt cgtgaatcag gccagcacg tgtccgccaa gacccgcgaa   1140
aaagtggaag ccgccatggc cgagctgaac tacatcccca acagagtggc ccagcagctg   1200
gccggcaaac agtctctgct gatcggcgtg gccacaagca gcctggctct gcatgccct   1260 tctcagatcg tggccgccat caagagcaga gccgaccagc tgggagccag cgtggtggtg   1320
tctatggtgg aacgctctgg cgtggaagcc tgcaaagccg ccgtgcacaa tctgctggcc   1380
cagagagtgt ccggcctgat catcaactac ccctggacg accaggacgc cattgccgtg   1440
gaagctgcct gcaccaatgt gcccgccctg ttcctggacg tgtccgatca gacccccatc   1500
aacagcatca tctggagcca cgaggacggc acccggctgg gagtggaaca tctggtggct   1560 ctggacacc agcagatcgc cctgctggct ggacctctgt cctccgtgtc tgccagactg   1620
agactggccg gctggcacaa gtacctgacc cggaaccaga tccagcctat cgccgagaga   1680
gagggcgatt ggagcgccat gtccggcttc cagcagacca tgcagatgct gaacgagggc   1740
atcgtgccca ccgccatgct ggtggccaat gaccagatgg ccctgggcgc catgagagcc   1800
atcacagagt ctggcctgag agtgggcgcc gacatctccg tcgtgggcta cgacgatacc   1860
```

```
gaggacagca gctgttacat ccccccctg accaccatca agcaggactt cagactgctg    1920
ggacagacca gcgtggaccg gctgctacag ctgtctcagg acaggccgt gaagggcaat    1980 cagctgctgc ctgtgtccct cgtgaagaga aagaccaccc tggcccccaa cacccagacc    2040
gcttctccaa gagccctggc cgacagcctg atgcagctgg ctagacaggt gtcccggctg    2100
gaaagcggac agactagtgc aagacaggtt ccagactgg aaagtgggca ggcagctctg    2160
cccaagaaga agcgaaaggt gctgcaggga agcggagcta ctaacttcag cctgctgaag    2220
caggctggag acgtggagga aaccctggga cctagatcta tggaagacgc caaaaacata    2280
aagaaaggcc cggcgccatt ctattcactc gaagacggga ccgccggcga gcagctgcac    2340
aaagccatga agcgctacgc cctggtgccc ggcaccatcg cctttaccga cgcacatatc    2400
gaggtggaca ttacctacgc cgagtacttc gagatgagcg ttcggctggc agaagctatg    2460
aagcgctatg gcctgaatac aaaccatcgg atcgtggtgt gcagcgagaa tagcttgcag    2520
ttcttcatgc ccgtgttggg tgccctgttc atcggtgtgg ctgtggcccc agctaacgac    2580
atctacaacg agcgcgagct gctgaacagc atgggcatca gccagcccac cgtcgtattc    2640
gtgagcaaga agggctgca aaagatcctc aacgtgcaaa agaagctacc gatcatacaa    2700
aagatcatca tcatggatag caagaccgac taccagggct ccaaagcat gtacaccttc    2760 gtgacttccc atttgccacc cggcttcaac gagtacgact cgtgcccga gagcttcgac    2820 cgggacaaaa ccatcgccct gatcatgaac agtagtggca gtaccggatt gcccaagggc    2880
gtagccctac cgcaccgcac cgcttgtgtc cgattcagtc atgcccgcga ccccatcttc    2940
ggcaaccaga tcatccccga caccgctatc ctcagcgtgg tgccatttca ccacggcttc    3000
ggcatgttca ccacgctggg ctacttgatc tgcggctttc gggtcgtgct catgtaccgc    3060
ttcgaggagg agctattctt gcgcagcttg caagactata agattcaatc tgccctgctg    3120
gtgcccacac tatttagctt cttcgctaag agcactctca tcgacaagta cgacctaagc    3180
aacttgcacg agatcgccag cggcggggcg ccgctcagca aggaggtagg tgaggccgtg    3240
gccaaacgct tccacctacc aggcatccgc caggggctacg gcctgacaga aacaaccagc    3300
gccattctga tcaccccga aggggacgac aagcctggcg cagtaggcaa ggtggtgccc    3360
ttcttcgagg ctaaggtggt ggacttggac accggtaaga cactgggtgt gaaccagcgc    3420
ggcgagctgt gcgtccgtgg ccccatgatc atgagcggct acgttaacaa ccccgaggct    3480
acaaacgctc tcatcgacaa ggacggctgg ctgcacagcg gcgacatcgc ctactgggac    3540
gaggacgagc acttcttcat cgtggaccgg ctgaagagcc tgatcaaata caagggctac    3600
caggtagccc cagccgaact ggagagcatc ctgctgcaac accccaacat cttcgacgcc    3660
ggggtcgccg gcctgcccga cgacgatgcc ggcgagctgc ccgccgcagt cgtcgtgctg    3720
gaacacggta aaaccatgac cgagaaggag atcgtggact atgtggccag ccaggttaca    3780
accgccaaga gctgcgcgg tggtgttgtg ttcgtggacg aggtgcctaa aggactgacc    3840
ggcaagttgg acgcccgcaa gatccgcgag atcctcataa aggccaagaa gggcggaaag    3900
atcgccgtgg cggccgcaga ttacaaggat gacgatgaca gtaagttta aaccaaacaa    3960 acaaggcgc gtcctggatt cgtgcaaaaa cataccagat tcgatctgg agaggtgaag    4020 aatacgacca ccttgtacat ccagctgatg agtcccaaat aggacgaaac gcgctcaaac    4080
aaacaaaagt acttaagaca tgataagata cattgatgag tttggacaaa ccacaactag    4140
aatgcagtga aaaaaatgct ttatttgtga aatttgtgat gctattgctt tatttgtaac    4200
cattataagc tgcaataaac aagttaacaa caacaattgc attcatttta tgtttcaggt    4260
```

```
tcaggggag  atgtgggagg  tttttaaag  caagtaaaac  ctctacaaat  gtggtaaact     4320
cgagttctac  gtagataagt  agcatggcgg  gttaatcatt  aactacaagg  aaccctagt    4380 gatggagttg  gccactcct   ctctgcgcgc  tcgctcgctc  actgaggccg  ggcgaccaaa   4440
ggtcgcccga  cgcccgggct  ttgcccgggc  ggcctcagtg  agcgagcgag  cgcgcag      4497
```

UNITED STATES PATENT AND TRADEMARK OFFICE
CERTIFICATE OF CORRECTION

PATENT NO. : 10,392,622 B2  
APPLICATION NO. : 15/500591  
DATED : August 27, 2019  
INVENTOR(S) : Mitchell Lewis et al.

Page 1 of 1

It is certified that error appears in the above-identified patent and that said Letters Patent is hereby corrected as shown below:

In the Specification

On Column 1, the heading "STATEMENT REGARDING FEDERALLY SPONSORED RESEARCH OR DEVELOPMENT" and paragraph immediately following is removed.

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*